(12) United States Patent
Keith et al.

(10) Patent No.: US 9,987,310 B2
(45) Date of Patent: Jun. 5, 2018

(54) CARDIAC PROGENITOR CELLS AND METHODS OF USE THEREFOR

(71) Applicant: University of Louisville Research Foundation, Inc., Louisville, KY (US)

(72) Inventors: Matthew C. L. Keith, Louisville, KY (US); Marcin Wysoczynski, Louisville, KY (US); Roberto Bolli, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days. days.

(21) Appl. No.: 15/039,082

(22) PCT Filed: Nov. 25, 2014

(86) PCT No.: PCT/US2014/067395
§ 371 (c)(1),
(2) Date: May 25, 2016

(87) PCT Pub. No.: WO2015/081094
PCT Pub. Date: Jun. 4, 2015

(65) Prior Publication Data
US 2017/0239298 A1    Aug. 24, 2017

Related U.S. Application Data

(60) Provisional application No. 61/909,729, filed on Nov. 27, 2013.

(51) Int. Cl.
*A61K 35/34* (2015.01)
*C12N 5/077* (2010.01)
*A61K 45/06* (2006.01)
*A61K 9/00* (2006.01)

(52) U.S. Cl.
CPC ............ *A61K 35/34* (2013.01); *A61K 9/0019* (2013.01); *A61K 45/06* (2013.01); *C12N 5/0657* (2013.01); *C12N 2501/105* (2013.01); *C12N 2501/11* (2013.01); *C12N 2501/115* (2013.01); *C12N 2501/125* (2013.01); *C12N 2501/135* (2013.01); *C12N 2501/165* (2013.01); *C12N 2533/20* (2013.01); *C12N 2533/32* (2013.01); *C12N 2533/52* (2013.01); *C12N 2533/54* (2013.01); *C12N 2533/90* (2013.01)

(58) Field of Classification Search
CPC .............................. A61K 35/34; C12N 5/0657
See application file for complete search history.

(56) References Cited

U.S. PATENT DOCUMENTS

| | | | |
|---|---|---|---|
| 7,547,674 B2 | 6/2009 | Anversa | |
| 7,862,810 B2 | 1/2011 | Anversa et al. | |
| 8,119,123 B2 | 2/2012 | Anversa et al. | |
| 8,124,071 B2 | 2/2012 | Anversa et al. | |
| 8,193,161 B2 | 6/2012 | Hosoda et al. | |
| 8,247,374 B2 | 8/2012 | Anversa | |
| 8,343,479 B2 | 1/2013 | Anversa et al. | |
| 8,512,696 B2 | 8/2013 | Anversa et al. | |
| 9,155,762 B2 | 10/2015 | Ratajczak et al. | |
| 2007/0054397 A1 | 3/2007 | Ott et al. | |
| 2008/0267921 A1 | 10/2008 | Marban et al. | |
| 2009/0180998 A1 | 7/2009 | Anversa et al. | |
| 2010/0068811 A1 | 3/2010 | Marban et al. | |
| 2010/0260727 A1 | 10/2010 | Hare et al. | |
| 2011/0070647 A1 | 3/2011 | Dezawa et al. | |
| 2012/0020935 A1 | 1/2012 | Giacomello et al. | |
| 2012/0288481 A1 | 11/2012 | Anversa et al. | |
| 2012/0321595 A1 | 12/2012 | Anversa et al. | |
| 2013/0295060 A1* | 11/2013 | Yang, II | A61K 35/34 424/93.7 |
| 2014/0271575 A1* | 9/2014 | Rodriguez-Borlado | C12N 5/0657 424/93.7 |

FOREIGN PATENT DOCUMENTS

| | | |
|---|---|---|
| EP | 2258833 | 12/2010 |
| WO | WO 2004/019767 | 3/2004 |
| WO | WO 2008/081457 | 7/2008 |
| WO | WO 2009/058983 | 5/2009 |
| WO | WO 2009/073616 | 6/2009 |
| WO | WO 2010/039241 | 4/2010 |

OTHER PUBLICATIONS

Bearzi et al., "Human Cardiac Stem Cells," PNAS, 104(35):14068-14073 (Aug. 28, 2007).
Bolli et al., "Cardia Stem Cells in Patients with Ischaemic Cardiomyopathy (SCIPIO): Initial Results of a Randomized Phase I Trial," Lancet, 378:1847-1857 (Nov. 14, 2011).
Hierlihy et al., "The post-natal heart contains a myocardial stem cell population," FEBS Lett. 530:239-243 (2002).
Hou et al., "Isolation, characterization and spatial distribution of cardiac progenitor cells in the sheep heart," J Clin Exp Cardiolog, S6:004 (2012); pp. 1-6. http://dx.doi.org/10.4172/2135-9880.
International Search Report and Written Opinion corresponding to PCT/US14/67395 dated Mar. 4, 2015.

(Continued)

*Primary Examiner* — Daniel C Gamett
(74) *Attorney, Agent, or Firm* — Jenkins, Wilson, Taylor & Hunt, P.A.

(57) ABSTRACT

Provided are pharmaceutical compositions that include a pharmaceutically acceptable carrier and isolated post-natal cardiac progenitor cells (CPCs) and/or progeny cells thereof that are SSEA3-positive and c-kit-negative. Also provided are methods for preparing cells capable of repairing damaged myocardium, methods for isolating populations of SSEA3-positive/c-kit-negative CPCs from cardiac tissue samples, methods for preparing an isolated cell population enriched in post-natal SSEA3-positive/c-kit-negative CPCs, therapeutic methods for using the presently disclosed cells and populations of cells to treat subjects in need thereof, and cell cultures that contain the presently disclosed cells and populations of cells.

21 Claims, 46 Drawing Sheets

(56) References Cited

OTHER PUBLICATIONS

Laugwitz et al., "Postnatal lsl1-positive cardioblasts enter fully differentiated cardiomyocyte lineges," Nature, 433:647-653. Erratum in Nature 446:934 (2005).
Messina et al., "Isolation and expansion of adult cardiac stem cells from human and murine heart," Circ Res, 95:911-921 (2004).
Notification Concerning Transmittal of International Preliminary Report on Patentability (Chapter I of the Patent Cooperation Treaty) corresponding to PCT/US14/67395 dated Jun. 9, 2016.
Smith et al., "Regenerative potential of cardiosphere-derived cells expanded from percutaneous endomyocardial biopsy specimens," Circulation, 115: 896-908 (2007).
Srikanth et al., "Fetal cardiac mesencyhmal stem cells express embryonal markers and exhibit differentation into cells of all three germ layers," World J Stem Cells, 5(1):26-33 (Jan. 26, 2013).
Srikanth et al., "Isolation and characterization of cardiac MSCS from rat foetal hearts," Int J Reg Med, 1 (2012); pp. 1-8; DOI:10.5772/51367.

* cited by examiner

CARDIAC PROGENITOR CELLS AND METHODS OF USE THEREFOR

CROSS REFERENCE TO RELATED APPLICATIONS

This application is a United States National Stage Application filed under 35 U.S.C. § 371 of PCT International Patent Application Ser. No. PCT/US2014/067395, filed Nov. 25, 2014, which itself is based on and claims priority to U.S. Provisional Patent Application Ser. No. 61/909,729, filed Nov. 27, 2013, the disclosure of each of which is incorporated by reference herein in its entirety.

TECHNICAL FIELD

The presently disclosed subject matter relates to subpopulations of resident cardiac progenitor cells (CPCs) that are positive for the embryonic stem cell-associated antigen stage-specific embryonic antigen 3 (SSEA-3) and do not express c-kit. These cells, referred to herein as Embryonic Antigen-positive Cardiac Progenitor Cells (EA-CPCs), are demonstrably different from previously identified cardiac stem and progenitor cells, bone marrow mesenchymal stem cells (MSCs), hematopoietic stem cells (HSCs), and other stem/progenitor cell populations. In some embodiments, the SSEA3-positive/c-kit-negative cells of the presently disclosed subpopulations are also CD34-negative, CD45-negative, or both CD34-negative and CD45-negative. In some embodiments, the presently disclosed subject matter also provides methods for isolating these subpopulations of CPCs from myocardium and uses for these subpopulations and progeny cell populations expanded therefrom for heart and/or myocardial repair.

BACKGROUND

There has been a paradigm shift in the dogma that the heart becomes terminally differentiated shortly after the neonatal period. This dogma has been overturned with the widely accepted discoveries of not only dividing cardiomyocytes but also resident stem cells contained within myocardial niches. (Anversa et al., 1998; Kajstura et al., 1998, Beltrami et al., 2001). It has been determined that this pool of stem cells is not made up of mobilized bone marrow cells, but are actual stem cells residing within the myocardial tissue itself (Beltrami et al., 2003). However, noting the plethora of varying phenotypes present within the myocardium that contribute to both functional and structural integrity of the organ, it is unlikely that the populations of c-kit-positive cardiac stem cells disclosed in Anversa et al., 1998; Kajstura et al., 1998; and Beltrami et al., 2001 are solely responsible for not only maintenance of homeostasis but also mounting response to myocardial injury.

Various isolation methods have been described to obtain cardiac stem cells (CSCs; see e.g., Hierlihy et al., 2002, Bearzi et al., 2007; Goumans et al., 2007; Smith et al., 2007). Several reports describe that CSCs can be isolated after explant and/or enzymatic dissociation based on expansion centered on the expression of membrane antigens such as c-kit and Sca-1 (see e.g., Bearzi et al., 2007; Goumans et al., 2007, Laugwitz et al., 2005). Most of these isolation methods are based on antigen-antibody interactions and magnetic bead sorting. To date, this is the best option for synthesis of a clinical grade therapeutic product as the single use of reagents limits introduction of pathogens unlike other purification techniques such as fluorescence based sorting by use of enzymatic activity or fluorophore coupled antibody to target interaction, although other cell sorting systems such as the Sony Cell Sorter SH800 that employs a disposable plastic chip can also be used for clinical applications.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides pharmaceutical compositions comprising, consisting essentially of, or consisting of a pharmaceutically acceptable carrier and isolated SSEA3-positive/c-kit-negative cardiac progenitor cells (EA-CPCs) and/or in vitro expanded progeny cells thereof, wherein the isolated SSEA3-positive/c-kit-negative EA-CPCs are isolated from post-natal myocardium (e.g., pediatric myocardium, adult myocardium, etc.). In some embodiments, the EA-CPCs are isolated from human post-natal myocardium. In some embodiments, the concentration of EA-CPCs and/or in vitro expanded progeny cells thereof is about $1 \times 10^5$ cells/ml to about $1 \times 10^9$ cells/ml in the pharmaceutical composition. In some embodiments, the presently disclosed pharmaceutical compositions further comprise one or more cell types selected from the group consisting of non-cardiac-derived SSEA3-positive cells, SSEA4-positive cells, c-kit-positive cardiac stem cells, hematopoietic stem cells (HSCs), mesenchymal stem cells (MSCs), endothelial progenitor cells (EPCs), bone marrow cells (BMCs), aldehyde dehydrogenase positive (ALDH-positive) cells, very small embryonic like cells (VSELs; see U.S. Patent Application Publication No. 2009/0220466; PCT International Patent Application Publication No. WO 2010/039241), and/or cardiosphere-derived cells (CDCs; see e.g., Messina et al., 2004). In some embodiments, the pharmaceutically acceptable carrier is acceptable for use in a human. In some embodiments, the pharmaceutical compositions further comprise one or more growth factors and/or cytokines, wherein the one or more growth factors and/or cytokines are optionally selected from the group consisting of IGF-1, FGF, HGF, SDF-1, VEGF, BMPs, PDGF, G-CSF, GM-CSF, TGF-β, and SCF, or any combination thereof. In some embodiments, the pharmaceutical compositions are formulated as injectables. In some embodiments, the EA-CPCs and/or the in vitro expanded progeny cells thereof are also CD34-negative, CD45-negative, or both CD34-negative and CD45-negative.

In some embodiments, the presently disclosed subject matter also provides pharmaceutical compositions comprising, consisting essentially of, or consisting of c-kit-negative, CD34-negative, CD45-negative, and SSEA3-positive cells isolated from a cardiac tissue sample. In some embodiments, the presently disclosed pharmaceutical compositions are isolated by a method comprising: disrupting a cardiac tissue sample isolated from a human subject to obtain tissue fragments and/or single cells; placing the tissue fragments and/or single cells into culture; culturing the tissue fragments and/or single cells in a culture medium for a time and under conditions sufficient to generate $10^4$-$10^9$ cells; harvesting all or at least a portion of the tissue fragments and/or single cells from the culture, optionally disrupting the harvested cells to produce a single cell suspension; purifying a subpopulation of c-kit-negative, CD34-negative, CD45-negative, and SSEA3-positive cells from the single cells and/or the single cell suspension; expanding the c-kit-negative, CD34-negative, CD45-negative, and SSEA3-positive cells in culture for a time and under conditions sufficient to generate adequate numbers of c-kit-negative, CD34-negative, CD45-negative, and SSEA3-positive cells; and optionally combining the expanded c-kit-negative, CD34-negative, CD45-negative, and SSEA3-positive cells with one or more of c-kit-positive cardiac stem cells, hematopoietic stem cells (HSCs), mesenchymal stem cells (MSCs), endothelial progenitor cells (EPCs), bone marrow cells (BMCs), aldehyde dehydrogenase positive (ALDH-positive) cells, very small embryonic like cells (VSELs), and/or cardiosphere-derived cells (CDCs), whereby cells capable of repairing damaged or poorly functioning myocardium are prepared. The cells capable of repairing damaged or poorly functional myocardium so prepared can then be formulated as a pharmaceutical composition of the presently disclosed subject matter.

The presently disclosed subject matter also provides in some embodiments cell cultures comprising post-natal SSEA3-positive/c-kit-negative cardiac progenitor cells (EA-CPCs) that are also optionally CD34-negative and/or CD45-negative and/or progeny cells thereof growing on a surface, wherein at least about 50%, 75%, 85%, 90%, 95%, or 99% of the population of EA-CPCs and/or the progeny cells thereof present in the cell culture are SSEA3-positive/c-kit-negative, and optionally are also CD34-negative and/or CD45-negative. In some embodiments, EA-CPCs and/or the progeny cells thereof are maintained as subconfluent in the cell culture. In some embodiments, the surface upon which the EA-CPCs and/or the progeny cells thereof are growing comprises a growth-promoting medium and/or substrate selected from the group consisting of poly-lysine, gelatin, MATRIGEL®, fibronectin, vitronectin, an extracellular matrix component, and a scaffold, or any combination thereof. In some embodiments, the EA-CPCs and/or the progeny cells thereof express at least one cardiac-specific marker selected from the group consisting of Nkx2.5, Gata4, Mef2c, Isl1, and Gata6; one or more pluripotency-associated markers selected from the group consisting of Oct3, Oct4, Nanog, and Sox2; one or more other markers selected from the group consisting of SSEA1, CD105, CD73, CD90, CD29, CD44, CD166, SSEA5, ALDH, and alkaline phosphatase; or any combination thereof.

In some embodiments, the presently disclosed subject matter also provides methods for isolating populations of SSEA3-positive/c-kit-negative cardiac progenitor cells (EA-CPCs) that are also optionally CD34-negative and/or CD45-negative from cardiac tissue samples and/or in vitro expanded progeny cells derived therefrom. In some embodiments, the methods comprise (a) disrupting a cardiac tissue sample isolated from a subject to obtain tissue fragments and/or single cells, optionally wherein the subject is a post-natal human subject; (b) culturing the tissue fragments and/or single cells in vitro; (c) harvesting all or at least a portion of the tissue fragments and/or single cells; (d) disrupting the harvested tissue fragments and/or single cells to produce a single cell suspension; and (e) purifying a subpopulation of SSEA3-positive/c-kit-negative CPCs that are also optionally CD34-negative and/or CD45-negative from the single cell suspension, whereby a population of EA-CPCs that are also optionally CD34-negative and/or CD45-negative are isolated from the cardiac tissue sample. In some embodiments, the disrupting comprises treating the cardiac tissue sample with an enzyme for a time and under conditions sufficient to create a cell preparation in which at least 50% of the cells are single cells. In some embodiments, the cardiac tissue sample is obtained from a post-natal cardiac tissue biopsy, optionally a cardiac tissue biopsy from an adult, and optionally a cardiac tissue biopsy from a human.

In some embodiments, the culturing comprises placing the obtained tissue fragments and/or single cells onto a surface, wherein the surface is optionally coated with a growth-promoting medium selected from the group consisting of poly-lysine, gelatin, MATRIGEL®, laminin, collagen, and an extracellular matrix preparation, and optionally wherein the culturing is in the presence of at least one growth factor selected from the group consisting of FGF, IGF-1, TGF-β, PDGF, VEGF, SCF, and a BMP, or any combination thereof. In some embodiments, the purifying employs Fluorescence-Activated Cell Sorting (FACS) and/or Magnetic Activated Cell Sorting (MACS), and further wherein the purifying simultaneously or sequentially enriches for a population of SSEA3-positive cells and removes c-kit-positive cells, and optionally also removes CD34-positive cells, CD45-positive cells, or both. In some embodiments, the purifying comprises FACS and/or MACS sorting of the single cell suspension and collecting those cells that are SSEA3-positive and c-kit-negative, and optionally further comprises collecting those cells that are SSEA3-positive/c-kit-negative/CD34-negative, SSEA3-positive/c-kit-negative/CD45-negative, and/or SSEA3-positive/c-kit-negative/CD34-negative/CD45-negative. In some embodiments, the presently disclosed methods further comprise expanding the tissue fragments and/or single cells and/or the cells of the single cell suspension by culturing the tissue fragments and/or single cells and/or the single cell suspension for a time and under condition sufficient to generate at least about $10^8$ cells in the culture prior to the harvesting step, the purifying step, or both. In some embodiments, the expanding is sufficient to provide at least $10^4$ SSEA3-positive/c-kit-negative cells after the purifying step.

The presently disclosed subject matter also provides in some embodiments methods for preparing isolated cell populations enriched in post-natal SSEA3-positive/c-kit-negative cardiac progenitor cells (EA-CPCs) that are also optionally CD34-negative and/or CD45-negative. In some embodiments, the methods comprise disrupting a cardiac tissue sample obtained from a post-natal subject to obtain tissue fragments and/or single cells; culturing the tissue fragments and/or single cells in a culture medium for a time and under conditions sufficient to generate $10^4$-$10^9$ cells; harvesting all or at least a portion of the adhered tissue fragments and/or single cells from the culture, optionally disrupting the harvested cells to produce a single cell suspension; purifying one or more subpopulations of SSEA3-positive/c-kit-negative cells, a subpopulation of SSEA3-positive/c-kit-negative/CD34-negative cells, a subpopulation of SSEA3-positive/c-kit-negative/CD45-negative cells, and/or a subpopulation of SSEA3-positive/c-kit-negative/CD34-negative/CD45-negative cells from the single cell suspension; and expanding the one or more subpopulations in culture for a time and under conditions sufficient to generate at least about $10^4$ SSEA3-positive/c-kit-negative cells that are also optionally CD34-negative and/or CD45-negative, wherein an isolated cell population enriched in post-natal SSEA3-positive/c-kit-negative cardiac progenitor cells (EA-CPCs) that are also optionally CD34-negative and/or CD45-negative is prepared. In some embodiments, the cardiac tissue sample comprises tissue and/or cells isolated from and/or expanded from cardiac right atrial appendage tissue, left atrial appendage tissue, cardiac ventricular tissue, cardiac valvular tissue, cardiac vascular tissue, and/or endomyocardial biopsy tissue. In some embodiments, cells of the one or more subpopulations express one or more markers selected from the group consisting of ISL1, GATA4, NKX2.5, MEF2C, GATA6, BRACHYURY, MESP1, OCT3, OCT4, NANOG, and SOX2. In some embodiments, the tissue fragments and/or single cells are cultured in the absence of exogenously added feeder cells. In some embodiments, the culturing is on a support that comprises a growth-promoting medium selected from the group consisting of poly-lysine, gelatin, MATRIGEL®, fibronectin, laminin, collagen, vitronectin, an extracellular matrix component, and a natural and/or synthetic scaffold. In some embodiments, the culturing is in a medium that comprises at least one growth promoting factor selected from the group consisting of IGF-1, FGF, a BMP, EGF, SCF, PDGF, and VEGF.

The presently disclosed subject matter also provides in some embodiments methods for preparing isolated cell populations enriched in post-natal SSEA3-positive/c-kit-negative cardiac progenitor cells (EA-CPCs) that are also optionally CD34-negative and/or CD45-negative. In some embodiments, the methods comprise disrupting a post-natal cardiac tissue sample to obtain tissue fragments and/or single cells; culturing the tissue fragments and/or single cells in a culture medium for a time and under conditions sufficient to generate $10^4$-$10^9$ cells; harvesting all or at least a portion of the cultured tissue fragments and/or single cells from the culture, and optionally disrupting the harvested cells to produce a single cell suspension; purifying from the single cell suspension a subpopulation of SSEA3-positive/c-kit-negative cells, optionally further purifying from the single cell suspension SSEA3-positive/c-kit-negative cells that are also CD34-negative and/or CD45-negative; and expanding the SSEA3-positive/c-kit-negative cells in culture for a time and under conditions sufficient to generate at least about $10^4$ SSEA3-positive/c-kit-negative and optionally CD34-negative and/or CD45-negative cells, wherein an isolated cell population enriched in post-natal SSEA3-positive/c-kit-negative CPCs that are also optionally CD34-negative and/or CD45-negative is prepared. In some embodiments, the cardiac tissue sample comprises tissue and/or cells isolated from cardiac right atrial appendage (RAA) tissue, left atrial appendage tissue, cardiac ventricular tissue, cardiac valvular tissue, cardiac vascular tissue, endomyocardial biopsy tissue, or any combination thereof. In some embodiments, the SSEA3-positive/c-kit-negative and optionally CD34-negative and/or CD45-negative cells express at least one marker selected from the group consisting of Isl1, GATA4, Nkx2.5, Mef2c, GATA6, Brachyury, MESP1, Oct3/4, Nanog, and Sox2. In some embodiments, the isolated stem cells or progenitor cells are cultured in the absence of added feeder cells, optionally wherein the added feeder cells comprise murine epithelial cells (MEFs), mesenchymal feeder cells, or both. In some embodiments, the culturing is on a surface coated with a growth-promoting medium selected from the group consisting of poly-lysine, gelatin, MATRIGEL®, fibronectin, laminin, collagen, vitronectin, an extracellular matrix component, and a natural or synthetic scaffold, or any combination thereof. In some embodiments, the culturing is in a medium that comprises at least one growth promoting factor selected from the group consisting of IGF-1, FGF, a BMP, EGF, SCF, PDGF, and VEGF. In some embodiments, the purifying step further comprises purifying CD34-negative, CD45-negative, or both CD34-negative and CD45-negative cells from the single cell suspension or from the subpopulation of c-kit-negative and SSEA3-positive cells isolated therefrom, optionally by removing CD34-positive and/or CD45-positive cells from the single cell suspension or from the subpopulation of c-kit-negative and SSEA3-positive cells isolated therefrom. In some embodiments, the expanding step further comprises expanding cells that are c-kit-negative and SSEA3-positive as well as CD34-negative, CD45-negative, or both CD34-negative and CD45-negative.

In some embodiments, the presently disclosed subject matter also provides methods for preparing cells capable of repairing damaged myocardium. In some embodiments, the methods comprise (a) disrupting a cardiac tissue sample to obtain tissue fragments and/or single cells; (b) placing the tissue fragments and/or single cells into culture; (c) culturing the tissue fragments and/or single cells in a culture medium for a time and under conditions sufficient to generate $10^4$-$10^9$ cells; (d) harvesting all or at least a portion of the adhered tissue fragments and/or single cells from the culture, and optionally disrupting the harvested cells to produce a single cell suspension; (e) purifying a subpopulation of SSEA3-positive/c-kit-negative cells from the single cell suspension, wherein the SSEA3-positive/c-kit-negative cells are optionally CD34-negative and/or CD45-negative; (f) expanding the SSEA3-positive/c-kit-negative and optionally CD34-negative and/or CD45-negative cells in culture for a time and under conditions sufficient generate at least about $10^4$ SSEA3-positive/c-kit-negative cells that are optionally also CD34-negative and/or CD45-negative, whereby cells capable of repairing damaged myocardium are prepared. In some embodiments, the presently disclosed methods further comprise isolating CD34-negative and/or CD45-negative cells before, after, and/or during the purifying step, the expanding step, or both in order to prepare a pharmaceutical composition comprising, consisting essentially of, or consisting of c-kit-negative, SSEA3-positive, and CD34-negative and/or CD45-negative cells capable of repairing damaged or poorly functioning myocardium.

The presently disclosed subject matter also provides in some embodiments pharmaceutical compositions comprising, consisting essentially of, or consisting of a pharmaceutically acceptable carrier and SSEA3-positive/c-kit-negative cardiac progenitor cells (EA-CPCs) that are also optionally CD34-negative and/or CD45-negative and/or in vitro expanded progeny cells thereof prepared by a method as disclosed herein.

The presently disclosed subject matter also provides in some embodiments methods for regenerating and/or repairing damaged and/or poorly functional myocardium in a subject in need thereof. In some embodiments, the presently disclosed methods comprise administering a dose of a pharmaceutical composition as disclosed herein to an area of damaged and/or poorly functional myocardium in the subject, wherein the post-natal SSEA3-positive/c-kit-negative cardiac progenitor cells (EA-CPCs) that are also optionally CD34-negative and/or CD45-negative and/or in vitro expanded progeny cells thereof differentiate into mature, functional cardiomyocytes, smooth muscle cells, and/or endothelium and/or induce the generation of new cardiomyocytes, smooth muscle, endothelium, and/or vasculature following administration to an extent sufficient to regenerate and/or repair the damaged and/or poorly functional myocardium in the subject. In some embodiments, the post-natal SSEA3-positive/c-kit-negative EA-CPCs that are also optionally CD34-negative and/or CD45-negative and/or progeny cells thereof are autologous or allogeneic to the subject. In some embodiments, the pharmaceutical composition is administered to a location in the subject selected from the group consisting of an infarct zone, a border zone, a non-infarct zone, a scar, a functional region, a dysfunctional region, a valvular region, a perivalvular region, or any combination thereof of the myocardium in the subject. In some embodiments, the pharmaceutical composition is administered transendocardially, intramyocardially, transepicardially by injection or optionally via a catheter. In some embodiments, the pharmaceutical composition further comprises an additional component selected from the group consisting of a growth factor, a cytokine, a natural or synthetic extracellular matrix component, and a scaffold, or any combination thereof. In some embodiments, the subject has a history of acute myocardial infarction and/or remote myocardial infarction within one year prior to administering the pharmaceutical composition.

The presently disclosed subject matter also provides in some embodiments methods for regenerating and/or repairing damaged and/or poorly functional myocardium in a subject in need thereof. In some embodiments, the presently disclosed methods comprise providing a pharmaceutical composition comprising SSEA3-positive/c-kit-negative cardiac progenitor cells (EA-CPCs) that are also optionally CD34-negative and/or CD45-negative and/or in vitro expanded progeny cells thereof, wherein the SSEA3-positive/c-kit-negative EA-CPCs that are also optionally CD34-negative and/or CD45-negative are autologous or allogeneic to the subject; and administering the pharmaceutical composition to an area of damaged myocardium in the subject, wherein the SSEA3-positive/c-kit-negative EA-CPCs that are also optionally CD34-negative and/or CD45-negative and/or in vitro expanded progeny cells thereof directly differentiate into and/or indirectly cause formation of new mature, functional cardiomyocytes, smooth muscle, endothelium, and/or vasculature following administration, thereby regenerating and/or repairing damaged myocardium in the subject. In some embodiments, the SSEA3-positive/c-kit-negative EA-CPCs that are also optionally CD34-negative and/or CD45-negative are provided by harvesting myocardial tissue from the subject and/or an allogeneic donor and isolating SSEA3-positive/c-kit-negative EA-CPCs that are also optionally CD34-negative and/or CD45-negative from the myocardial tissue, and optionally expanding the SSEA3-positive/c-kit-negative EA-CPCs that are also optionally CD34-negative and/or CD45-negative EA-CPCs in culture to generate in vitro expanded progeny cells therefrom. In some embodiments, the subject and the allogeneic donor are both humans. In some embodiments, at least 50%, 55%, 60%, 65%, 70%, 75%, 80%, 85%, 90%, 95%, or 99% of the cells present in the pharmaceutical composition are SSEA3-positive/c-kit-negative and optionally CD34-negative and/or CD45-negative. In some embodiments, the damaged and/or poorly functional myocardium results from ischemic cardiomyopathy. In some embodiments, the damaged and/or poorly functional myocardium results from non-ischemic cardiomyopathy. In some embodiments, the damaged and/or poorly functional myocardium results from a cardiac injury or disease selected from the group consisting of myocardial infarct, left ventricular hypertrophy, right ventricular hypertrophy, emboli, heart failure, congenital heart deficit, heart valve disease, arrhythmia, myocarditis, infection, trauma, hypertension, diabetes, chemotherapy, fibrosis, infiltrative diseases, autoimmune diseases, and a side effect of medication, or any combination thereof. In some embodiments, the damaged myocardium is secondary to a chemotherapeutic treatment, optionally a chemotherapeutic treatment that employs an anthracycline or HERCEPTIN®. In some embodiments, the subject had a myocardial infarction prior to the pharmaceutical composition being administered, optionally wherein the subject had at least one myocardial infarction within one year prior to the pharmaceutical composition being administered. In some embodiments, the subject has left ventricle (LV) dysfunction characterized by an ejection fraction (EF) of less than 40%, 45%, or 50%. In some embodiments, the administering results in an increase in has left ventricle ejection fraction (LVEF) of at least 3%, 4%, or 5% within two years post-treatment. In some embodiments, the pharmaceutical composition is administered intracoronarily, transendocardially, transepicardially, and/or as part or in whole on a natural or synthetic biocompatible scaffold and/or matrix that is applied onto and/or within the myocardium of the subject. In some embodiments, the pharmaceutical composition is administered to the subject on at least two separate occasions. In some embodiments, the pharmaceutical composition comprises about $10^6$ to about $10^9$ SSEA3-positive/c-kit-negative CPCs that are also optionally CD34-negative and/or CD45-negative and/or in vitro expanded progeny cells thereof.

The presently disclosed subject matter also provides in some embodiments methods for repairing structure and/or function of damaged and/or poorly functional myocardium in a subject in need thereof. In some embodiments, the presently disclosed methods comprise extracting SSEA3-positive/c-kit-negative cardiac progenitor cells (EA-CPCs) that are also optionally CD34-negative and/or CD45-negative from a subject or an autologous or allogeneic human donor; culturing and optionally expanding the SSEA3-positive/c-kit-negative CPCs that are also optionally CD34-negative and/or CD45-negative; and administering a dose of the extracted, cultured, and optionally expanded autologous or allogeneic cardiac progenitor cells to an area of damaged myocardium in the subject effective to ameliorate the structure and function of the damaged myocardium, ameliorate cardiac scar size, and/or ameliorate arrythmogenic burden in the damaged and/or poorly functional myocardium in the subject. In some embodiments, the extracting step comprises harvesting myocardial tissue comprising the SSEA3-positive/c-kit-negative EA-CPCs that are also optionally CD34-negative and/or CD45-negative from the subject or from the autologous or allogeneic human donor. In some embodiments, the SSEA3-positive/c-kit-negative EA-CPCs that are also optionally CD34-negative and/or CD45-negative are isolated from the biological sample before, after, or concurrently with removing c-kit-positive cells, and the SSEA3-negative cells, and optionally CD34-positive and/or CD45-positive cells. In some embodiments, the SSEA3-positive/c-kit-negative EA-CPCs that are also optionally CD34-negative and/or CD45-negative are administered within and/or to a location in the subject selected from the group consisting of an infarcted region, a border region, a non-infarcted region, a dysfunctional region, and a region of damaged myocardium. In some embodiments, the SSEA3-positive/c-kit-negative EA-CPCs that are also optionally CD34-negative and/or CD45-negative are administered intraarterially, intravenously, transendocardially, epicardially, and/or intracoronarily, optionally via a catheter and/or by injection. In some embodiments, the damaged and/or poorly functional myocardium is a result of a non-ischemic process, optionally wherein the non-ischemic process is selected from the group consisting of hypertensive cardiomyopathy, diabetic cardiomyopathy, chemotherapy induced cardiomyopathy, valvular cardiomyopathy, and idiopathic cardiomyopathy, or any combination thereof. In some embodiments, a dose of the extracted, cultured, and optionally expanded SSEA3-positive/c-kit-negative cardiac progenitor cells (EA-CPCs) that are also optionally CD34-negative and/or CD45-negative that is effective to ameliorate the structure and function of the damaged myocardium is a dose sufficient to form myocardial tissue, decrease scar size, ameliorate fibrosis, form new cardiac vasculature, increase viable cardiac tissue, and/or form one or more coronary vessels in the subject.

The presently disclosed subject matter also provides in some embodiments methods for repairing damaged myocardium in a subject in need thereof. In some embodiments, the presently disclosed methods comprise administering to the subject a pharmaceutical composition as disclosed herein, wherein the structural and/or functional integrity in part or in whole of the damaged myocardium is at least partially restored following administration of the pharmaceutical composition. In some embodiments, the pharmaceutical composition comprises isolated SSEA3-positive/c-kit-negative and optionally CD34-negative and/or CD45-negative post-natal EA-CPCs that are autologous and/or allogeneic to the subject (in some embodiments, a human subject, optionally a pediatric or adult human subject). In some embodiments, the pharmaceutical composition is administered transendocardially, intramyocardially, intracoronarily, and/or transepicardially.

An object of the presently disclosed subject matter having been stated herein above, and which is achieved in whole or in part by the presently disclosed subject matter, other objects will become evident as the description proceeds when taken in connection with the accompanying drawings as best described herein below.

BRIEF DESCRIPTIONS OF THE FIGURES

FIGS. 1A-1F are a series of immunohistochemical and confocal images of sections of human right atrial appendage (RAA) harvested during open heart surgery showing expression of various markers. FIG. 1A is a series of immunohistochemical images showing cells that expressed SSEA3 detected with an anti-SSEA3 antibody labeled with fluorescein isothiocyanate (FITC, which fluoresces green; cells indicated with white lines in the upper left panel and the middle of the right panel) and/or c-kit detected with an anti-c-kit antibody labeled with tetramethylrhodamine (TRITC, which fluoresces red; solid white lines in the lower left panel and in the upper right section of the right panel) within the native human myocardium. Cellular nuclei were stained with 4',6-diamidino-2-phenylindole (DAPI), which labels with nuclei blue fluorescence (examples indicated by smaller dotted white lines). FIG. 1B is two immunohistochemical images of SSEA3-positive cells (green; examples indicated by solid white lines) within the interstitium of the human myocardium. Myocytes were identified by alpha sarcomeric actin (aSA) staining with an anti-aSA antibody labeled with TRITC (red; examples indicated by dotted white lines). The scale bar in each panel is 10 μm. Nuclei were stained with DAPI and appear blue (gray in the in black and white photo (B&W); examples circled) in the panels. FIG. 1C is a series of confocal and microscopy images of SSEA3-positive (green or light gray in black and white photo (B&W); top left panel), SSEA4-positive (TRITC; red or gray in B&W; bottom center panel), and c-kit-negative (allophycocyanin (APC); magenta or light gray in B&W; bottom left panel) human myocardium cells. Nuclei were stained with DAPI and appear blue (gray in B&W; top right panel). The transmission panel (top center panel) shows the location of the SSEA3-positive/c-kit-negative cells, which were adjacent to the striated myocytes within the cardiac interstitium/adventitia. The bottom right panel is an overlay of the SSEA3, SSEA4, DAPI, and c-kit staining. The scale bar in each panel is 10 μm. FIG. 1D is a confocal microscopy image showing SSEA3-positive (green or light gray in B&W; examples indicated by solid white arrow) and c-kit-positive (red or gray in B&W; example indicated by dotted white arrow) cells. SSEA3-positive/c-kit-negative cells within this human pediatric RAA tissue specimen are shown as cells that fluoresced green but lacked red fluorescence (indicated with solid circles). Nuclei are shown in blue with DAPI labeling (examples indicated with broken circles). FIG. 1E is a series of confocal images of paraffin-embedded human right atrial tissue similar to those previously shown in FIGS. 1A-1D. SSEA-positive cells fluoresced green (gray in B&W; top left panel), cell nuclei fluoresced blue (gray in B&W; top right panel), SSEA4-positive cells fluoresced red (gray in B&W; bottom left panel), and c-kit-positive cells fluoresced magenta (no fluorescence noted in bottom center panel). The bottom right panel is an overlay of the other five panels. The top center panel is a transmission image. FIG. 1F is an overlay of several confocal images of a pediatric right atrial tissue sample stained with antibodies that detect SSEA3 (green), SSEA4 (magenta) and c-kit (red). Nuclei are shown in blue with DAPI staining. An SSEA3-negative/c-kit-positive cell is circled. SSEA-3 positivity in green is overlayed by co-SSEA-4 positivity in magenta. The combined hue is illustrated by a pink color indicating double positivity for SSEA3 and SSEA4, examples of which are boxed. These cells did not express c-kit as shown by a lack of red coloration.

FIG. 2 outlines an exemplary methodology for isolated and analyzing right atrial appendage (RAA) samples. The top left image is a typical open heart surgery in which the RAA sample is obtained from the site of bypass catheter insertion. This particular RAA (inset upper right corner of top left image) had a weight of 153 mg. The RAA was processed according to an established protocol by being subjected to mechanical and enzymatic digestion for isolation of gross intracardiac cells and eventual immunomagnetic sorting of SSEA3-positive cells for in vitro expansion. The sorting procedure is outlined herein below in FIG. 18A. The exemplary methodology depicts the surgical harvest, mechanical mincing of the tissue with subsequent enzymatic digestion, isolation of unsorted cardiac cells which grow over the course of 10-14 days in vitro, and immunomagnetic sorting for SSEA3-positive cells using a new application of validated, commercially available antibodies.

FIGS. 3A-3C are flow cytometry plots of cells obtained from cardiac tissue. All plots shown in FIGS. 3A-3C were fixed in 4% paraformaldehyde (PFA) prior to blocking and subsequent immunolabeling. FIG. 3A is a flow cytometry plot showing DAPI positive events only (to exclude contaminating red blood cells which did not have nuclei) that were used for analysis in establishing prevalence of SSEA3-positive cells immediately after myocardial processing and digestion shown in FIGS. 3B and 3C as well as in FIG. 4. FIG. 3B is a flow cytometry plot of cells obtained from freshly digested cardiac tissue that were fixed with 4% PFA and stained with an isotype control antibody to establish analysis gates. Gates were set for isotype control false positives not in excess of 1% of the population which is shown on the top panel (P8-P10 gates). Only cells negative for CD45 are shown. FIG. 3C is a flow cytometry plot of cells obtained from freshly digested tissues that were analyzed for presence of SSEA3, c-kit, and CD45 by flow cytometry. CD34-positive/CD45-positive hematopoietic cells were were labeled with monoclonal antibodies coupled with APC. These cells were eliminated from the analysis by selective gating for all APC (i.e., CD34-positive/CD45-positive) cells. Therefore, shown in FIG. 3B are all cells that are DAPI-positive (i.e., nucleated), CD34-negative/CD45-negative (APC-negative). Accordingly, the fraction of resultant cells represents only the non-hematopoietic intrinsic nucleated cardiac cells excluded from the analyses. Shown is the positive labeling of SSEA3-FITC and c-kit-PE (and negative for CD45-APC). SSEA3-positive cells in the P8 gate (boxed in the upper panel) were seen not to possess detectable levels of c-kit expression. The absolute number of SSEA3-positive cells isolated from this particular large right atrial appendage is shown by the P8 gate (i.e., 2,346 cells out of approximately 406,000 cells analyzed; see lower panel).

FIG. 4 is a bar graph showing the results of analyses of twelve (12) human cardiac tissue specimens that were digested as per the method disclosed herein above and analyzed by flow cytometry for the presence of SSEA3-positive/c-kit-negative/CD45-negative cells, expressed as the number of such cells per milligram of right atrial myocardium. The mean numbers of SSEA3-positive/c-kit-negative/CD45-negative cells per milligram of right atrial tissue from 12 separate patients are shown. Patients 1 and 5 were pediatric patients, whereas other patients were adults.

FIGS. 5A and 5B are flow cytometry plots of unsorted in vitro expanded myocardial cells. FIG. 5A is a flow cytometry plot of unsorted in vitro expanded myocardial cells showing isotype control mouse monoclonal IgG antibodies (eBioscience, Inc., San Diego, Calif., United States of America) labeled with e450 (0.2% false positivity by set gating) and isotype control Rat IgM monoclonal antibody (eBioscience, Inc.) labeled with FITC (0.3% false positivity by set gating). Here, the possible presences of CD34 and/or CD45 markers on SSEA3-positive cardiac cells were investigated as an indication that these cells were from bone marrow/hematopoietic origin. FIG. 5B is a flow cytometry plot of unsorted in vitro expanded myocardial cells, with isotypes represented above as in FIG. 5A, showing that CD34-positive/CD45-positive cells constituted approximately 7% (see the P7 gate) and SSEA3-positive cells constituted approximately 28% (see the P8 gate) of the unsorted population 7 days after initial isolation. These SSEA3-positive cells, highlighted by the conservative magenta color gating in the P8 gate, showed no detectable fluorescence for the markers CD34 and CD45. Additionally, the P9 gate showed no double positive cells with respect to set isotype controls. CD34-positive/CD45-double positive cells within the culture remained as contaminants from the original tissue digestion. These cells can be removed with serial media changes and passaging over time as well as with the SSEA3-positive magnetic immunoselection.

FIG. 6 is a representative flow cytometric plot using the MOFLOW® flow cytometry system (Beckman Coulter, Inc., Indianapolis, Ind., United States of America). FIG. 6 shows SSEA3-positive/c-kit negative cells in the R4 gate (1.27% of all cells). Two populations of c-kit-positive cells can be seen, brightly positive in the R3 gate (0.14% of the total cells) and dimly positive in the R6 gate (74.58% of all cells), neither of which were SSEA3-positive. Gate R5 included cells with double positivity for SSEA3 and c-kit 0.64% of all cells) that was not above isotype controls in nearly one million events that were analyzed.

FIGS. 7A and 7B are flow cytometry plots of unsorted 10 day-expanded SSEA3-positive/c-kit-negative myocardial cells showing SSEA3-positive EA-CPCs that were negative for c-kit. In FIG. 7A, c-kit-positive cells appeared in the P4 gate (0.1% of the total cells) with SSEA3-positive/c-kit-negative cells in the P7 gate (24.6% of the total cells; top left gate; top panel). There was no notable SSEA3-positive/c-kit-positive population in the P10 gate above that of the isotype controls. Again, SSEA3-positive cardiac cells did not detectably express c-kit by flow cytometry. FIG. 7B is a series of flow cytometry plots of unsorted 10 day-expanded SSEA3-positive/c-kit-negative myocardial cells stained with an anti-human SSEA3 antibody (eBioscience, Inc. Rat monoclonal IgM) labeled with PE vs. a mouse monoclonal IgG anti-human SSEA4 antibody labeled with FITC (see the top left plot). SSEA3 vs. SSEA1 staining is shown in the top right plot. The color gating of SSEA1-positivity is shown in brown. SSEA1-positive/SSEA3-negative/SSEA4-negative cells were seen in the P12 gate (upper left section) of the bottom left plot. The lower right plot (P16-P18 gates) shows SSEA1 staining on the x-axis and SSEA3 staining on the y-axis.

FIGS. 8A and 8B are flow cytometry plots of 10 day in vitro expanded unsorted myocardial cells. FIG. 8A shows isotype control mouse monoclonal IgM antibodies (R&D Systems, Inc., Minneapolis, Minn., United States of America) labeled with e450 (0.0% false positivity by set gating) and isotype control rat IgM monoclonal antibody (R&D Systems, Inc.) labeled with FITC (0.2% false positivity by set gating). These data are highlighted by the circled area (P7-P9 gates) in the lower portion of the figure. FIG. 8B is a flow cytometry plots of unsorted myocardial cells with isotypes represented as in FIG. 8A, showing SSEA1-positive cells approximated 6.5% (see the P7 gate of the lower panel) and SSEA3-positive cells approximated 8-27% of the unsorted population (depending on the stringency of the gating employed) 7 days after initial isolation. SSEA3-positive cells are shown in the P8 gate).

FIG. 9 is a flow cytometry plot of unsorted myocardial cells showing expression of SSEA3 and CD90. This sorting experiment evaluated the expression of the mesenchymal marker CD90 (Thy-1). FIG. 9 shows SSEA3-positive cells in the P14 and P15 gates. Gating was set for <1.0% false positivity. The P14 gate identified SSEA3-positive/CD90-negative cells (5.2% of the total cells), whereas the P15 gate included a population of SSEA3-positive/CD90-positive cells (16.3% of the total cells).

FIG. 10 is a flow cytometry plots of clinically relevant magnetically-immunoselected (MACS) SSEA3-positive cells showing greater than 85% enrichment of SSEA3-positive cells stained with a PE-labeled anti-SSEA3 antibody after the third passage with negative expression of c-kit (less than 1%; detected with an APC-labeled anti-c-kit antibody) as measured by FACS (left panel). SSEA4-positive cells were also measured by FACS (see the right panel).

FIG. 11 is a flow cytometry plot using the MOFLOW® flow cytometry system (Beckman Coulter, Inc.) to perform SSEA3 vs. c-kit sorting. Representative MOFLOW® system FACS sorting plots of SSEA3-positive EA-CPCs with the horizontal axes corresponding to SSEA3-FITC and the vertical axes corresponding to c-kit-APC. SSEA3-positive/c-kit-negative cells seen in the R4 gate (box with heavy black outline) were isolated by flow sorting and submitted for subsequent PCR analyses as set forth herein below.

FIG. 12 is a series of bar graphs presenting the results of RT-PCR gene expression analyses of SSEA3-positive/c-kit-negative sorted cells (i.e., EA-CPCs) compared to the same human patient's unsorted cells as controls. The horizontal axis is labeled with individual patient identifiers. Each individual patient included an unsorted sample (left bar of each pair) and an EA-CPC sample (SSEA3+c-kit-; right bar of each pair) Bars represent fold increased expression over unsorted cells from the same human patient.

FIG. 13 is a series of bar graphs presenting the results of RT-PCR gene expression analyses of SSEA3-positive/c-kit-negative/SSEA1-negative sorted cells from initial expanded human myocardial cells. The horizontal axis is labeled with individual patient identifiers. Each individual patient included an unsorted sample (left bar of each triad), an SSEA3-positive/SSEA1-positive sample (SSEA3+SSEA1+; center bar), and an SSEA3-positive/SSEA1-negative sample (SSEA3+SSEA1−; right bar of each triad). Bars represent fold increased expression over unsorted cells from the same human patient.

FIG. 14 is a series of bar graphs presenting the results of RT-PCR gene expression analyses of SSEA3-positive/c-kit-negative/CD90-positive and SSEA3-positive/c-kit-negative/CD90-negative cardiac cell subpopulations. The horizontal axes are labeled with individual patient identifiers. Each individual patient included an unsorted sample (left bar of each triad), an SSEA3-positive/CD90-positive sample (SSEA3+CD90+; center bar), and an SSEA3-positive/CD90-negative sample (SSEA3+CD90−; right bar of each triad). Bars represent fold increased expression over unsorted cells from the same human patient.

FIGS. 15A-15D depict the magnetic immunoselection of SSEA3-positive cells. FIG. 15A depicts an exemplary apparatus for magnetic immunoselection utilizing the Miltenyi OCTOMACS™ brand sorting apparatus (Miltenyi Biotec Inc., Auburn, Calif., United States of America) with MS magnetic sorting columns, pre-separation filters, and the magnetic stand. FIG. 15B is a photomicrograph depicting positively selected SSEA3-positive cells 24 hours after MACS enrichment. SSEA3 immunoselection was performed at the end of passage 1 (P1). Accordingly, the picture is of cells that were the founding population of passage 2 (P2). Morphologically, these cells were largely non-spindle shaped, small cells with high nucleus to cytoplasm ratios. This can be seen in FIGS. 15B and 15D described herein below. FIG. 15C is a flow cytometric plot performed following SSEA3 immunomagnetic selection to quantify and validate enrichment employing magnetic immunoselection for SSEA3-positive cells. FIG. 15D depicts confocal microscopy images of MACS-enriched SSEA3-positive cells with flow cytometric analysis shown in FIG. 15C evaluated for SSEA3 expression by immunocytochemistry. SSEA3 positivity is shown in green (light gray in B&W) with DAPI nuclear staining shown in blue (dark gray in B&W; examples indicated with arrows). Two separate fields are shown. The white scale bar in the bottom left corner of the right image is 50 µm.

Figure 18:
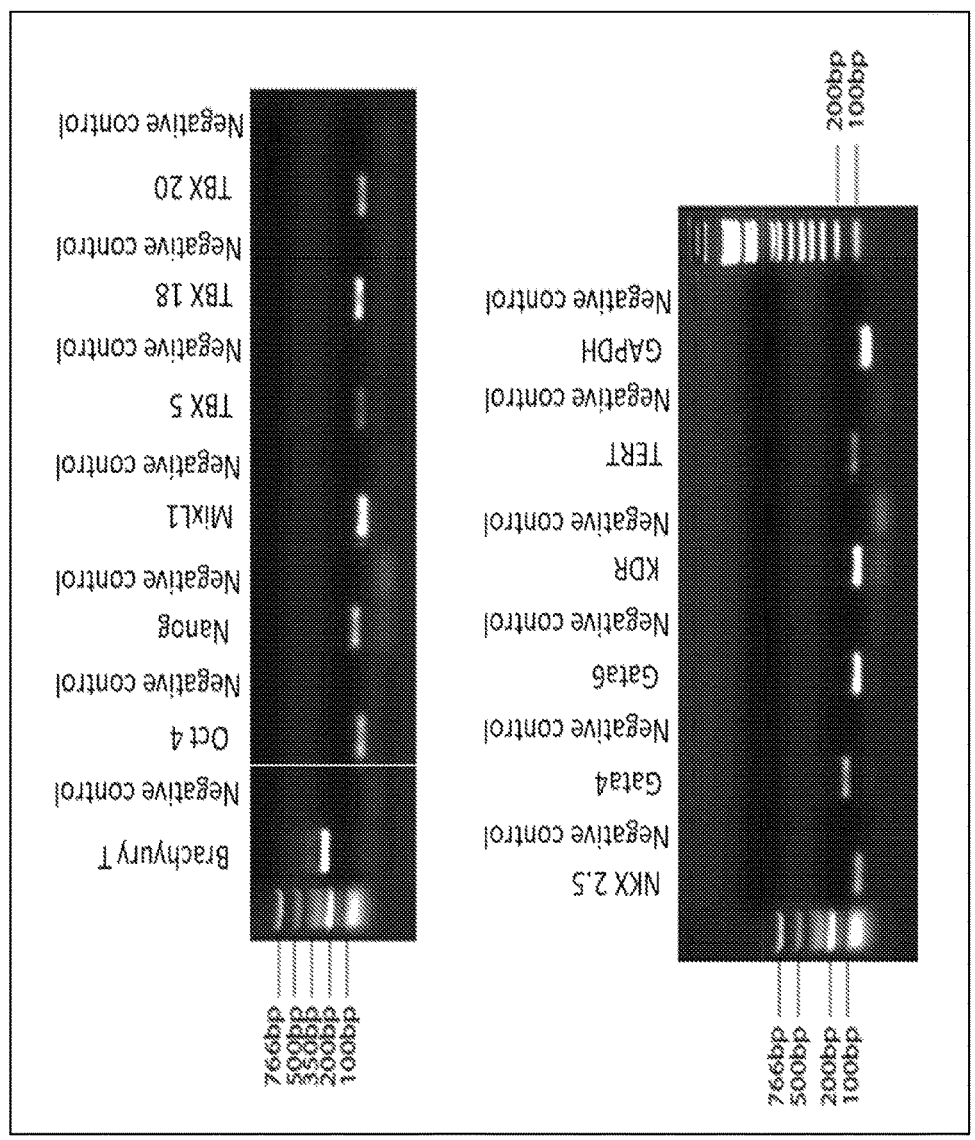

FIG. 18 is a photograph of the results of RT-PCR analysis of were in vitro expanded P3 SSEA3-positive cells immediately after SSEA3 MACS sorting SSEA3-positive cells with respect to the markers BRACHYURY (T). OCT4, NANOG, MIXL1, TBX5, TBX18, TBX20, NKX2.5, GATA4, GATA6, VEGFR2 (KDR), and telomerase (TERT). GAPDH is included as a loading control.

Figure 15A:
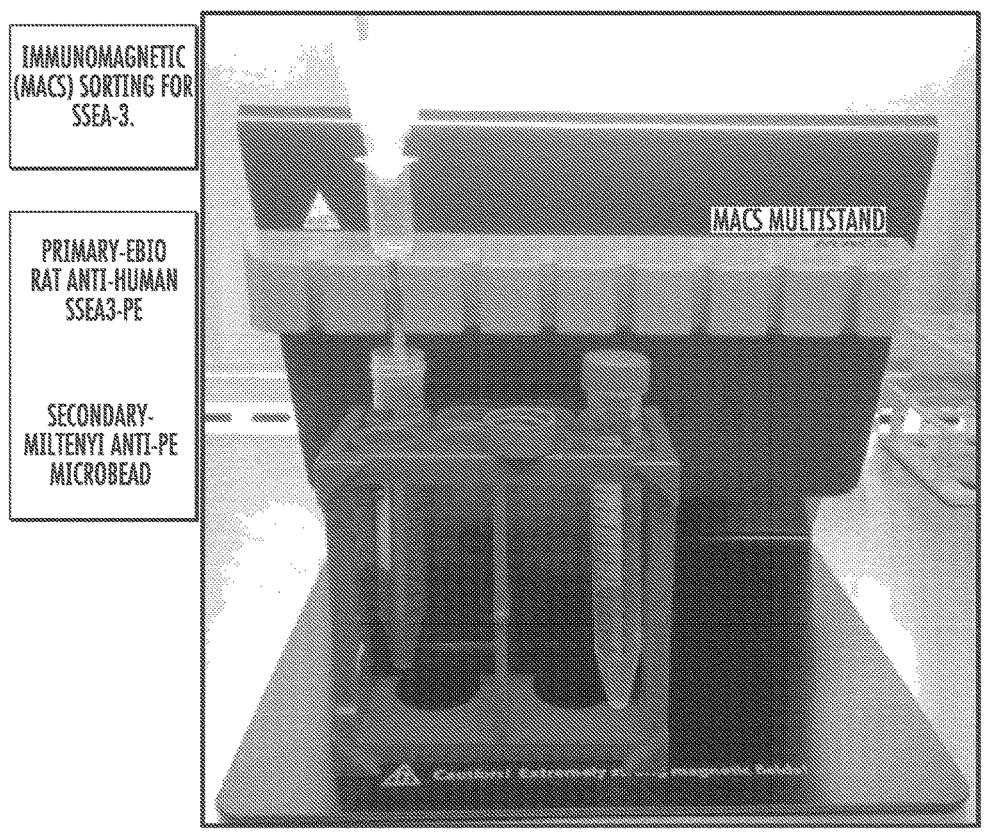
Figure 19A:
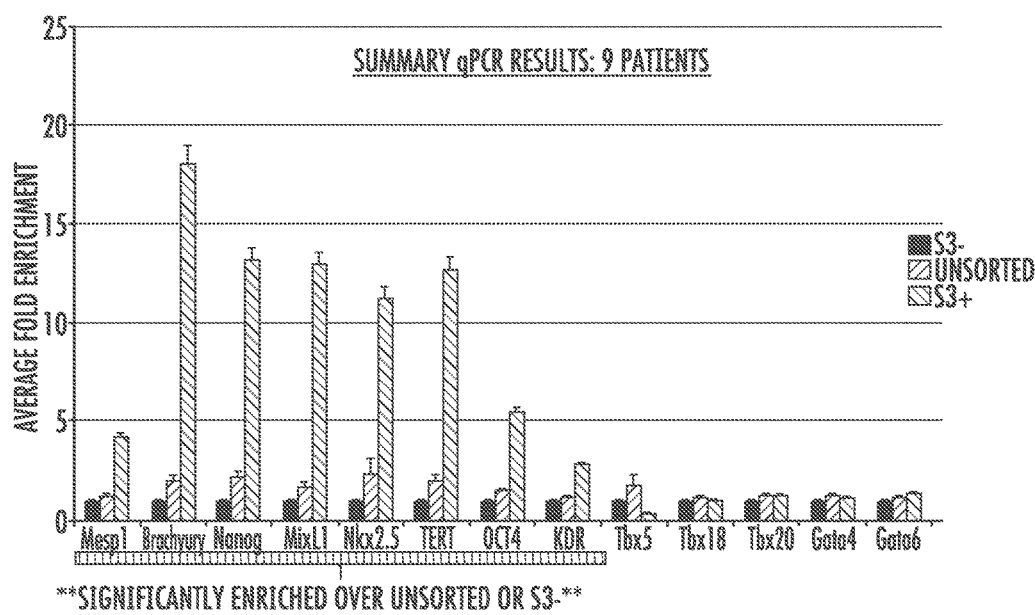
Figure 19B:
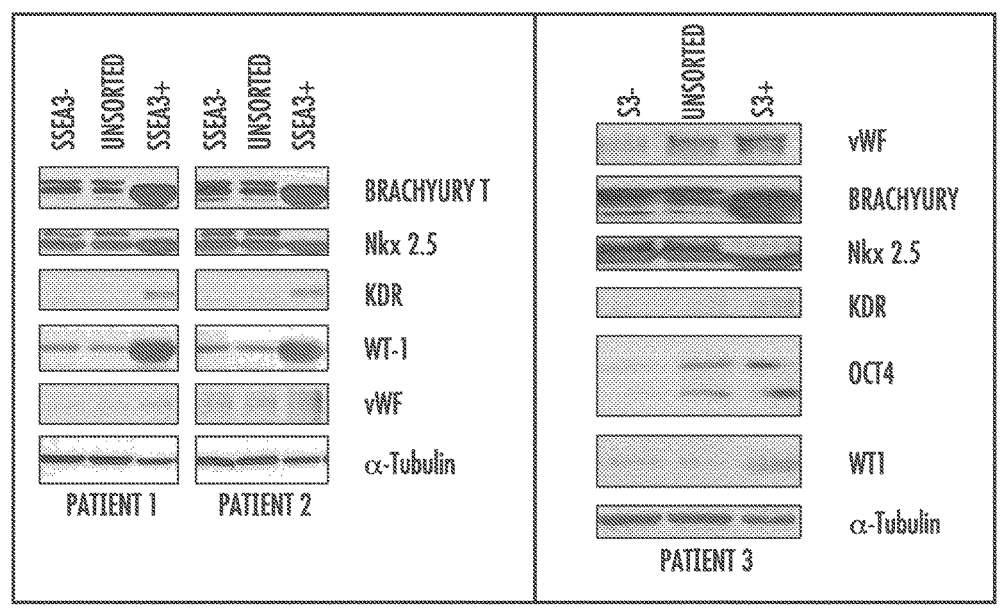
Figure 19C:
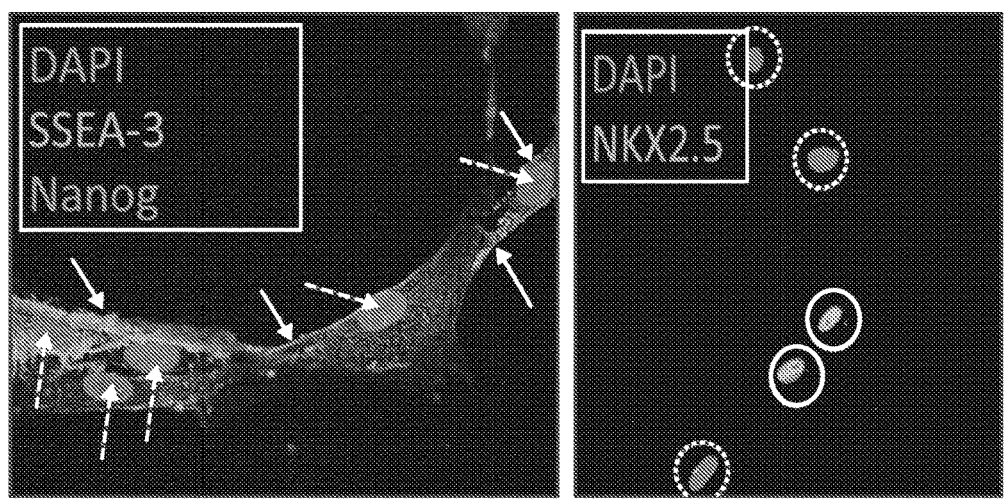

FIGS. 19A-190C depict the analysis of SSEA3-positive cells purified by MACS sorting as outlined in FIG. 15A for various markers. FIG. 19A is a bar graph showing average fold enrichment of the markers (left to right) MESP1, BRACHYURY, NANOG, MIXL1, NKX2.5, TERT, OCT4, KDR, TBX5, TBX18, TBX20, GATA4 and GATA6 in cells isolated from nine (9) human right atrial tissue samples and compared by RT-PCR for relative expression levels. Each marker includes three bars, with the left bar corresponding to SSEA3-negative sorted cells, the center bar corresponding to unsorted cells, and the right bar corresponding to SSEA3-positive sorted cells. FIG. 19B depicts a series of western blot analyses of MACS-sorted SSEA3-negative cells (left lane of each blot), unsorted cardiac cells (center lane of each blot), and MACS-sorted SSEA3-positive cells (right lane of each blot) from three (3) individual patients for the markers BRACHYURY (T), NKX2.5, KDR, WT-1, and vWF to validate protein expression differences corresponding to the RT-PCR analyses shown in FIG. 19A. α-tubulin is included as a loading control. FIG. 19C is a series of confocal microscopy images of SSEA3-positive cells and NANOG-positive cells (green fluorescence; examples indicated by solid white arrows) and red fluorescent stippling (examples indicated by broken white arrows), respectively in the left panel). Shown in the right panel are NKX2.5-positive cells (light blue; indicated by solid circles). In both the left and right panels, nuclei are stained with DAPI (blue; examples indicated by broken circles in right panel).

Figure 20A:
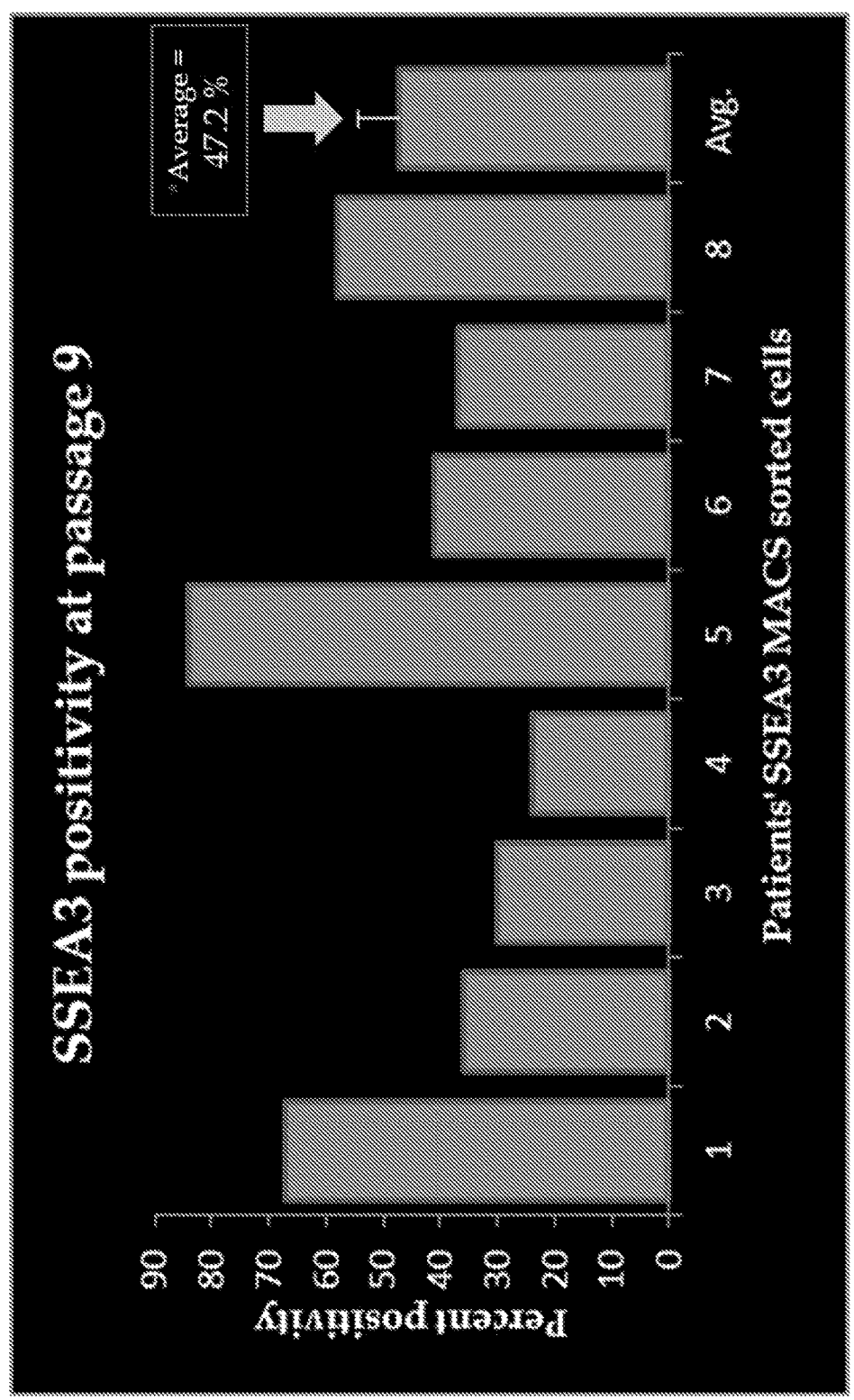
Figure 20B:
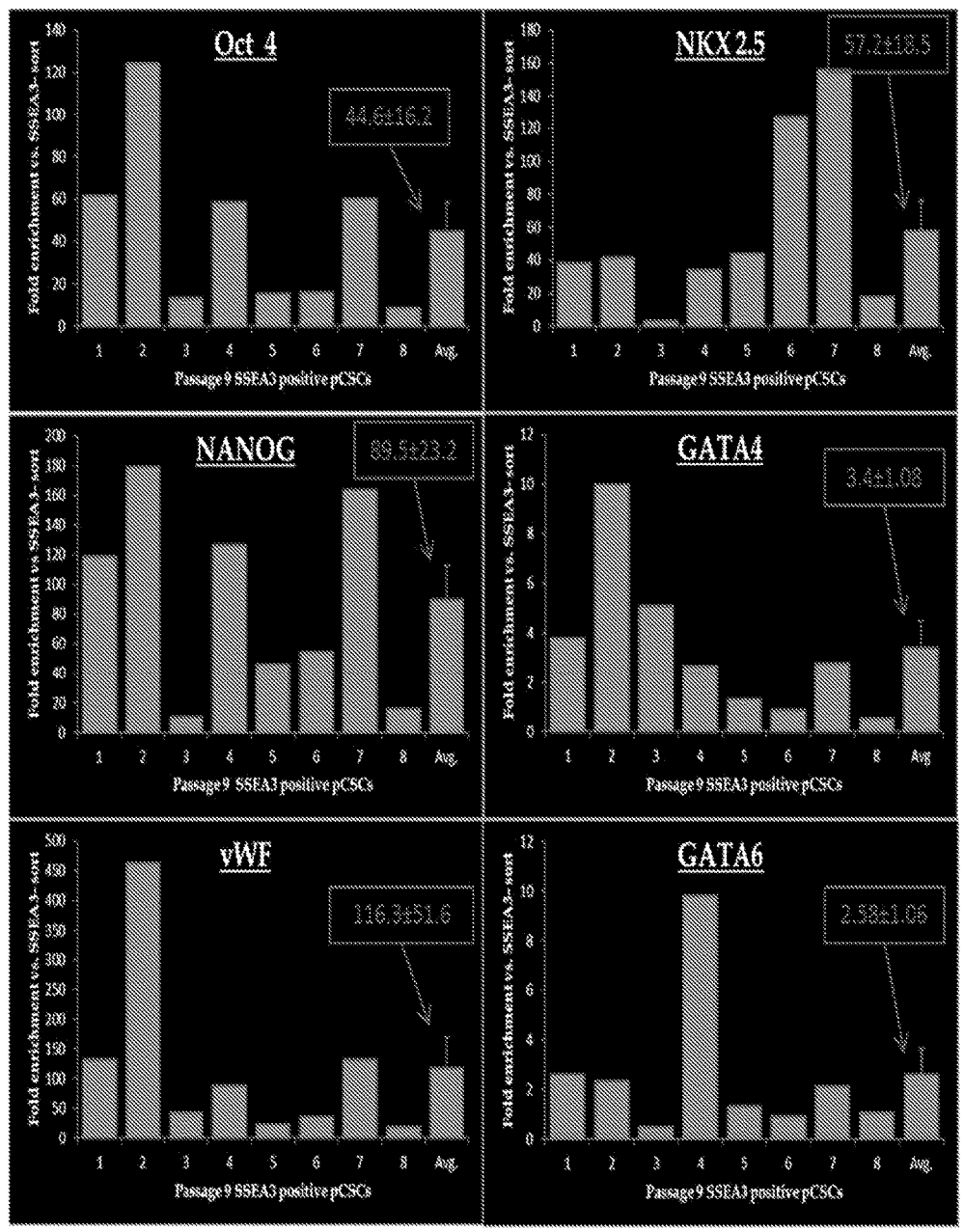

FIGS. 20A and 20B depict the results of further analyses of SSEA3-positive cells isolated by MACS sorting as shown in FIG. 15A. FIG. 20A is a bar graph showing percent SSEA3 positivity of cells isolated from eight (8) patients' right atrial tissue samples at passage 9. FIG. 20B is a series of bar graphs showing a comparison of eight (8) patients' SSEA3 positively immunoselected cells (right bar of each pair) compared to the SSEA3-negative cells (left bar of each pair) after 9 passages by real time polymerase chain reaction (RT-PCR) for the markers GATA4, GATA6, NANOG, NKX2.5, OCT4, and vWF. The y-axis is fold enrichment.

Figure 21A:
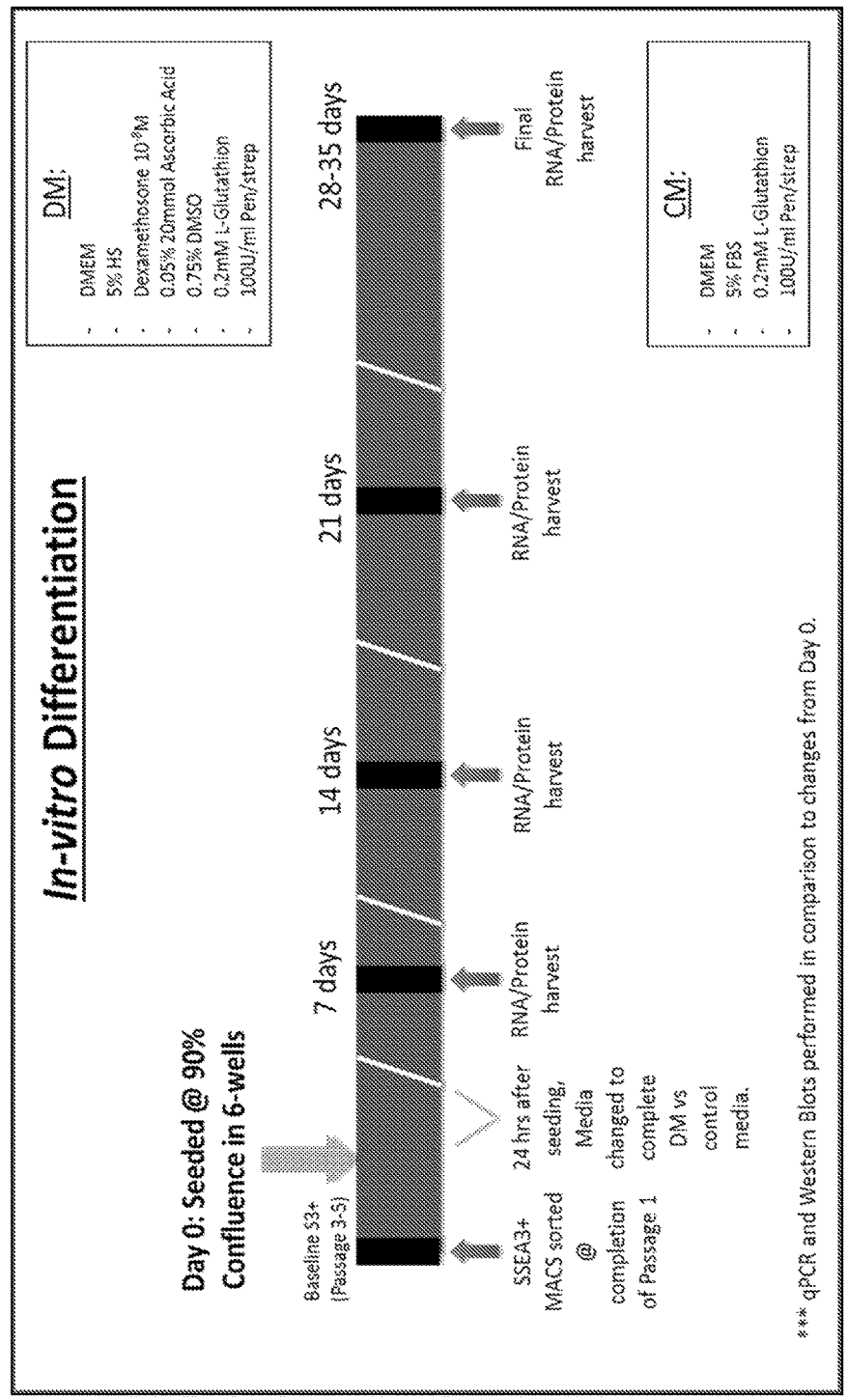
Figure 21B:
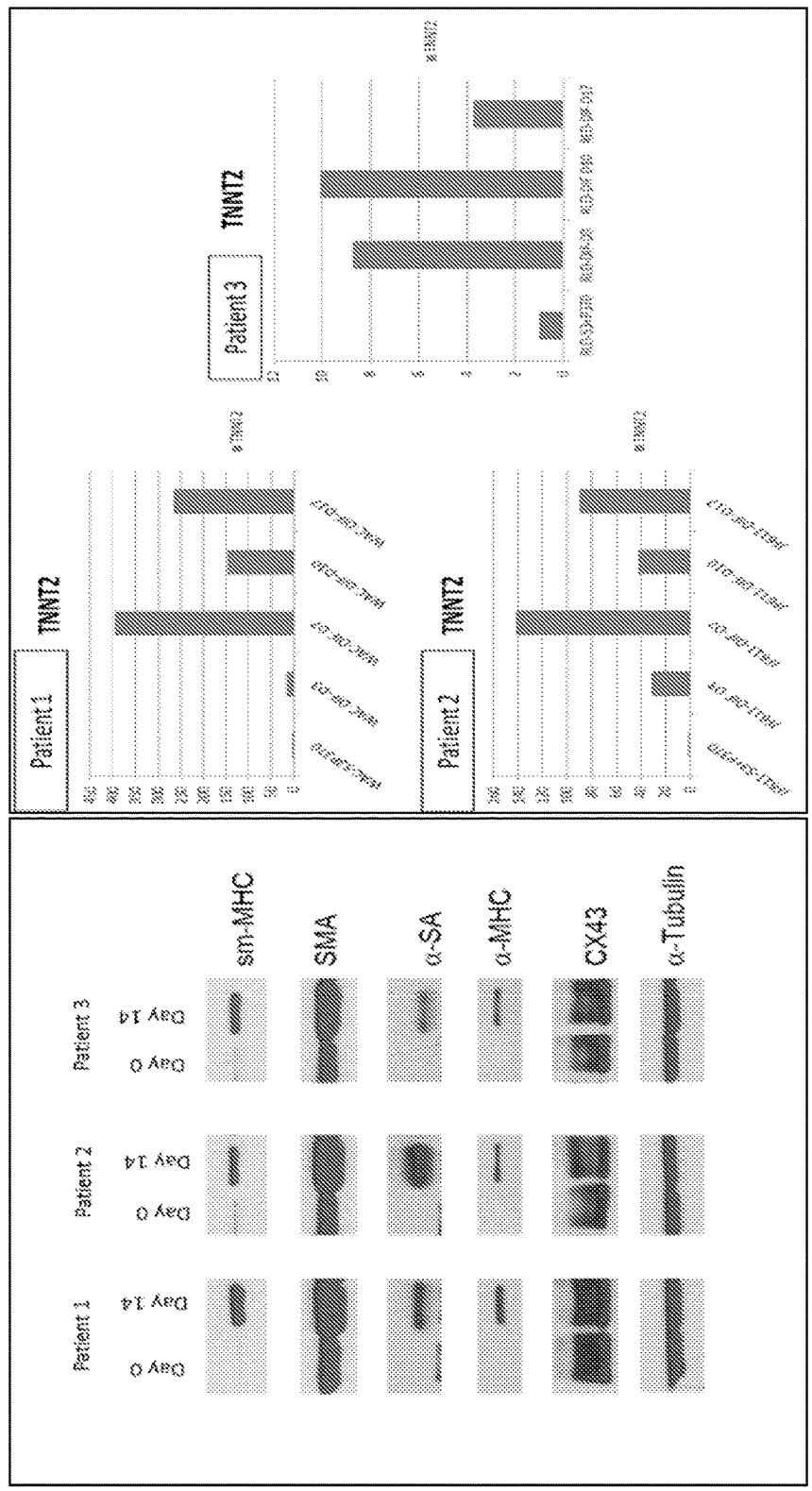
Figure 21C:
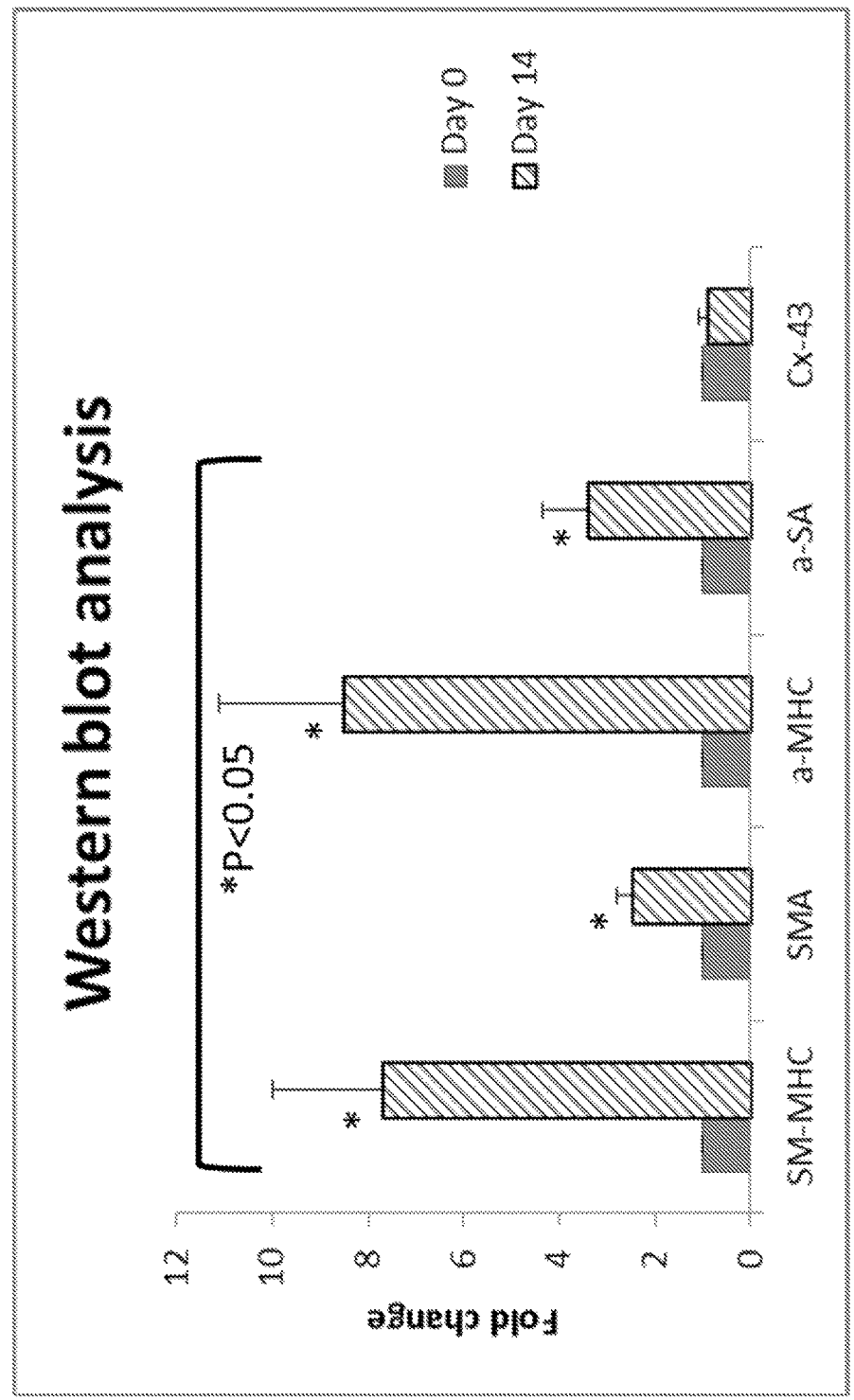
Figure 21D:
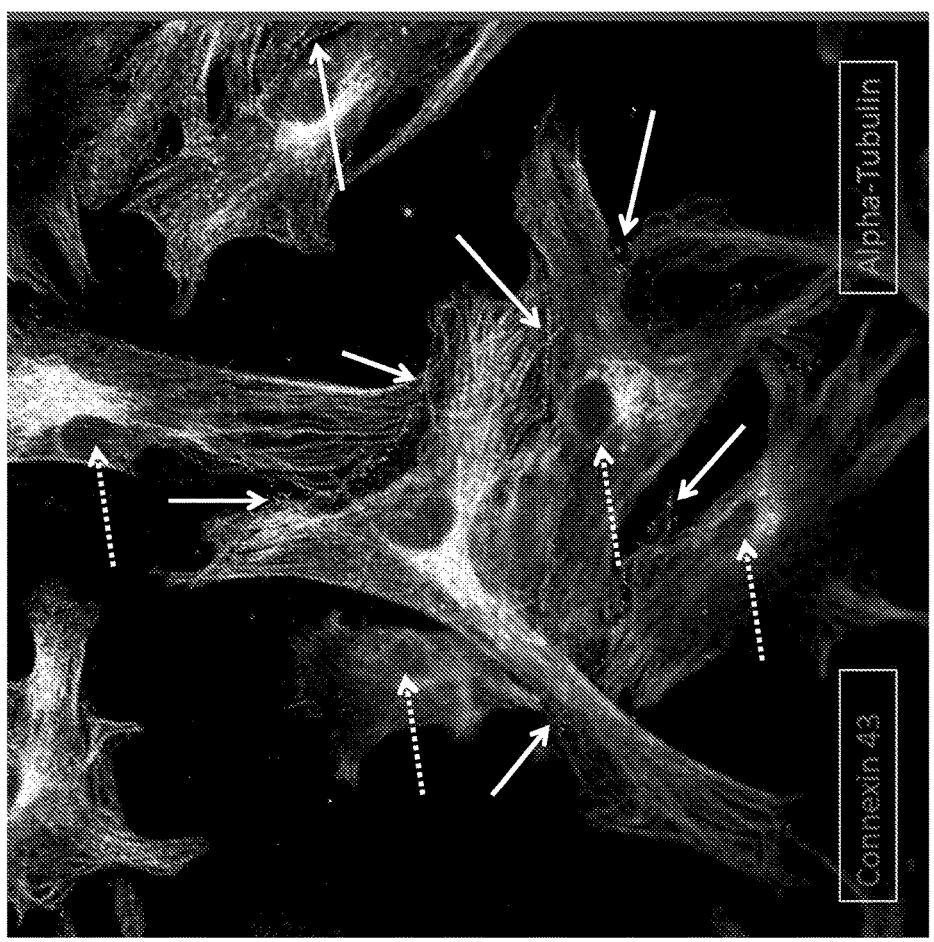
Figure 21E:
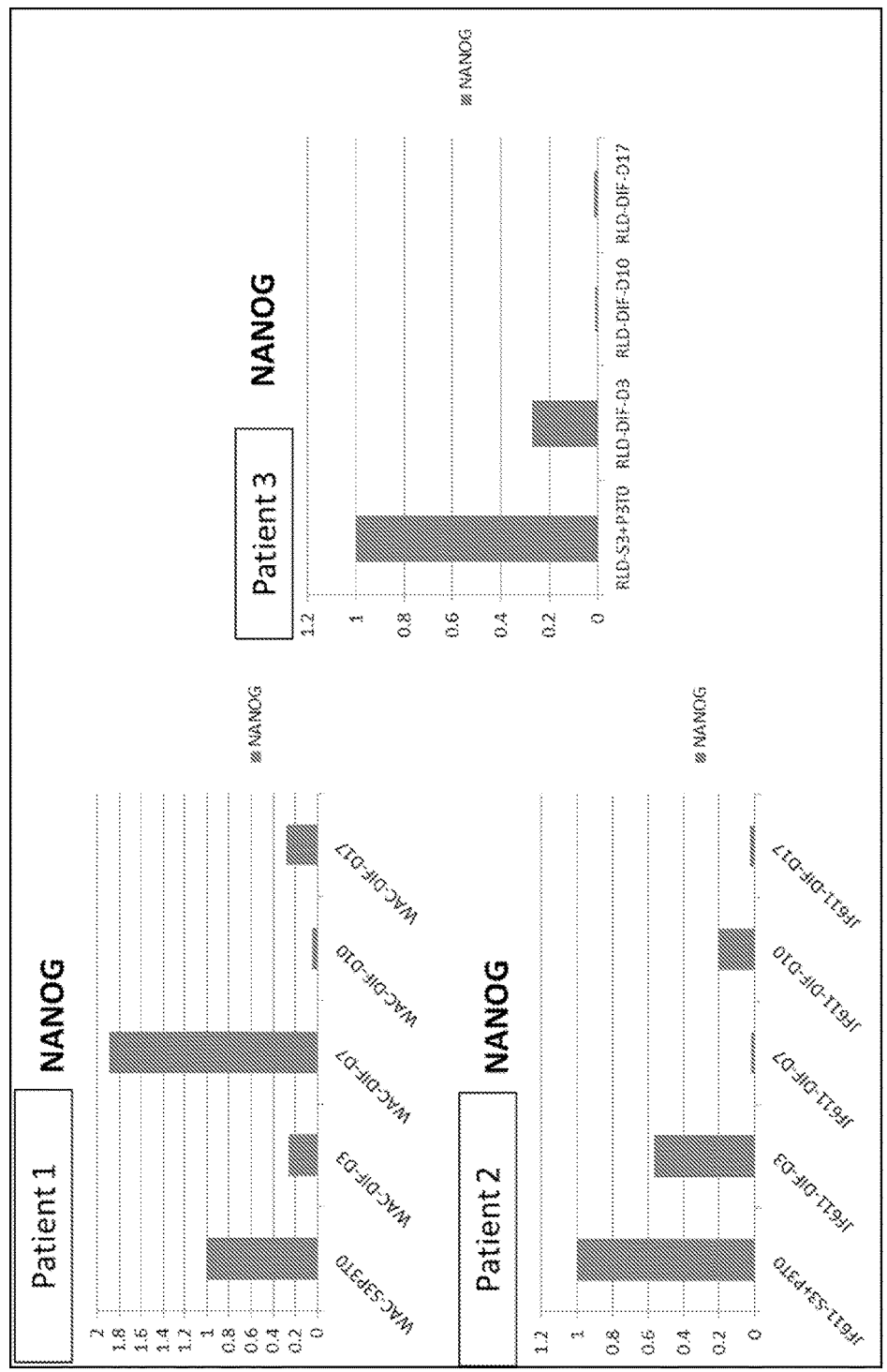

FIG. 21A-21E show an exemplary strategy for in vitro differentiation of SSEA3-positive MACS-sorted cells and a summary of the results thereof. FIG. 21A shows an exemplary strategy and timeline for in vitro differentiation of SSEA3-positive MACS-sorted cells. This exemplary strategy and timeline is discussed in more detail in EXAMPLE 8 herein below. FIG. 21B is a series of western blots (left panel) and a series of bar graphs (right panel) of in vitro differentiated SSEA3-positive MACS-sorted cells at days 0 and 14 after seeding. In the western blots of the left panel, expression of smooth muscle myosin heavy chain (sm-MHC), smooth muscle actin (SMA), alpha myosin heavy chain (α-MHC), alpha myosin heavy chain (α-MHC), alpha sarcomeric actin (α-SA), and connexin 43 (CX43) were assayed. α-Tubulin was included as a loading control. The bar graphs in the right panel of FIG. 21B provide fold enrichments of Troponin T (TNNT2) as measured by RT-PCR. For each of the three bar graphs, fold enrichment of expression of TNNT2 is presented at day 0, 3, 7, 10, and 17 from left to right. A bar graph depicting fold changes in expression from day 0 (solid bars) to day 14 (hatched bars) for these markers is presented as FIG. 21C, with statistically significant increases ($p<0.05$) of expression at day 14 indicated with asterisks. FIG. 21D depicts an exemplary confocal microscopy image of human SSEA3-positive EA-CPCs after differentiation. Alpha tubulin expression is shown in green (white in B&W), connexin 43 expression is shown in red (gray stippling in B&W; examples indicated with solid white arrows), and nuclei are labeled with DAPI staining in blue (examples indicated with broken white arrows). FIG. 21E is a series of bar graphs showing fold enrichment of NANOG expression assayed by RT-PCR during the time course of SSEA3-positive EA-CPC differentiation of the three (3) patients. For each of the three bar graphs, fold enrichment of expression of NANOG is presented at day 0, 3, 7, 10, and 17 from left to right.

Figure 22A:
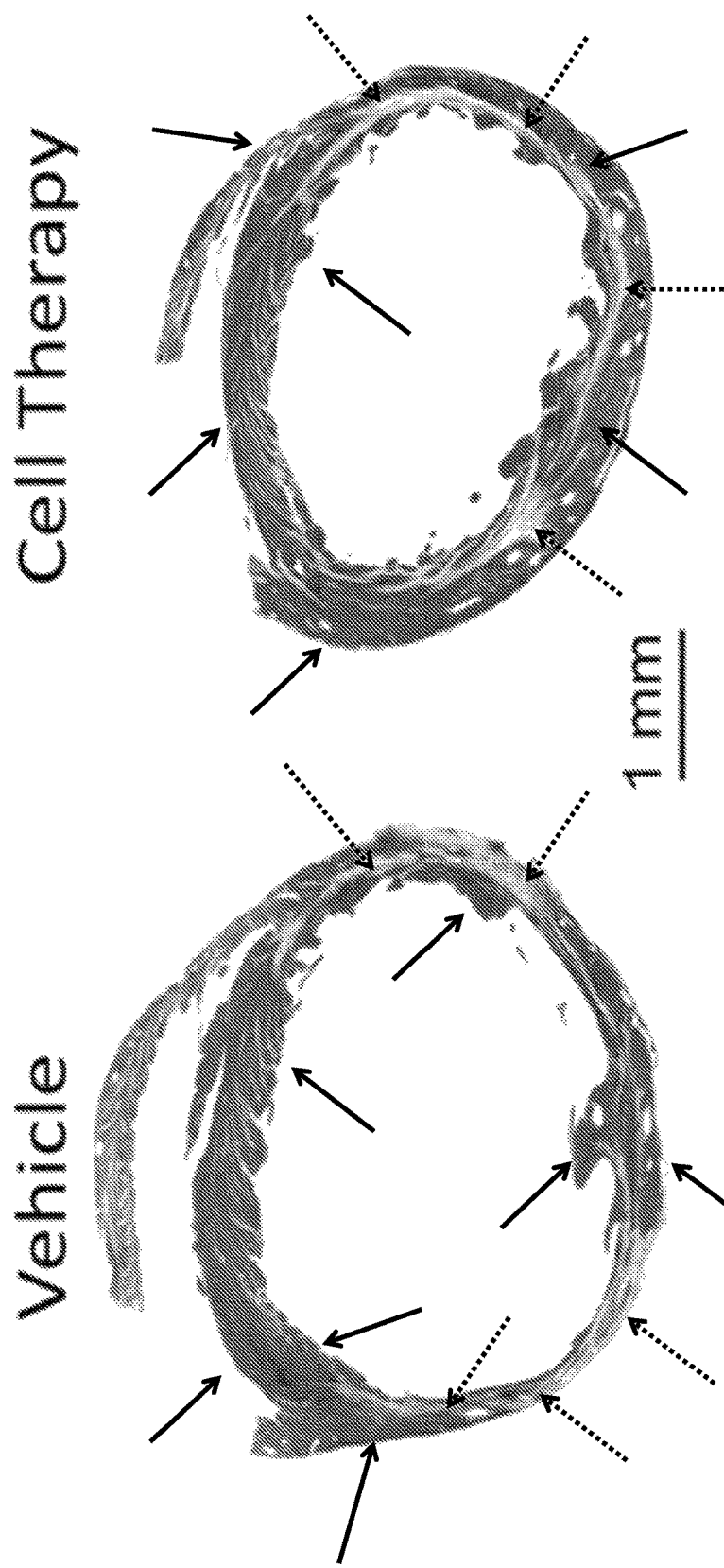
Figure 22B:
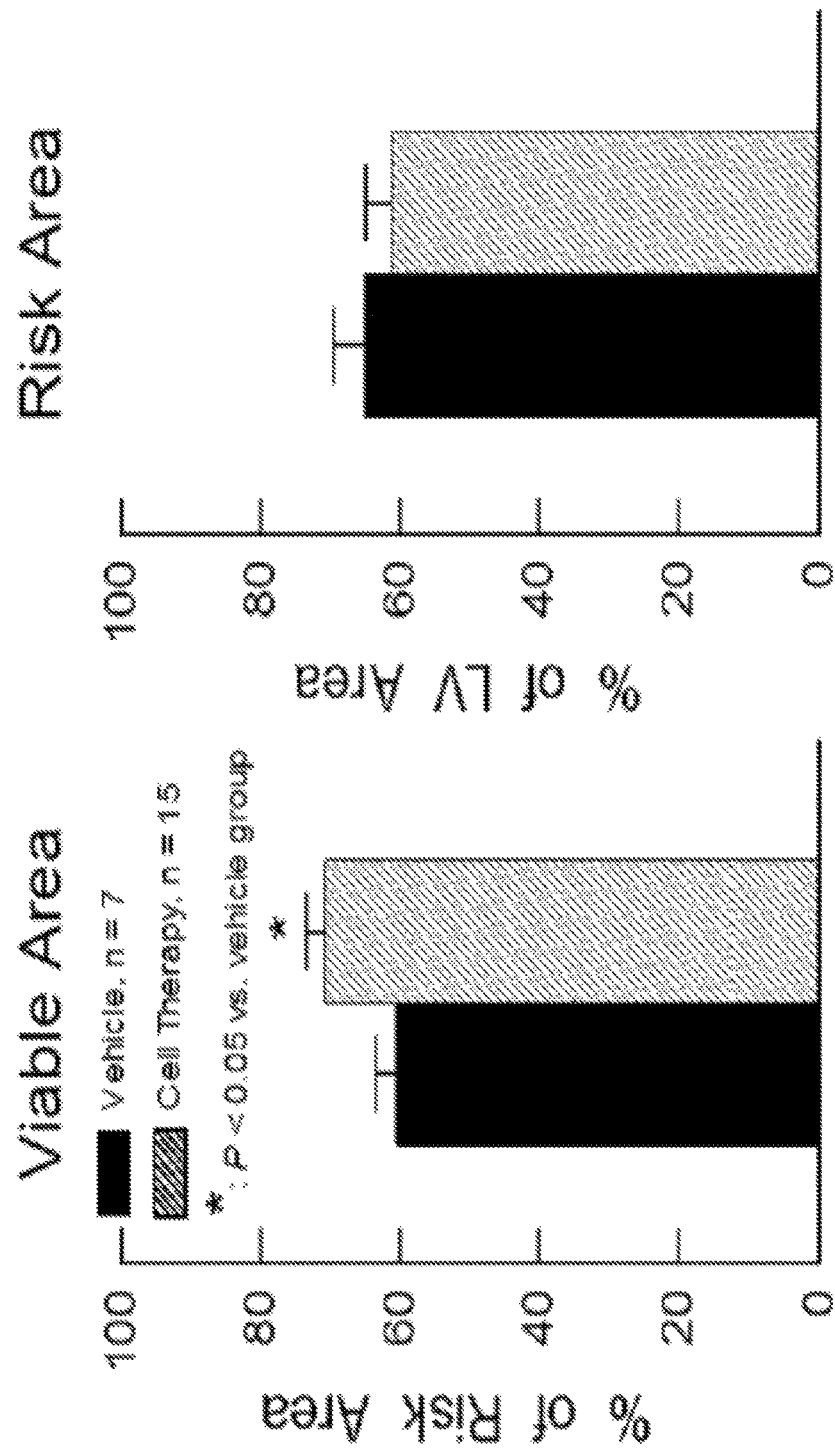
Figure 22C:
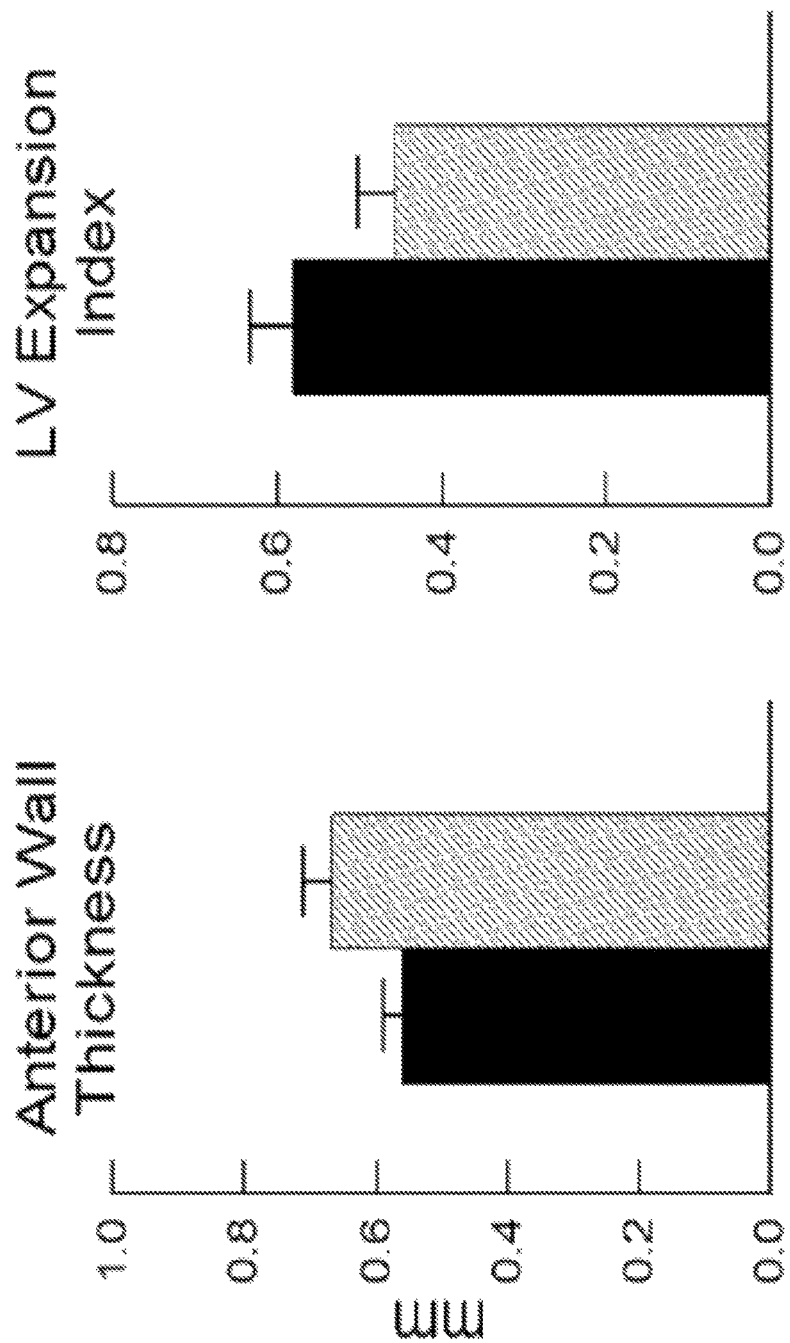

FIGS. 22A-22C summarize assessments of murine myocardial samples after administration of EA-CPCs of the presently disclosed subject matter subsequent to ischemia/reperfusion (I/R) injury. FIG. 22A shows representative Trichrome stains of the murine myocardial sample in cross section in the SSEA3-positive cardiac progenitor cell (EA-CPC) treatment group ("Cell Therapy"; right panel) vs. the control group ("Vehicle"; left panel). The red areas (darker gray in B&W; examples indicated with solid arrows) shown indicate viable myocardial tissue. The blue areas (lighter gray in B&W; examples indicated with solid arrows) within the myocardial wall highlight scar caused by ischemic injury. There was also less scarring seen in the EA-CPC treatment group compared to controls, again shown by the blue (lighter gray in B&W; examples indicated with solid arrows) demarcation within the tissue sections. FIG. 22B is a series of bar graphs comparing viable tissue area (left panel) relative to area of myocardium at risk (right panel) in vehicle (black bars) vs. EA-CPC treatment group (gray bars), with a statistically significant increase in viable area ($p<0.05$) being seen in the EA-CPC treatment group (see the left panel). The area or amount of myocardium at risk was equal between groups (see the right panel). FIG. 22C is a series of bar graphs comparing anterior wall thickness (left panel) and left ventricle (LV) expansion index (right panel) in in vehicle (black bars) vs. EA-CPC treatment group (gray bars).

Figure 23A:
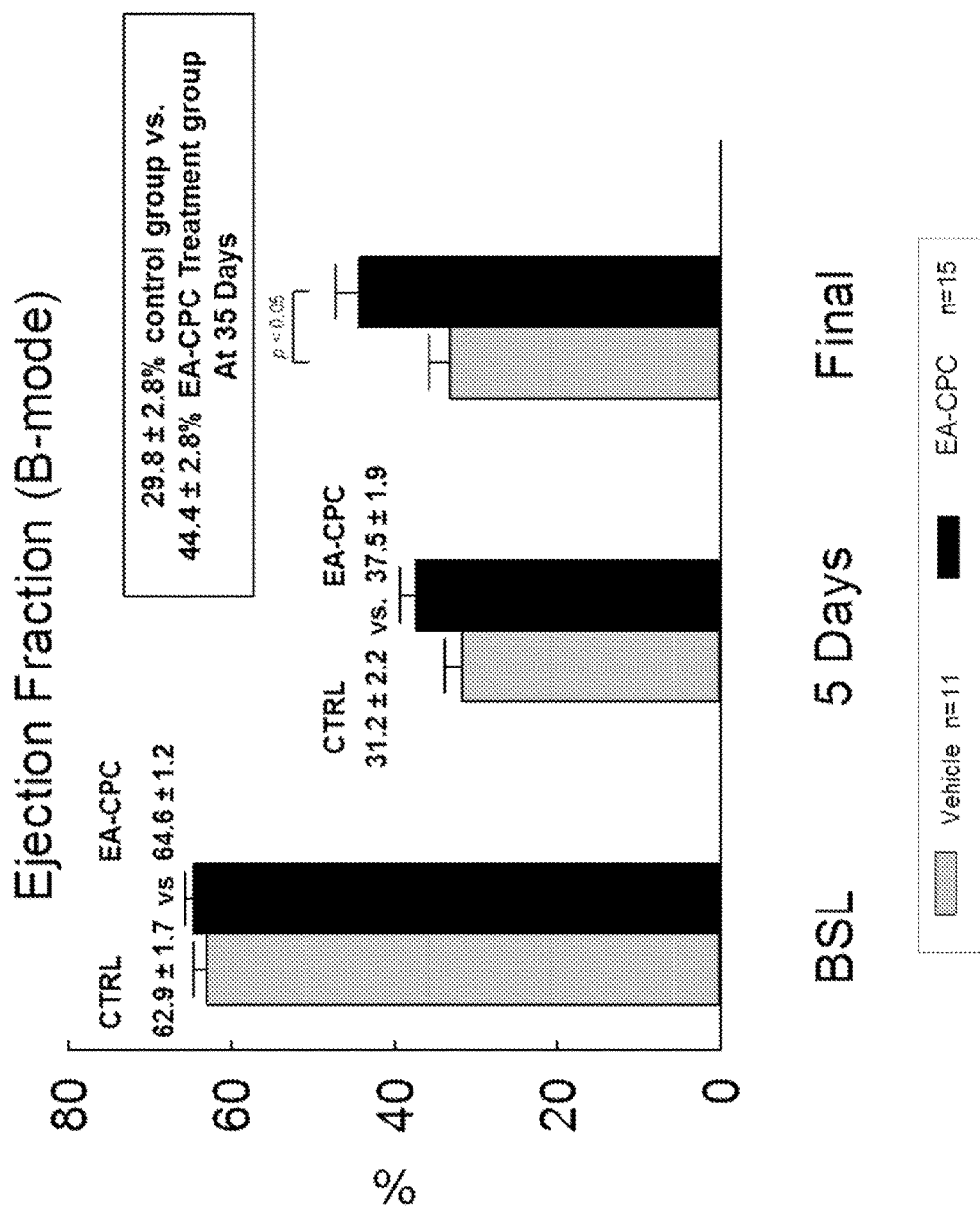
Figure 23B:
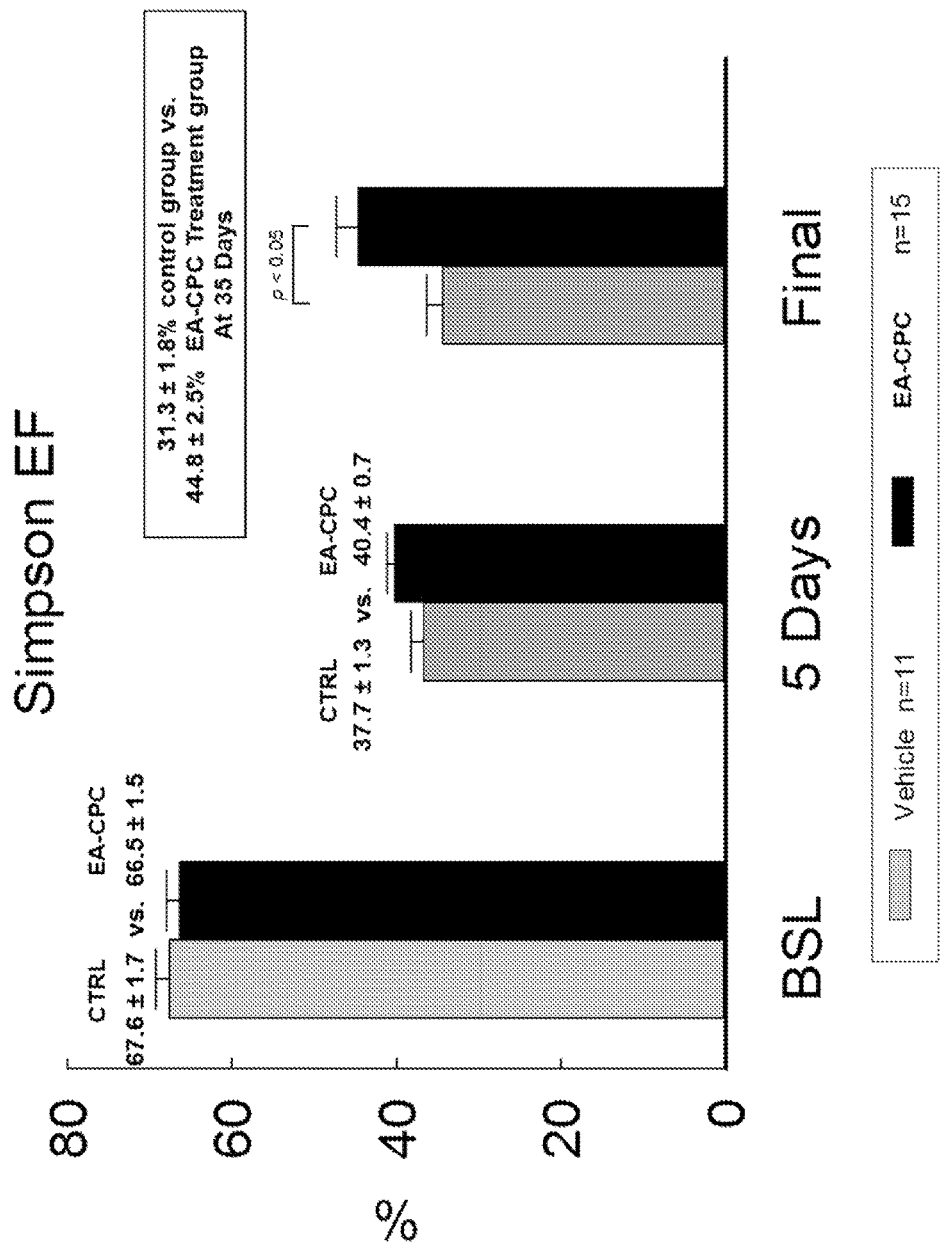

FIGS. 23A and 23B are a series of bar graphs summarizing various parameters associated with cardiac function in EA-CPC-treated (black bars) vs. untreated (gray bars) mice subjected to ischemia/reperfusion (I/R) injury. FIG. 23A is a bar graph comparing ejection fraction (B-mode) in untreated (gray bars) vs. treated (black bars) mice at baseline (BSL), 5 days, and 35 days (Final). FIG. 23B is a bar graph comparing ejection fraction assessed by Simpson's method in untreated (gray bars) vs. treated (black bars) mice at baseline (BSL), 5 days, and 35 days (Final).

DETAILED DESCRIPTION

I. General Considerations

Disclosed herein is the isolation from heart tissue of a novel subpopulation of resident SSEA3-positive/c-kit-negative cardiac progenitor cells (CPCs). In some embodiments, the novel subpopulation of resident CPCs is isolated from one or more of atrial appendages, endomyocardial biopsies, and ventricular biopsies. This subpopulation of CPCs is referred to herein as Embryonic Antigen-positive CPCs (EA-CPCs).

Thus, embodiments of the presently disclosed subject matter are based on the observation that heart tissue comprises a particular population of cardiac progenitor cells, which when freshly isolated are positive for expression of SSEA3 (i.e., are SSEA3-positive), are negative for expression of c-kit (i.e., are c-kit-negative), in some embodiments are negative for expression of CD34 (CD34-negative), and in some embodiments negative for expression of CD45 (CD45-negative). Thus, the EA-CPCs of the presently disclosed subject matter are in some embodiments SSEA3-positive/c-kit-negative, in some embodiments SSEA3-positive/c-kit-negative/CD34-negative, in some embodiments are SSEA3-positive/c-kit-negative/CD45-negative, and in some embodiments are SSEA3-positive/c-kit-negative/CD34-negative/CD45-negative.

More particularly, the EA-CPC population of the presently disclosed subject matter is characterized by the absence of expression of c-kit, which differentiates the presently disclosed EA-CPC population from cardiac stem cells that have been previously identified in heart tissue (see e.g., Beltrami et al. 2003; Bearzi et al., 2007). Furthermore, the absence of expression of c-kit and CD45 differentiate the EA-CPC population of the presently disclosed subject matter from hematopoietic stem cells.

The EA-CPC population disclosed herein has been further characterized in that it is capable of differentiating into cardiomyocytes that express cardiomyocyte marker genes and show sarcomeric protein expression.

Native immunohistochemical characterization showed the presently disclosed population of EA-CPCs to reside in the adult human heart. Cell surface characterization showed positivity for the embryonic stem cell markers SSEA3 and, in some embodiments, SSEA4. Flow cytometric analyses demonstrated that these cells were not mobilized bone marrow cells and were distinct from previously described resident c-kit-positive cardiac stem cells. Transcriptional characterization demonstrated positive expression of transcription factors associated with embryonic stem (ES) cells. Functional analysis showed that these cells were true cardiac progenitor cells and were able to differentiate in to cardiomyocytes as shown by RT-PCR, western blot, immunocytochemistry, and immunohistochemistry.

The cells of the subpopulation of EA-CPCs disclosed herein expressed SSEA3 on their membranes. In some embodiments, they were negative for CD34, the panhematopoietic marker CD45, and other hematopoietic markers including, but not limited to CD3, CD4, CD19, CD20, and CD56.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Furthermore, the terms first, second, third, and the like as used herein are employed for distinguishing between similar elements and not necessarily for describing a sequential or chronological order. It is to be understood that the terms so used are interchangeable under appropriate circumstances and that the subject matter described herein is capable of operation in other sequences than described or illustrated herein.

Following long-standing patent law convention, the articles "a", "an", and "the" refer to "one or more" when used in this application, including in the claims. For example, the phrase "a symptom" refers to one or more symptoms. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the team "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, the phrase "biological sample" refers to a sample isolated from a subject (e.g., a biopsy) or from a cell or tissue from a subject (e.g., RNA and/or DNA and/or a protein or polypeptide isolated therefrom). Biological samples can be of any biological tissue or fluid or cells from any organism as well as cells cultured in vitro, such as cell lines and tissue culture cells. Frequently the sample will be a "clinical sample" which is a sample derived from a subject (i.e., a subject undergoing a diagnostic procedure and/or a treatment). Typical clinical samples include, but are not limited to cerebrospinal fluid, serum, plasma, blood, saliva, skin, muscle, olfactory tissue, lacrimal fluid, synovial fluid, nail tissue, hair, feces, urine, a tissue or cell type, and combinations thereof, tissue or fine needle biopsy samples, and cells therefrom. Biological samples can also include sections of tissues, such as frozen sections or formalin fixed sections taken for histological purposes.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter. By way of example and not limitation, a pharmaceutical composition comprising referred to herein as Embyronic Antigen-positive Cardiac Progenitor Cells (EA-CPCs) and/or progeny cells thereof and a pharmaceutically acceptable carrier can also contain other components including, but not limited to other cells and cell types, other carriers and excipients, and any other molecule that might be appropriate for inclusion in the pharmaceutical composition without any limitation.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause; other elements are not excluded from the claim as a whole. By way of example and not limitation, a pharmaceutical composition consisting of EA-CPCs and/or progeny cells thereof and a pharmaceutically acceptable carrier contains no other components besides the EA-CPCS and/or progeny cells thereof and the pharmaceutically acceptable carrier. It is understood that any molecule that is below a reasonable level of detection is considered to be absent.

As used herein, the phrase "consisting essentially of" limits the scope of a claim to the specified materials or steps, plus those that do not materially affect the basic and novel characteristic(s) of the claimed subject matter. By way of example and not limitation, a pharmaceutical composition consisting essentially of EA-CPCs and/or progeny cells thereof and a pharmaceutically acceptable carrier contains the EA-CPCs and/or progeny cells thereof and the pharmaceutically acceptable carrier, but can also include any additional elements that might be present but that does not.

With respect to the terms "comprising", "consisting essentially of", and "consisting of", where one of these three tetras is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

As used herein, the term "isolated" when referring to cells or a cell population refers to cells or a cell population collected from a subject, in some embodiments a mammalian subject, and in some embodiments a human. Typically, collection of the desired cells or cell population is achieved based on detection of one or more cell markers, such as but not limited to antibody-based detection.

As used herein, the term "post-natal" refers to a subject that has been born. As such, "post-natal" refers to newborns, children, teens, and adults. Similarly, the term "post-natal" when referring to a cell, tissue, or organ, or a fraction thereof, refers to the individual from whom the cell, tissue, or organ, or the fraction thereof, was isolated. In some embodiments, a post-natal subject is a pediatric subject, and in some embodiments, a post-natal subject is an adult subject. In some embodiments, a post-natal subject is a human.

As used herein, the term "subject" refers to any organism for which diagnosis and/or prognosis would be desirable. Thus, the term "subject" is in some embodiments a human subject, although it is to be understood that the principles of the presently disclosed subject matter indicate that the presently disclosed subject matter is effective with respect to other species, including mammals, which are intended to be included in the term "subject". Moreover, a mammal is understood to include any mammalian species for which diagnosis, treatment, and/or prophylaxis is desirable, particularly agricultural and domestic mammalian species.

As used herein, the phrase "substantially" refers to a condition wherein in some embodiments no more than 50%, in some embodiments no more than 40%, in some embodiments no more than 30%, in some embodiments no more than 25%, in some embodiments no more than 20%, in some embodiments no more than 15%, in some embodiments no more than 10%, in some embodiments no more than 9%, in some embodiments no more than 8%, in some embodiments no more than 7%, in some embodiments no more than 6%, in some embodiments no more than 5%, in some embodiments no more than 4%, in some embodiments no more than 3%, in some embodiments no more than 2%, in some embodiments no more than 1%, and in some embodiments no more than 0% of the components of a collection of entities does not have a given characteristic.

As used herein, the phrase "cell surface marker" refers not only for a protein expressed on the surface of a cell but also any carbohydrate, lipid, or any other target that is detectable using specific antibodies or any other standard detection method. Typical cell surface markers that can be useful in the presently disclosed subject matter include, but are not limited to, the major histocompatibility complex (MHC); SSEA3; SSEA4; SSEA1; Tra-1-60; Tra-1-81; the clusters of differentiation (CD) antigens CD29, CD34, CD45, CD55, CD73, CD105, CD90, CD117 (c-kit), and CD133; However other cellular markers described herein or known to the skilled person can also be employed.

The phrase "intracellular marker" as used herein refers to any gene or intracellular gene product that is detectable. Examples of intracellular markers include but are not limited to RNA, particularly mRNA derived from the Oct3 and/or Oct4, Nanog, Sox2, aldehyde dehydrogenase (ALDH), and any other loci. Intracellular markers can also include non-nucleic acid biomolecules including but not limited to being proteins, carbohydrates, and lipids.

The phrase "expression of [marker X]" as used herein when referring to a cell indicates that the cell expresses the marker at a level which is sufficient for detection using standard detection methods. Expression of a marker is also referred to as "positively expressing", "+", "positive", or "pos". The terms "not expressing [marker X]" as used herein when referring to a cell indicates that the cell does not express the marker at a level which is sufficient for detection, using standard detection methods. Absence of expression of a marker is also referred to as "negative expression", "−", "negative", and "neg".

For some markers, such as ALDH, expression or absence of expression is often in fact based on comparison with other cells which also express the marker. For these markers determining positive or negative expression is based on a threshold. Methods for determining positive or negative expression based on thresholds are known to the person skilled in the art and typically involve calibrating based on a "negative control". Accordingly, it will be understood that for these markers, reference to positive expression in fact implies "elevated expression compared to negative controls" and "negative expression" in fact refers to "reduced expression compared to positive controls".

When referring to a cell population, reference is made to a population which "expresses [marker X]" where at least 10%, 20%, or 30% or 40%, 50%, or 60% or 70%, 80%, or 90% or 95%, 96%, 97%, 98%, 99%, or even 100% of the cells within the population express the cell markers of interest. By "substantially free" is intended less than about 25%, 20%, 15%, 10%, 9%, 8%, 7%, 6%, 5%, 4%, 3%, 2%, 1%, or even 0% of the cells in the population express the marker of interest.

III. Cardiac Progenitor Cells (CPCs) and Compositions Comprising the Same

In some embodiments, the presently disclosed subject matter relates to a population of cardiac progenitor cells (CPCs), referred to herein as "EA-CPCs", which are characterized by the following features: the cells are positive for expression of SSEA3 (denoted herein as "SSEA3-positive") and negative for expression of c-kit (denoted herein as "c-kit-negative"). Optionally, the EA-CPCs and also negative for expression of CD34 (CD34-negative), negative for expression of CD45 (CD45-negative), or negative for expression of both CD34 and CD45. These cells are further characterized by the ability to differentiate into cardiomyocytes, smooth muscle cells, and vascular endothelial cells under appropriate conditions including, but not limited to being introduced into a subject.

Additionally or alternatively, the cell population of the presently disclosed subject matter can be further characterized by the ability to differentiate into cardiomyocytes in vitro or in vivo. Methods of differentiating progenitor cells into differentiated cells in vitro are known in the art. More particularly and in order to determine the ability to form cardiac cells, EA-CPCs are typically placed in a cardiomyogenic environment. For instance, co-cultivation of the EA-CPCs of the presently disclosed subject matter having the ability to differentiate into cardiomyocytes with cardiac cells will induce the EA-CPCs to differentiate into a cardiac phenotype. The ability of the EA-CPC population of the presently disclosed subject matter to differentiate into cardiomyocytes by being placed in a cardiomyogenic environment without the need for additional differentiation factors is an important advantage in the context of their therapeutic applications. More particularly, the fact that cells differentiated out of the EA-CPC population according to the presently disclosed subject matter have the functional characteristics of cardiomyocytes ensures the therapeutic potential of these cells. The EA-CPC population of the presently disclosed subject matter can be administered to the area of the heart in need of repair, where they are induced by the environment to differentiate into cardiomyocytes, thereby contributing directly to heart repair.

The differentiation into cardiomyocytes can be determined in different ways. Most typically, expression of genes characteristic of cardiac tissue is determined. More particularly, expression of one or more cardiac-specific genes such as α-actinin, myosin heavy chain, NKX2.5, GATA-4, cardiac troponin T, and cardiac troponin I can be determined using standard methodologies based on mRNA and protein-based detection methods such as but not limited to RT-PCR, immunological detection of the proteins expressed (e.g., immunofluorescence). The cardiomyocytes obtainable by differentiation from the EA-CPCs of the presently disclosed subject matter in some embodiments display cardiac-specific cell markers of cardiomyocytes.

Upon expansion (through cultivation ex vivo or in vitro), this population of cells maintains SSEA3 positivity and c-kit-negativity. This population also maintains the ability to differentiate into cardiomyocytes both in vitro and in vivo, as well as smooth muscle and vascular endothelial cells.

Accordingly, in some embodiments the presently disclosed subject matter relates to a population of expanded cardiac progenitor cells obtainable by expansion of the EA-CPC population described herein, which expanded EA-CPC population is positive for SSEA3, negative for c-kit, and which in some embodiments does not express CD34 and/or CD45.

The presently disclosed subject matter also provides compositions, in some embodiments pharmaceutical compositions, comprising the EA-CPC population and/or expanded EA-CPC population described herein. Such compositions can in some embodiments comprise other cell types as well. More particularly, in some embodiments such compositions further comprise one or more cell types selected from the group consisting of non-cardiac-derived SSEA3-positive cells, SSEA4-positive cells, c-kit-positive cardiac stem cells, hematopoietic stem cells (HSCs), mesenchymal stem cells (MSCs), endothelial progenitor cells (EPCs), bone marrow cells (BMCs), aldehyde dehydrogenase positive (ALDH-positive) cells, very small embryonic like cells (VSELs), cardiosphere-derived cells (CDCs), or any combination thereof. A composition of the presently disclosed subject matter can comprise in some embodiments about 20%, in some embodiments about 25%, in some embodiments about 30%, in some embodiments about 35%, in some embodiments about 40%, in some embodiments about 45%, in some embodiments about 50%, in some embodiments about 55%, in some embodiments about 60%, in some embodiments about 65%, in some embodiments about 70%, in some embodiments about 75%, in some embodiments about 80%, in some embodiments about 85%, in some embodiments about 90%, in some embodiments about 95%, in some embodiments about 96%, in some embodiments about 97%, in some embodiments about 98%, in some embodiments about 99%, and in some embodiments about 100% EA-CPCs.

Thus, in some embodiments the presently disclosed subject matter provides a pharmaceutical composition comprising, consisting essentially of, or consisting of isolated EA-CPCs and/or progeny cells thereof and a pharmaceutically acceptable carrier, wherein the EA-CPCs and/or the progeny cells thereof are c-kit-negative and SSEA3-positive. In some embodiments, the c-kit-negative and SSEA3-positive cells are also CD34-negative and/or CD45-negative.

In some embodiments, the EA-CPC population of the presently disclosed subject matter can be isolated from heart tissue. In some embodiments, the EA-CPCs are isolated from myocardium (including but not limited to human myocardium) or are in vitro or ex vivo expanded progeny cells thereof. It is envisioned that tissue from different parts of the heart can be used for the generation of the cell population of the presently disclosed subject matter, such as left and right atrium, left and right ventricle, tricuspid valve, pulmonary valve, mitral valve, aortic valve. Right atrium includes atrial appendage, fossa ovalis, limbus of fossa ovalis, crista terminalis, valve of the inferior vena cava, valve of the coronary sinus. Left atrium includes left atrial appendage. In some embodiments, the cell population of the presently disclosed subject matter is obtained from right atrial appendages, endomyocardial biopsies, and ventricular biopsies.

It is further envisioned that the EA-CPC population of the presently disclosed subject matter can be isolated from mammal heart tissue. In some embodiments, the tissue is human heart tissue. However, isolation of EA-CPCs from heart of primates, livestock, and domestic animals in the context of therapy is also envisioned.

As detailed above, the SSEA3-positive/c-kit-negative EA-CPC population of the presently disclosed subject matter is characterized by a number of features which differentiate them from other cells present in heart tissue. Accordingly, the EA-CPC population can be isolated from heart tissue using a variety of methods based on these features including, but not limited to those described and/or exemplified herein. Thus, in some embodiments the presently disclosed subject matter provides methods for isolating the EA-CPC population of the presently disclosed subject matter or compositions comprising the EA-CPC population of the presently disclosed subject matter from heart tissue, which are based on detecting one or more of the features of the cell population described herein.

The pharmaceutical composition of the presently disclosed subject matter thus comprise, consisting essentially of, or consist of isolated EA-CPCs and/or progeny cells thereof and a pharmaceutically acceptable carrier, wherein the EA-CPCs and/or the progeny cells thereof are c-kit-negative and SSEA3-positive, wherein the concentration of EA-CPCs is about $1\times10^5$ cells/ml to about $1\times10^9$ cells/ml.

The pharmaceutical composition of the presently disclosed subject matter can also further comprise one or more additional cell types, if desired. In some embodiments, the one or more additional cell types are selected from the group consisting of other SSEA3-positive cells, SSEA4-positive cells, c-kit-positive cardiac stem cells, hematopoietic stem cells (HSCs), mesenchymal stem cells (MSCs), endothelial progenitor cells (EPCs), bone marrow cells (BMCs), aldehyde dehydrogenase positive (ALDH-positive) cells, very small embryonic like cells (VSELs), and/or cardiosphere-derived cells (CDCs).

The pharmaceutical compositions of the presently disclosed subject matter can also further comprise one or more growth factors, cytokines, or any combination thereof. Exemplary non-limiting growth factors and cytokines that can be included in the pharmaceutical compositions of the presently disclosed subject matter include, but are not limited to IGF-1, FGF, HGF, SDF-1, VEGF, BMPs, PDGF, G-CSF, GM-CSF, TGF-β, and SCF.

The EA-CPCs of the presently disclosed subject matter can be produced, generated, isolated, enriched, and/or purified using any method that produces, generates, isolates, enriches, and/or purifies c-kit-negative and SSEA3-positive cells from cardiac tissue. In some embodiments, a pharmaceutical composition comprising, consisting essentially of, or consisting of EA-CPCs isolated from a post-natal cardiac tissue sample by a method comprising disrupting a cardiac tissue sample isolated from a post-natal subject to obtain tissue fragments and/or single cells; placing the tissue fragments and/or single cells in culture; culturing the tissue fragments and/or single cells in a culture medium for a time and under conditions sufficient to generate adequate cell numbers for selective sorting of the c-kit-negative and SSEA3-positive cell population (in some embodiments such as, but not limited to about $10^4$-$10^9$ cells); harvesting all or at least a portion of the tissue fragments and/or single cells from the culture, and optionally disrupting the harvested cells to produce a cell suspension, optionally a single cell suspension; purifying a subpopulation of c-kit-negative and SSEA3-positive cells from the cell suspension; and expanding the c-kit-negative and SSEA3-positive cells in culture (in some embodiments on a substrate, which in some embodiments is a solid substrate), whereby EA-CPCs are prepared. In some embodiments, the c-kit-negative and SSEA3-positive EA-CPCs isolated from the cardiac tissue sample are CD34-negative, CD45-negative, or both CD34-negative and CD45-negative. In some embodiments, the cells isolated from the cardiac tissue sample and/or their progeny, either before, after, or both before and after isolation, enrichment, and/or purification are c-kit-negative and SSEA3-positive and optionally CD34-negative and/or CD45-negative.

It is noted that with respect to any of the presently disclosed compositions and methods, in some embodiments the cardiac tissue sample comprises a sufficient number of cells (e.g., at least about $10^4$ cells) such that the culturing step is not necessary and the harvesting step is performed directly on the disrupted tissue fragments and/or single cells.

In some embodiments, the pharmaceutical compositions of the presently disclosed subject matter comprise, consist essentially of, or consist of SSEA3-positive/c-kit-negative EA-CPCs, optionally SSEA3-positive/c-kit-negative EA-CPCs wherein the SSEA3-positive/c-kit-negative EA- CPCs are optionally also CD34-negative and/or CD45-negative, which are isolated from a cardiac tissue sample by a method comprising disrupting a cardiac tissue sample isolated from a human subject to obtain tissue fragments and/or single cells; placing the tissue fragments and/or single cells into culture; culturing the tissue fragments and/or single cells in a culture medium for a time and under conditions sufficient to generate $10^4$-$10^9$ cells; harvesting all or at least a portion of the tissue fragments and/or single cells from the culture, and optionally disrupting the harvested cells to produce a single cell suspension; purifying a subpopulation of SSEA3-positive/c-kit-negative EA-CPCs, which are optionally additionally CD34-negative and/or CD45-negative, from the single cells and/or the single cell suspension; expanding the SSEA3-positive/c-kit-negative EA-CPCs (that are optionally also CD34-negative and/or CD45-negative) in culture for a time and under conditions sufficient to generate adequate numbers of c-kit-negative and SSEA3-positive and optionally CD34-negative and/or CD45-negative cells to be used in a medicament and/or a pharmaceutical composition as disclosed herein; and combining the expanded c-kit-negative and SSEA3-positive and optionally CD34-negative and/or CD45-negative cells with one or more of c-kit-positive CSCs, HSCs, MSCs, EPCs, BMCs, ALDH-positive cells, VSELs, ES cells, and/or CDCs.

Summarily, the cell populations and compositions of the presently disclosed subject matter are envisioned in some embodiments for use as a medicament, more particularly for use in the treatment of heart disease and/or injury as set forth in more detail herein below. Accordingly, the presently disclosed subject matter provides in some embodiments pharmaceutical compositions comprising EA-CPCs, expanded EA-CPCs, and progeny thereof. According to some embodiments of the presently disclosed subject matter, such pharmaceutical compositions are injectable solutions, matrices, or otherwise as described in more detail herein below.

The presently disclosed subject matter also provides in some embodiments scaffolds comprising the EA-CPCs, expanded EA-CPCs, and/or other compositions disclosed herein. Such scaffolds are in some embodiments typically used in the repair of serious heart damage. In some embodiments, scaffolds can vary in consistency and be directly injected with or supplementary to the cell product. Alternatively or in addition, in some embodiments cells can be grown on a scaffold to generate a 3-dimensional cell structure that can be surgically implanted on the surface of the heart thus promoting migration into the myocardium or localized recruitment of endogenous progenitors to the target area, initiating myocardial repair mechanisms. Exemplary scaffolds are known to those of skill in the art and have been shown to incorporate into the myocardium, promote new myocardial tissue formation, and provide aspects of myocardial repair and regeneration. In some embodiments, a scaffold is injected into the myocardium (see e.g., Mewhort et al., 2013) and/or sewn onto the epicardium as a patch (see e.g., Leor et al., 2000).

As such, the cells, cell populations, and compositions of the presently disclosed subject matter can be administered as such or provided on a scaffold. This can be in the form of one or more layers of a flexible, solid matrix that is implanted in its final form such as, but not limited to, impregnated fibrous matrices. In some embodiments, the matrix holds the EA-CPCs in place at a site of injury. Examples of suitable matrices are known in the art and include but are not limited to collagen, polylactic acid, polyglycolic acid, polyurethane, Dacron, MATRIGEL®, fibronectin, laminin, fibrin, gelatin, etc., as well as decellularized human (homologous) tissue. The scaffold can be in some embodiments biodegradable or in some embodiments can be permanent. Typically, permanent scaffolds are used to replace functional parts of the heart (e.g., valves or vessels).

Accordingly, in some embodiments the presently disclosed subject matter relates to scaffolds seeded with the EA-CPCs disclosed herein and methods for seeding scaffolds in vitro which make use of the presently disclosed EA-CPCs. In some embodiments, the EA-CPCs of the presently disclosed subject matter are cultivated in a bioreactor in the presence of the scaffold material using standard techniques. Materials suitable for use as scaffolds are known to those of ordinary skill in the art.

IV. Cell Cultures Comprising EA-CPCs

The presently disclosed subject matter also provides in some embodiments cell cultures comprising a population of SSEA3-positive/c-kit-negative EA-CPCs and/or progeny cells thereof. In some embodiments, at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the population of SSEA3-positive/c-kit-negative EA-CPCs. In some embodiments, at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the SSEA3-positive/c-kit-negative EA-CPCs and/or the progeny cells thereof are also CD34-negative, CD45-negative, or both CD34-negative and CD45-negative. In some embodiments, at least about 75%, in some embodiments at least about 85%, and in some embodiments at least about 95% of the population of cardiac progenitor cells and/or the progeny cells thereof are c-kit-negative and SSEA3-positive. In some embodiments, at least about 10%, in some embodiments at least 50%, in some embodiments at least 75%, in some embodiments at least about 85%, and in some embodiments at least about 95% of the SSEA3-positive/c-kit-negative EA-CPCs and/or the progeny cells thereof are CD34-negative, CD45-negative, or both.

In some embodiments of the presently disclosed cell culture, the c-kit-negative and SSEA3-positive and optionally CD34-negative and/or CD45-negative EA-CPCs and/or the c-kit-negative and SSEA3-positive and optionally CD34-negative and/or CD45-negative progeny cells thereof are maintained as subconfluent in the cell culture. In some embodiments, the c-kit-negative and SSEA3-positive and optionally CD34-negative and/or CD45-negative EA-CPCs and/or the c-kit-negative and SSEA3-positive and optionally CD34-negative and/or CD45-negative progeny cells thereof are always maintained as subconfluent and are passaged prior to becoming confluent on any cell culture vessel in and/or on which they are grown.

The c-kit-negative and SSEA3-positive and optionally CD34-negative and/or CD45-negative EA-CPCs and/or the c-kit-negative and SSEA3-positive and optionally CD34-negative and/or CD45-negative progeny cells thereof can be cultured on and/or in any cell culture vessel and under any culture conditions that are convenient, provided that the overall conditions of the culturing are such that c-kit-negative and SSEA3-positive and optionally CD34-negative and/or CD45-negative EA-CPCs and/or the c-kit-negative and SSEA3-positive and optionally CD34-negative and/or CD45-negative progeny cells thereof can be isolated from the cell culture at any time during the culturing. As such, various culture media and supplements thereto can be employed.

Thus, various cell culture media can be employed, including but not limited to cell culture media based that employ as a media base any of RPMI-1640, Dulbecco's Modified Eagle's Medium (DMEM), etc. In some embodiments, the growth medium is supplemented by culturing over feeder cells (i.e., so-called "conditioned medium") and/or includes one or more supplements such as but not limited to any one of the following or any combination thereof:

an inorganic salt selected from the group consisting of calcium chloride, HEPES, lithium chloride, magnesium chloride, magnesium sulfate, potassium chloride, sodium bicarbonate, sodium chloride, and sodium phosphate (monobasic and/or dibasic);

an amino acid selected from the group consisting of alanine, L-asparagine, L-aspartic acid, L-cysteine, L-cystine, L-glutamic acid, L-glutamine, Glycine, L-histidine, L-isoleucine, L-leucine, L-lysine, L-methionine, L-phenylalanine, L-proline, L-serine, L-threonine, L-tryptophan, L-tyrosine, and L-valine;

a trace mineral selected from the group consisting of ferric nitrate, ferric sulfate, cupric sulfate, zinc sulfate, ammonium metavanadate, mangenous sulfate, nickel (II) sulfate, selenium, sodium meta silicate, tin (II) chloride, molybdic acid, ammonium salt, cadmium chloride, chromium (III) chloride, silver nitrate, aluminum chloride, germanium dioxide, potassium bromide, potassium iodide, sodium fluoride, rubidium chloride, zirconium oxychloride, cobalt (II) chloride, and barium acetate;

a vitamin selected from the group consisting of vitamin C, biotin, vitamin $B_1$, vitamin $B_2$, vitamin $B_5$, vitamin $B_6$, vitamin $B_{12}$, choline, folic acid, i-inositol, niacinamide, or any salt or derivative thereof;

a growth factor selected from the group consisting of GABA, pipecolic acid, bFGF, TGFβ, insulin (optionally human insulin), holo-transferrin (optionally human holo-transferrin, serum albumin (optionally human serum albumin), and glutathione (optionally reduced glutathione);

an energy substrate selected from the group consisting of D-glucose and sodium pyruvate;

a lipid selected from the group consisting of linoleic acid, lipoic acid, arachidonic acid, cholesterol, alpha tocopherol, linolenic acid, myristic acid, oleic acid, palmitic acid, palmitoleic acid, and stearic acid; and/or a component selected from the group consisting of hypoxanthine, phenol red, putrescine, thymidine, β-mercaptoethanol, PLURONIC® F-68 brand co-polymer, TWEEN® 80 brand surfactant, fetal bovine serum, or a serum replacement such as but not limited to GIBCO® KNOCKOUT™ Serum Replacement brand tissue culture medium supplement, BD NU-SERUM™ IV brand tissue culture medium supplement, and THERMO SCIENTIFIC™ HYCLONE™ ADVANCESTEM™ Serum Replacement brand tissue culture medium supplement.

In some embodiments, the cell culture of the presently disclosed subject matter is grown on a solid support. In some embodiments, the support upon which the c-kit-negative and SSEA3-positive and optionally CD34-negative and/or CD45-negative EA-CPCs and/or the c-kit-negative and SSEA3-positive and optionally CD34-negative and/or CD45-negative progeny cells thereof are growing comprises a growth-promoting medium and/or substrate. Exemplary growth-promoting media and/or substrates include but are not limited to poly-lysine, gelatin, MATRIGEL® brand basement membrane matrix, fibronectin, vitronectin, extracellular matrix component(s), scaffolds, and combinations thereof.

In some embodiments, the c-kit-negative and SSEA3-positive and optionally CD34-negative and/or CD45' EA-CPCs and/or the progeny cells thereof express one or more markers of pluripotency or differentiation and/or commitment. In some embodiments, the one or more pluripotency-associated markers are selected from the group consisting of Oct3, Oct4, Nanog, and Sox2, and the c-kit-negative and SSEA3-positive and optionally CD34-negative and/or CD45-negative EA-CPCs and/or the progeny cells thereof express one or more thereof. In some embodiments, the one or more markers of differentiation and/or commitment are cardiac-specific markers, and in some embodiments the cardiac-specific markers are selected from the group consisting of Nkx2.5, Gata4, Mef2c, Isl1, and Gata6. In some embodiments, the c-kit-negative and SSEA3-positive and optionally CD34-negative and/or CD45-negative EA-CPCs and/or the progeny cells thereof may express one or more additional markers selected from the group consisting of SSEA1, CD105, CD73, CD90, CD29, CD44, CD166, SSEA5, ALDH, alkaline phosphatase (AP), Brachyury (T), and MESP1, or any combination thereof.

V. Methods for Preparing and Isolating EA-CPCs

In some embodiments, the presently disclosed subject matter also provides methods for preparing EA-CPCs. In some embodiments, the methods for preparing EA-CPCs comprise disrupting a cardiac tissue sample to obtain tissue fragments and/or single cells; placing the tissue fragments and/or single cells into culture; culturing the tissue fragments and/or single cells in a culture medium for a time and under conditions sufficient to generate a sufficient number of cells for downstream uses (e.g., in some embodiments about $10^4$-$10^9$ cells); harvesting all or at least a portion of the cultured tissue fragments and/or single cells from the culture, and optionally disrupting the harvested cells to produce a cell suspension, which can optionally be a single cell suspension; purifying a subpopulation of c-kit-negative and SSEA3-positive cells, which optionally are also CD34-negative, CD45-negative or both CD34-negative and CD45-negative, from the single cell suspension; expanding the c-kit-negative and SSEA3-positive and optionally CD34-negative and/or CD45-negative cells in culture, whereby EA-CPCs are prepared. In some embodiments, the EA-CPCs so prepared are appropriate for use in the therapeutic methods disclosed herein.

In some embodiments, the presently disclosed subject matter also provides methods for preparing isolated cell populations enriched in cardiac progenitor cells. In some embodiments, the methods comprise (a) disrupting a cardiac tissue sample to obtain tissue fragments and/or single cells; (b) adhering the tissue fragments and/or single cells to a solid support; (c) culturing the adhered tissue fragments and/or single cells in a culture medium for a time and under conditions sufficient to generate a sufficient number of cells for downstream uses (e.g., in some embodiments about $10^4$-$10^9$ cells); (d) harvesting all or at least a portion of the cultured tissue fragments and/or single cells from the solid support, and optionally disrupting the harvested cells to produce a single cell suspension; (e) purifying a subpopulation of c-kit-negative and SSEA3-positive cells from the single cell suspension, optionally wherein the subpopulation is also CD34-negative and/or CD45-negative; and (f) expanding the c-kit-negative and SSEA3-positive and optionally CD34-negative and/or CD45-negative cells in culture on a solid substrate, wherein an isolated cell population enriched in cardiac progenitor cells is prepared.

In some embodiments, the presently disclosed subject matter also provides methods for isolating EA-CPCs. In some embodiments, the methods for isolating EA-CPCs comprise disrupting a cardiac tissue sample isolated from a subject (optionally a post-natal subject and further optionally an adult human subject) to obtain tissue fragments and/or single cells; placing the tissue fragments and/or single cells into culture; culturing the tissue fragments and/or single cells in a culture medium; harvesting all or at least a portion of the tissue fragments and/or single cells from the solid support, and optionally disrupting the harvested cells to produce a cell suspension, optionally a single cell suspension; purifying a subpopulation of c-kit-negative and SSEA3-positive cells from the cell suspension; and expanding the c-kit-negative and SSEA3-positive cells in culture, whereby a population of c-kit-negative and SSEA3-positive cells from a cardiac tissue sample is isolated. In some embodiments, the c-kit-negative and SSEA3-positive cells isolated from the cardiac tissue sample are EA-CPCs.

With respect to these methods (or indeed any of the methods disclosed herein), the disrupting step can comprise in some embodiments subjecting the cardiac tissue sample to enzymatic and/or mechanical dissociation. In some embodiments the disrupting comprises treating the cardiac tissue sample with an enzyme for a time and under conditions sufficient to create a substantially single cell preparation (in some embodiments, a preparation in which at least about 50% of the cells are single cells. In some embodiments, the cardiac tissue sample is obtained from a non-embryonic (i.e., post-natal) cardiac tissue biopsy, optionally a cardiac tissue biopsy from an adult. In some embodiments, the solid support is a tissue culture dish, and optionally wherein the tissue culture dish is coated with a growth-promoting medium selected from the group consisting of poly-lysine, gelatin, MATRIGEL® brand basement membrane matrix, laminin, collagen, an extracellular matrix preparation.

In some embodiments of the presently disclosed preparation and/or isolation methods, the culturing employs any of the culture conditions, methods, and/or compositions disclosed herein above (e.g., in Section IV). In some embodiments, the culturing is in the presence of one or more growth factors such as but not limited to FGF, IGF-1, TGF-β, PDGF, VEGF, SCF, a BMP, or any combination thereof. In some embodiments, the culturing is for about 7 days to about 90 days or more than 90 days. In some embodiments, the isolated stem cells or progenitor cells (e.g., EA-CPCs) are cultured in the presence of additional cells including, but not limited to murine epithelial cells (MEFs) and mesenchymal feeder cells. In some embodiments, feeder cells are not employed for the culturing and/or expansion steps.

Additionally, any method that can be employed for separating cell subpopulations based on marker expression can be employed for preparing and/or isolating the EA-CPCs subpopulation of the presently disclosed subject matter. By way of example and not limitation, a purifying step can comprise Fluorescence-Activated Cell Sorting (FACS) and/or Magnetic Activated Cell Sorting (MACS) using reagents that are specific for SSEA3 and c-kit, and optionally also reagents that are specific for CD34 and/or CD45. As such, in some embodiments the purifying simultaneously or sequentially (i) enriches for a population of SSEA3-positive cells; (ii) removes c-kit-positive cells; and optionally (iii) removes CD34-positive cells, CD45-positive cells, or both, to yield a purified and/or enriched EA-CPCs subpopulation that is enriched for c-kit-negative and SSEA3-positive and optionally CD34-negative and/or CD45-negative cells.

Furthermore, the c-kit-negative and SSEA3-positive and optionally CD34-negative and/or CD45-negative EA-CPCs that are prepared and/or isolated can also be expanded ex vivo or in vitro. Expansion of the c-kit-negative and SSEA3-positive and optionally CD34-negative and/or CD45-negative EA-CPCs can be by any method, including but not limited to placing purified and/or enriched c-kit-negative and SSEA3-positive and optionally CD34-negative and/or CD45-negative EA-CPCs back into culture on or in a cell culture vessel and under conditions described herein for a time and under conditions sufficient to produce however many c-kit-negative and SSEA3-positive and optionally CD34-negative and/or CD45-negative EA-CPCs that might be desired. By way of example and not limitation, the culturing and/or expanding is for at least 3 days with respect to any of the presently disclosed methods. In some embodiments, the culturing and/or expanding is sufficient to produce at least $10^5$ cardiac-derived cells that are c-kit-negative and SSEA3-positive and optionally CD34-negative and/or CD45-negative (i.e., are EA-CPCs).

In order to provide biological materials that can be employed in the methods and compositions of the presently disclosed subject matter, cardiac tissue samples are isolated from subjects. In some embodiments, the cardiac tissue sample comprises tissue and/or cells isolated and/or expanded from cardiac right atrial appendage tissue, left atrial appendage tissue, cardiac ventricular tissue, cardiac valvular tissue, cardiac vascular tissue, and/or endomyocardial biopsy tissue.

As such, an EA-CPC population of the presently disclosed subject matter is characterized, inter alia, by an SSEA3-positive/c-kit-negative phenotype. Accordingly, the cell populations disclosed herein can be isolated from heart tissue using methods that include the detection of expression of SSEA3 and exclude those cells that expression c-kit.

Methods of detecting SSEA3 are known in the art. In some embodiments, SSEA3 expression is detected using a reagent comprising a detectable moiety, wherein the reagent specifically binds to or otherwise interacts with SSEA3 such that the presence of the detectable moiety is indicative of the presence of an SSEA3 gene product. By way of example and not limitation, SSEA3 can be detected using an antibody that is specific for SSEA3, wherein the antibody comprises a detectable label. Exemplary, non-limiting detectable labels include luminescent labels, fluorescent labels, magnetic labels, etc. In some embodiments, the detectable label is a magnetic label or fluorescent label. In some embodiments, the detectable label is conjugated to an antibody (optionally a monoclonal antibody) that specifically binds to SSEA3. Thus, in some embodiments of the presently disclosed subject matter, the EA-CPCs are isolated from heart tissue based on methods that include the detection of SSEA3 expression, which in some embodiments include but are not limited to FACS and/or sorting using magnetic beads (such as but not limited to the CLINIMACS® brand system from Miltenyi Biotec Inc.).

Methods of detecting c-kit are also known in the art. In some embodiments, c-kit expression can be detected using a reagent comprising a detectable moiety, wherein the reagent specifically binds to or otherwise interacts with c-kit such that the presence of the detectable moiety is indicative of the presence of a c-kit gene product. By way of example and not limitation, c-kit can be detected using an antibody that is specific for c-kit, wherein the antibody comprises a detectable label. Exemplary, non-limiting detectable labels include luminescent labels, fluorescent labels, magnetic labels, etc. In some embodiments, the detectable label is a magnetic label or fluorescent label. In some embodiments, the detectable label is conjugated to an antibody (optionally a monoclonal antibody) that specifically binds to c-kit. In some embodiments, cells which express c-kit are removed from a cell population in order to generate a subpopulation of c-kit-negative cells.

Additionally or alternatively, the cell population of the presently disclosed subject matter can be identified and/or selected based on one or more other characterizing features, such as the expression of other cellular markers. More particularly, the freshly isolated EA-CPC population of the presently disclosed subject matter can be identified and/or isolated based on a typical expression pattern of one or more of the following markers: CD34, CD45, CD29, CD105, CD73, CD90, CD117 (c-kit), and CD133. Generalized methods for determining cellular markers and/or selecting cells based on cellular markers are known in the art. Typically, such detection and/or identification methods employ labeled antibodies directed against the cellular marker of interest. Antibody types suitable for such uses can be, but are not limited to, monoclonal, polyclonal, single chain, and/or recombinant antibodies. To detect binding, antibodies are typically bound either directly to a label or to a ligand, magnetic bead, or enzyme. Examples of ligands include but are not limited to biotin, avidin, streptavidin, a fluorophore, and magnetic beads. Typically enzymes include but are not limited to luciferase, peroxidase, and β-galactosidase. Suitable ligands, beads, or enzymes can be selected by a person of ordinary skill in the art.

Typically for separation and/or isolation, cells are either positively or negatively selected with labeled antibodies, such as but not limited to fluorescently labeled antibodies, using flow cytometry, antibodies are linked to magnetic beads for sorting in a magnetic apparatus, or antibodies are linked to a ligand and separated on a column that binds to the ligand. Other suitable known techniques involve antibodies attached to a solid matrix (such as but not limited to plate elutriation).

According to some embodiments, the presently disclosed subject matter provides methods for obtaining a population of EA-CPCs from isolated heart tissue, which cells are characterized in that they are suitable for therapeutic use, which method comprises selecting cells which are SSEA3 and c-kit-negative from said tissue and further comprises selecting cells which are CD34-negative, CD45-negative, and/or SSEA3-positive. Typically, methods for identifying the SSEA-positive/c-kit-negative EA-CPC population of the presently disclosed subject matter comprise the steps of contacting the relevant antibodies to the cellular markers with a cell population and detecting the formation of an antigen/antibody complex. Examples of such detection methods include but are not limited to radioimmunoassay (RIA), enzyme-linked immunosorbent assay (ELISA), immunofluorescence assay, etc.

In some embodiments, the presently disclosed subject matter also provides methods for isolating/selecting the presently disclosed SSEA-positive/c-kit-negative EA-CPC population, the methods comprising contacting a sample comprising the presently disclosed EA-CPCs with one or more antibodies capable of detecting the relevant cellular markers, allowing antigen-antibody complex formation and collecting the antigen-antibody complex (or, in the case of a negative marker, those cells for which there is no antigen/antibody complex formation).

Thus, in some embodiments the presently disclosed subject matter provides methods of obtaining compositions comprising the cardiac progenitor cells referred to herein as EA-CPCs, which methods comprise selecting SSEA3-positive and c-kit-negative cells from isolated heart tissue. The presently disclosed methods generate cell populations in which in some embodiments at least 25%, 40%, 50%, 60%, 70%, 80%, 90%, or 95% of the cells can be characterized as EA-CPCs (i.e., cells that are SSEA3-positive and c-kit-negative, and that are optionally also CD34-negative and/or CD45-negative) and that are further capable of cardiomyocyte, smooth muscle cell, and/or vascular endothelium differentiation under appropriate ex vivo, in vitro, and/or in vivo conditions.

The EA-CPC population of the presently disclosed subject matter refers in some embodiments to a population of freshly isolated cells from heart tissue. This cell population can be expanded in vitro while maintaining the ability to differentiate into cardiomyocytes. This population is referred to alternatively herein as a population of expanded cardiac progenitor cells of the presently disclosed subject matter or "expanded SSEA3-positive/c-kit-negative" population and the cells are referred to as "EA-CPCs". Suitable conditions for expansion ex vivo or in vitro are known to the skilled person and include but are not limited to those described herein.

In some embodiments, methods for expansion of EA-CPCs of the presently disclosed subject matter comprise cultivating the cells in medium comprising factors such as one or more growth factors, fetal bovine serum and/or a synthetic serum analog, essential and non-essential amino acids, insulin-selenium-transferrin supplement, agents such as mercaptoethanol or L-glutamine, and/or others. In some embodiments, methods for expansion of the EA-CPCs of the presently disclosed subject matter involve cultivation in the presence MTESR™ 1 media (STEMCELL™ Technologies Inc., Vancouver, British Columbia, Canada) with or without serum supplements (in some embodiments, 20% fetal bovine serum; FBS). In some embodiments, the medium can be modified in order to preserve SSEA3-positivity in the cells, for example, but reducing the serum and/or the MTESR™ 1 media itself. In some embodiments, the expansion of the EA-CPCs of the presently disclosed subject matter involve cultivation in the presence MTESR™ 1 media (STEMCELL™ Technologies Inc.) diluted about 40% with another medium (e.g., c-kit medium, which is to Ham's F12 (GIBCO® Life Technologies, a brand of Thermo Fisher Scientific Inc., Grand Island, N.Y., United States of America), 10% FBS (HYCLONE™ brand, Thermo Scientific Inc.), 10 ng/ml Recombinant Human bFGF (PeproTech Inc., Rocky Hill, N.J. United States of America), 0.2 mM L-glutathione (Sigma-Aldrich Corp., St. Louis, Mo., United States of America), 5 ng/ml human erythropoietin (Sigma-Aldrich)).

Also, the presently disclosed subject matter further provides methods for obtaining a population of CPCs from isolated heart tissue, which methods comprise selecting cells that are SSEA3-positive and c-kit-negative from isolated heart tissue. In some embodiments, these methods further comprise selecting cells which are CD34-negative, CD45-negative, or both CD34-negative and CD45-negative. In some embodiments, the selection of SSEA3-positive and c-kit-negative cells comprises contacting cells isolated from heart tissue, either before or after in vitro culture and/or expansion, with a first detectable reagent that specifically binds to SSEA3 or otherwise detects cells expressing SSEA3, detecting the presence of the detectable reagent, and selecting SSEA3-positive cells based on the detection of the detectable reagent. In some embodiments, the selection of SSEA3-positive and c-kit-negative cells comprises contacting cells isolated from heart tissue, either before or after in vitro culture and/or expansion, with a second detectable reagent that specifically binds to c-kit or otherwise detects cells expressing c-kit, detecting the presence of the detectable reagent, and selecting against and/or removing c-kit-positive cells based on the detection of the detectable reagent.

As such, the presently disclosed subject matter further provides tools and kits suitable for the detection and/or selection of the SSEA3-positive cells isolated from heart tissue (i.e., EA-CPCs), expanded EA-CPCs, and/or progeny cells thereof. Thus, the presently disclosed subject matter also relates to the use of one or more markers selected from SSEA3, CD34, CD45, and c-kit for the identification and/or isolation of EA-CPCs and/or compositions comprising EA-CPCs from heart, wherein SSEA3 are positive markers for the desired cell types and c-kit and optionally CD34 and CD45 are negative markers for the desired cell types.

VI. Therapeutic Methods

The ability of EA-CPCs to undergo in vitro expansion can be important for therapeutic applications where a larger number of cells could be required that could be isolated from a subject. Accordingly, in some embodiments the presently disclosed subject matter relates to an expanded population of EA-CPCs.

Upon expansion, EA-CPCs maintain their differentiation capacity. The expanded EA-CPC population of the presently disclosed subject matter is capable of differentiating into cardiomyocytes and is thus equally suitable for therapeutic applications. Accordingly, the presently disclosed subject matter provides in some embodiments methods for generating an expanded population of EA-CPCs, which in some embodiments comprise isolating EA-CPCs as described herein and expanding them such as to obtain an expanded population of EA-CPCs.

The EA-CPCs, expanded EA-CPCs, and compositions comprising EA-CPCs and/or expanded EA-CPCs of the presently disclosed subject matter have a number of therapeutic applications. More particularly, they can be used in the treatment of degenerative heart diseases and repair of heart injury from both ischemic and non-ischemic etiology.

In some embodiments, the presently disclosed subject matter relates to the therapeutic use of the EA-CPCs, expanded EA-CPCs, and compositions disclosed herein, which in some embodiments are formulated as a pharmaceutical composition. Indeed, in view of their ability to differentiate into myocytes, smooth muscle, and vascular endothelium, the EA-CPCs, expanded EA-CPCs, and progeny thereof have important therapeutic value in the restoration, repair, regeneration, and/or reconstitution of damaged heart tissue. Thus, the presently disclosed subject matter encompasses methods for treating subjects in need thereof with a population of EA-CPCs, expanded EA-CPCs, progeny thereof, and/or the compositions disclosed herein.

VI.A. Methods for Restoring Functional and/or Structural Integrity to Damaged and/or Poorly Functional Myocardium In some embodiments, the presently disclosed subject matter provides methods for restoring functional and/or structural integrity to damaged and/or poorly functional myocardium in a subject in need thereof. In some embodiments, the methods comprise administering to the subject an effective amount of a pharmaceutical composition as disclosed herein (i.e., a pharmaceutical composition comprising, consisting essentially of, or consisting of EA-CPCs, expanded EA-CPCs, or progeny cells thereof). In some embodiments, the subject has a myocardial infarction prior to the pharmaceutical composition being administered, optionally wherein the subject had at least one myocardial infarction within one year prior to the pharmaceutical composition being administered. In various embodiments, the subject has left ventricle (LV) dysfunction characterized by an ejection fraction (EF) of less than 50%, less than 45%, or less than 40%. In some embodiments, the administering results in an increase in LVEF of at least 3%, 4%, or 5% within two years post-treatment.

In some embodiments, the c-kit-negative and SSEA3-positive and optionally CD34-negative and/or CD45-negative EA-CPCs present in the pharmaceutical composition are autologous to the subject to whom they are to be administered. In some embodiments, the c-kit-negative and SSEA3-positive and optionally CD34-negative and/or CD45-negative EA-CPCs present in the pharmaceutical composition are allogeneic to the subject to whom they are to be administered, being isolated and/or purified from a donor that is allogeneic to the subject. Thus, in some embodiments the cardiac progenitor cells present in the pharmaceutical composition are c-kit-negative and SSEA3-positive EA-CPCs, are optionally also CD34-negative and/or CD45-negative, and have been isolated from the allogeneic donor (optionally a human donor) and/or that have been prepared from c-kit-negative and SSEA3-positive and optionally also CD34-negative and/or CD45-negative EA-CPCs that have been isolated and/or purified from a cardiac sample isolated from an allogeneic human donor.

VI.B. Methods for Regenerating and/or Repairing Damaged and/or Poorly Functional Myocardium The EA-CPCs of the presently disclosed subject matter are in some embodiments envisioned for use in cardiac muscle regeneration in a number of indications, including, but not limited to: (i) ischemic heart implantations, (ii) therapy for congestive heart failure patients, (iii) prevention of further disease for patients undergoing coronary artery bypass graft, (iv) conductive tissue regeneration, (v) vessel smooth muscle regeneration and (vi) valve regeneration. Thus, the EA-CPCs disclosed herein can also be used to integrate with tissue of a replacement heart valve to be placed into a recipient. In some embodiments, the EA-CPCs of the presently disclosed subject matter repopulate the valve tissue, enabling proper valve function.

The presently disclosed subject matter also provides in some embodiments methods for repairing structure and/or function of damaged and/or poorly functional myocardium in a subject in need thereof. In some embodiments, the methods comprise extracting EA-CPCs from a subject or an autologous or allogeneic human donor; culturing and optionally expanding the EA-CPCs, wherein the EA-CPCs are c-kit-negative and SSEA3-positive and optionally are also CD34-negative and/or CD45-negative; and administering a dose of the extracted, cultured, and optionally expanded autologous or allogeneic EA-CPCs to an area of damaged myocardium in the subject effective to ameliorate the structure and function of the damaged myocardium, ameliorate cardiac scar size, and/or ameliorate arrythmogenic burden in the damaged and/or poorly functional myocardium in the subject. In some embodiments, the extracting step comprises harvesting myocardial tissue comprising the EA-CPCs from the subject or from the autologous or allogeneic human donor. In some embodiments, the c-kit-negative and SSEA3-positive and optionally CD34-negative and/or CD45-negative EA-CPCs are isolated from the biological sample before, after, or concurrently with removing the c-kit-positive cells and the SSEA3-negative cells, and optionally the CD34-positive and CD45-positive cells. In some embodiments, the c-kit-negative and SSEA3-positive and optionally CD34-negative and/or CD45-negative EA-CPCs are administered within and/or to a location in the subject selected from the group consisting of an infarcted region, a border region, a non-infarcted region, a dysfunctional region, and a region of damaged myocardium. In some embodiments, the c-kit-negative and SSEA3-positive and optionally CD34-negative and/or CD45-negative EA-CPCs are administered intraarterially and/or intravenously, optionally via a catheter and/or by injection. In some embodiments, the c-kit-negative and SSEA3-positive and optionally CD34-negative and/or CD45-negative EA-CPCs are administered transendocardially, epicardially, and/or intracoronarily, optionally via a catheter and/or by injection.

In some embodiments of the presently disclosed subject matter, the damaged and/or dysfunctional myocardium is a result of a non-ischemic process, optionally wherein the non-ischemic process is selected from the group consisting of hypertensive cardiomyopathy, diabetic cardiomyopathy, chemotherapy induced cardiomyopathy, valvular cardiomyopathy, and idiopathic cardiomyopathy, or any combination thereof. In some embodiments, the dose of the extracted, cultured, and optionally expanded cardiac progenitor cells that is effective to ameliorate the structure and function of the damaged myocardium is a dose sufficient to form myocardial tissue, decrease scar size, ameliorate fibrosis, form new cardiac vasculature, increase viable cardiac tissue, and/or form one or more coronary vessels in the subject.

In some embodiments, the presently disclosed subject matter also provides methods for regenerating and/or repairing damaged and/or poorly functional myocardium in a subject in need thereof. In some embodiments, the methods comprise administering a dose of a pharmaceutical composition as described herein to an area of damaged and/or poorly functional myocardium in the subject, wherein the EA-CPCs and/or progeny cells thereof differentiate into mature, functional cardiomyocytes and/or induce the generation of new cardiomyocytes following administration to an extent sufficient to regenerate and/or repair the damaged and/or poorly functional myocardium in the subject. In some embodiments, the EA-CPCs and/or progeny cells thereof are autologous or allogeneic to the subject. In some embodiments, the pharmaceutical composition is administered to a location in the subject selected from the group consisting of an infarct zone, a border zone, a non-infarct zone, a scar, a functional region, a dysfunctional region, a valvular region, a perivalvular region, or any combination thereof of the myocardium in the subject. In some embodiments, the pharmaceutical composition is administered transendocardially, intramyocardially, transepicardially by injection or optionally via a catheter.

In some embodiments of the presently disclosed methods, the pharmaceutical composition further comprises an additional component selected from the group consisting of a growth factor, a cytokine, a natural or synthetic extracellular matrix component, a scaffold, and any combination thereof.

In some embodiments, the subject has a history of acute myocardial infarction and/or remote myocardial infarction within one year prior to administering the pharmaceutical composition.

In some embodiments, the presently disclosed methods for regenerating and/or repairing damaged myocardium in a subject in need thereof comprise providing a pharmaceutical composition comprising cardiac progenitor cells that are autologous or allogeneic to the subject, wherein the EA-CPCs are SSEA3-positive and c-kit-negative and optionally also CD34-negative and/or CD45-negative that were isolated from adult myocardium that is autologous or allogeneic to the subject and/or are SSEA3-positive and c-kit-negative, and optionally also CD34-negative and/or CD45-negative progeny cells thereof and administering the pharmaceutical composition to an area of damaged myocardium in the subject, wherein the cardiac progenitor cells directly differentiate into and/or indirectly cause formation of new mature, functional cardiomyocytes following administration, thereby regenerating and/or repairing damaged myocardium in the subject.

In some embodiments, the cardiac progenitor cells are provided by harvesting myocardial tissue from the subject and/or an allogeneic donor and isolating SSEA3-positive and c-kit-negative and optionally also CD34-negative and/or CD45-negative EA-CPCs from the myocardial tissue, optionally wherein the SSEA3-positive and c-kit-negative and optionally also CD34-negative and/or CD45-negative EA-CPCs are expanded in culture and/or further purified prior to administration.

In some embodiments, the subject and the allogenic and/or allogeneic donor are both humans.

The presently disclosed subject matter thus provides in some embodiments methods for repairing damaged myocardium in a subject in need thereof comprising administering to a subject in need thereof a pharmaceutical composition as set forth herein, wherein the structural and/or functional integrity in part or in whole of the damaged myocardium is at least partially restored following administration of the pharmaceutical composition. In some embodiments, the pharmaceutical composition comprises isolated c-kit-negative and SSEA3-positive and optionally CD34-negative and/or CD45-negative EA-CPCs that are autologous and/or allogeneic to the subject. In some embodiments, the pharmaceutical composition is administered transendocardially, intramyocardially, intracoronarily, and/or transepicardially.

VI.C. Methods for Reconstituting Cardiac Tissue

The presently disclosed subject matter also provides in some embodiments methods for reconstituting cardiac tissue in a subject in need thereof. In some embodiments, the methods comprise administering to damaged cardiac tissue in the subject a pharmaceutical composition that comprises an isolated population of enriched in EA-CPCs and/or progeny cells derived therefrom, wherein the EA-CPCs and/or progeny cells derived therefrom are c-kit-negative and SSEA3-positive and are also optionally CD34-negative and/or CD45-negative; and a pharmaceutically acceptable carrier and/or excipient to injured or dead cardiac tissue, wherein at least 50%, 60%, 70%, 75%, 80%, 85%, 90%, 95%, 96%, 97%, 98%, 99%, or 100% of the cells present in the pharmaceutical composition are c-kit-negative and SSEA3-positive and optionally CD34-negative and/or CD45-negative EA-CPCs and/or c-kit-negative and SSEA3-positive and optionally CD34-negative and/or CD45-negative progeny cells derived therefrom. In some embodiments, the cardiac tissue is myocardium.

VI.D. Formulations

The compositions of the presently disclosed subject matter comprise in some embodiments a composition that includes EA-CPCs as disclosed herein and a carrier, particularly a pharmaceutically acceptable carrier, such as but not limited to a carrier pharmaceutically acceptable for use in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants and/or biological response modifiers (BRMs) including, but not limited to, cytokines and other immunomodulating compounds. Exemplary adjuvants and/or biological response modifiers include, but are not limited to insulin-like growth factor I (IGF-I), monoclonal antibodies, interferons (IFNs, including but not limited to IFN-α and IFN-γ), interleukins (ILs, including but not limited to IL2, IL4, IL6, and IL10), cytokines (including, but not limited to tumor necrosis factors), and colony-stimulating factors (CSFs, including by not limited to GM-CSF and G-CSF).

VI.E. Administration

The EA-CPCs-based therapies of the presently disclosed subject matter can be provided by several routes of administration. In some embodiments, intracardiac muscle injection is used, which avoids the need for an open surgical procedure. The EA-CPCs can in some embodiments be introduced in an injectable liquid suspension preparation or in a biocompatible medium that is injectable in liquid form and becomes semi-solid at the site of damaged myocardium. A conventional intracardiac syringe or a controllable arthroscopic delivery device can be used so long as the needle lumen or bore is of sufficient diameter that shear forces will not damage the EA-CPCs. The injectable liquid suspension EA-CPCs preparations can also be administered intravenously, either by continuous drip or as a bolus. During open surgical procedures, involving direct physical access to the heart, all of the described forms of EA-CPCs delivery preparations are available options.

As such, suitable methods for administration of the compositions of the presently disclosed subject matter include, but are not limited to intravenous administration and delivery directly to the target tissue or organ. In some embodiments, the method of administration encompasses features for regionalized delivery or accumulation of the compositions of the presently disclosed subject matter at the site in need of treatment. In some embodiments, the compositions of the presently disclosed subject matter are delivered directly into the tissue or organ to be treated, such as but not limited to the heart, particularly the myocardium.

Injection medium can be any pharmaceutically acceptable isotonic liquid. Examples include phosphate buffered saline (PBS), culture media such as X-vivo medium, DMEM (in some embodiments serum-free), physiological saline, 5% dextrose in water (D5W), or any biocompatible injectable medium or matrix.

The cell population of the presently disclosed subject matter can be co-administered with suitable growth factors, such as but not limited to cytokines. However, the ability of the cells of the presently disclosed subject matter to differentiate into cardiomyocytes in the absence of growth factors makes it possible to make use of the (expanded) SSEA-positive/c-kit-negative EA-CPC population as such, without the requirement of additional growth factors for differentiation. However, growth factors can be used for expansion and synergistic effects of myocardial repair. In some embodiments, the EA-CPCs of the presently disclosed subject matter are administered in combination with growth factors.

In some embodiments, a pharmaceutical composition disclosed herein is administered intracoronarily, transendocardially, transepicardially, and/or as part or in whole on a natural or synthetic biocompatible scaffold and/or matrix that is applied onto and/or within the myocardium of the subject. In some embodiments, selective delivery of the cells present in the compositions of the presently disclosed subject matter is accomplished by intravenous injection of the presently disclosed compositions, where the cells present therein can home to the target tissue and/or organ and engraft therein.

The (expanded) EA-CPCs or population of the presently disclosed subject matter can be used as such or in combination with other cell types. By way of example and not limitation, it is envisioned that combinations with c-kit-positive cardiac stem cells, combinations with differentiated cardiomyocytes, combinations with HSCs, combinations with MSCs, combinations with EPCs, combinations with VSELs, and/or combinations with any other cell types can be advantageous for particular applications.

Accordingly, the presently disclosed subject matter provides in some embodiments compositions comprising EA-CPCs of the presently disclosed subject matter and/or expanded EA-CPCs optionally combined with other cell types such as but not limited to ALDH-positive/CD34-negative cells isolated from heart, c-kit-positive cardiac stem cells, HSCs, MSCs, EPCs, undifferentiated or differentiated iPS cells, undifferentiated or differentiated embryonic stem cells, VSELs, or combinations thereof. Such compositions are provided for use in the therapeutic applications described herein. More particularly, such compositions can comprise in some embodiments at least 20%, in some embodiments at least 30%, in some embodiments at least 40%, in some embodiments at least 50%, in some embodiments at least 60%, in some embodiments at least 70% EA-CPCs or expanded EA-CPCs of the presently disclosed subject matter. In some embodiments, the compositions comprise about 70% EA-CPCs or expanded EA-CPCs as disclosed herein.

Additionally or alternatively, the (expanded) EA-CPCs or population of the presently disclosed subject matter can be used in combination with growth factors and/or cytokines. A non-limiting list of suitable growth factors and cytokines includes, but is not limited to fibroblast growth factor (FGF), insulin-dependent growth factor-I (IGF-I), Flk-2/Flt-3 ligand (FL), stem cell factor (SCF), thrombopoietin (TPO), granulocyte-colony stimulating factor (G-CSF), megakaryocyte growth and development factor (MGDF), neuregulin-1 (NRG1), interleukin-3 (IL-3), IL-6, bone morphogenic proteins (BMPs). Accordingly, the presently disclosed subject matter provides in some embodiments for compositions comprising EA-CPCs and/or expanded EA-CPCs, optionally combined with one or more growth factors and/or cytokines and/or extracellular matrix components.

A pharmaceutical composition as described herein can be administered once, twice, three times, or more. In some embodiments, the pharmaceutical composition is administered to the subject on at least two separate occasions. The pharmaceutical composition can also be administered to the subject in a single dose on a single occasion, in two or more doses on a single or multiple occasions, on at least two separate occasions, etc. In those embodiments wherein the pharmaceutical composition is administered to the subject in two or more doses covering multiple occasions, the time between the administrations of the doses can be hours, days, weeks, or months.

VI.F. Dose

An effective dose of a composition of the presently disclosed subject matter is administered to a subject in need thereof. A "treatment effective amount", "therapeutic amount", or "effective amount" as those phrases are used herein is an amount of a therapeutic composition sufficient to produce a measurable response (e.g., a biologically or clinically relevant response in a subject being treated). Actual dosage levels of an active agent or agents (e.g., EA-CPCs) in the compositions of the presently disclosed subject matter can be varied so as to administer an amount of the active agent(s) that is effective to achieve the desired therapeutic response for a particular subject. In some embodiments, an effective amount comprises about $10^6$ to about $10^9$ c-kit-negative and SSEA3-positive and optionally CD34-negative and/or CD45-negative EA-CPCs.

The selected dosage level can depend upon the activity of the therapeutic composition, the route of administration, combination with other drugs or treatments, the severity of the condition being treated, and the condition and prior medical history of the subject being treated. However, it is within the skill of the art to start doses of the compositions of the presently disclosed subject matter at levels lower than required to achieve the desired therapeutic effect and to gradually increase the dosage until the desired effect is achieved. The potency of a composition can vary, and therefore a "treatment effective amount" can vary. However, one skilled in the art can readily assess the potency and efficacy of a therapeutic composition of the presently disclosed subject matter and adjust the therapeutic regimen accordingly.

Representative examples of a dose range are volumes of about 200 µL to about 20 mL. The number of cells to be injected can be determined in some embodiments by the size of the injury sustained by the patient and method of administration. Typically, in some embodiments at least $1\times10^5$ cells, in some embodiments at least $1\times10^6$ cells, in some embodiments at least $1\times10^7$ cells, in some embodiments at least $1\times10^8$ cells, and in some embodiments at least $1\times10^9$ or more EA-CPCs can be administered. The frequency and duration of therapy can vary depending on the degree (percentage) of tissue involvement.

After review of the disclosure of the presently disclosed subject matter presented herein, one of ordinary skill in the art can tailor the dosages to an individual subject, taking into account the particular formulation, method of administration to be used with the composition, and particular injury treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art.

VI.G. Summary of Therapeutic Methods

Summarily, the presently disclosed subject matter provides in some embodiments methods for treating a subject diagnosed with a damaged myocardium, the method comprising providing a pharmaceutical composition as described herein to the subject. In some embodiments, the damaged and/or poorly functional myocardium results from ischemic cardiomyopathy. In some embodiments, the damaged and/or poorly functional myocardium results from non-ischemic cardiomyopathy. In some embodiments, the damaged and/or poorly functional myocardium results from a cardiac injury or disease selected from the group consisting of myocardial infarct, left ventricular hypertrophy, right ventricular hypertrophy, emboli, heart failure, congenital heart deficit, heart valve disease, arrhythmia, myocarditis, infection, trauma, hypertension, diabetes, chemotherapy, fibrosis, infiltrative diseases, autoimmune diseases, a side effect of medication, and any combination thereof. In some embodiments, the damaged myocardium is secondary to a chemotherapeutic treatment. In some embodiments, the chemotherapeutic treatment employs an anthracycline and/or HERCEPTIN® (trastuzumab; Genentech, South San Francisco, Calif., United States of America).

Typical diseases and injuries which are susceptible to treatment by the administration of cells capable of developing into cardiomyocytes include but are not limited to congestive heart failure (e.g., ischemic cardiac insults such as myocardial infarctions). Accordingly, the presently disclosed subject matter provides methods of treatment of heart injury comprising administering a cell population as disclosed herein to a patient in need thereof.

Accordingly, in some embodiments the presently disclosed subject matter provides a EA-CPC population and/or expanded EA-CPCs, or compositions comprising EA-CPCs and/or expanded EA-CPCs of the presently disclosed subject matter for use as a medicament. More particularly, these cells and cell populations are envisioned for use in the indications described above, more particularly for use in the treatment of myocardial infarction.

In the therapeutic applications described herein, the EA-CPC population and/or the expanded EA-CPCs of the presently disclosed subject matter can be used as an autologous, allogeneic, and/or xenogeneic cell population, whereby the choice largely depends on the urgency of the need for treatment. A patient presenting an imminently life-threatening condition can be maintained on a heart/lung machine while sufficient numbers of autologous EA-CPCs are cultured or initial treatment can be provided using other than autologous EA-CPCs.

In some embodiments, the EA-CPCs and/or the expanded EA-CPCs according to the presently disclosed subject matter are envisioned to be used for the generation of personalized medicaments. Indeed, the cells as such as well as their number and their properties may be selected based on the requirements of the patient.

VII. Exemplary Other Embodiments

VII.A. Devices, Tools, and Kits for Identifying, Detecting, and/or Isolating EA-CPCs In some embodiments, the presently disclosed subject matter provides devices, tools, and kits for identifying, detecting, and/or isolating the EA-CPCs population of the presently disclosed subject matter. Suitable devices for identification and/or selection of the presently disclosed EA-CSC population are known in the art and include, for example, cell sorters such as but not limited to flow cytometers such as the Beckman-Coulter MOFLOW® brand cell sorter, the Sony Cell Sorter SH800, magnetic beads such as CLINIMACS®, other kits such as ALDEFLUOR® and ALDESORT®. However, other devices and tools can be developed based on similar principles. These can be adjusted or specifically developed for the identification of the SSEA-positive CSC population disclosed herein.

Accordingly, the kits, tools, and devices envisioned herein are combinations of tools suitable for identifying the EA-CPCs of the presently disclosed subject matter, more particularly tools suitable for determining the expression of suitable markers optionally combined with other features of the cell populations and subpopulations described herein.

VII.B. Gene Therapy Applications

It is furthermore envisioned that the presently disclosed cells and/or populations of cells are suitable for transplantation and gene therapy applications. In some embodiments, an EA-CPC or a progeny cell thereof can be transduced with an expression vector comprising a coding sequence of interest. The coding sequence of interest can be any coding sequence for which expression in a recipient's heart might be desired. The transduced EA-CPC or the progeny cell thereof can be administered into the recipient where it can differentiate into a mature cardiac lineage including, but not limited to a cardiomyocyte, a smooth muscle cell, and/or an endothelial cell and express the coding sequence of interest. Any coding sequence of interest can be provided including, but not limited to, IGF-1, IGF-1R, PIM-1 kinase, HO-1, and/or eNOS.

VII.C. Generation of Functional Cardiac Cells and Uses Therefor

In some embodiments, the presently disclosed subject matter also provides EA-CPC populations and/or expanded EA-CPCs for use in the generation of functional cardiac cells. Indeed, EA-CPCs have the ability to differentiate into myocytes, smooth muscle cells, and endothelial cells, including in vitro. In addition, the ability to expand the EA-CPCs maintaining their ability to differentiate into myocytes, smooth muscle cells, and endothelial cells has also been demonstrated.

Thus, the EA-CPCs and expanded EA-CPCs of the presently disclosed subject matter are in some embodiments a source of cardiac myocytes. Accordingly, in some embodiments the presently disclosed subject matter provides methods for the generation of cardiomyocytes, which involve the cultivation and differentiation of the EA-CPCs disclosed herein. In some embodiments, these methods involve the monocultivation of EA-CPCs and their differentiation into cardiomyocytes. Alternatively, co-cultivation of EA-CPCs is also envisioned. The myocytes obtainable by the methods disclosed herein are suitable for therapeutic use in the treatment of heart conditions such as, but not limited to, congestive heart failure and other ischemic and/or non-ischemic cardiac insults such as myocardial infarctions. Accordingly, the presently disclosed subject matter provides methods of treatment or prevention of a heart injury comprising administering a cardiomyocyte population obtainable from the EA-CPCs disclosed herein to a subject in need thereof.

The conditions described herein above (e.g., dosage, source, cocultivation, optional use of a scaffold, etc.) in connection with the therapeutic use of EA-CPCs of the presently disclosed subject matter are similarly applicable to the therapeutic use of cardiomyocytes obtainable from cultivation of EA-CPCs.

EXAMPLES

The presently disclosed subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Materials and Methods Employed in the Examples

RNA Extraction Protocol.
RNA was extracted from cells and tissues using the PUREUNK® RNA Mini Kit (Life Technologies, Inc.) according to the manufacturer's instructions as follows.
1. Collect cells and wash with pre-ice cold DPBS. Spin the cells at 500 g for 8 min each wash.
2. Add 1 ml Lysis Buffer for 1.0-1.5×10$^6$ cells with 1% β-Mercaptoethanol to the cell pellet. Vortex until the cells is dispersed and the cells appear lysed.
3. Homogenize the lysate with 1 ml Insulin Safety Syringe (Covidien Monoject Permanent Needle; Covidien, Mansfield, Mass., United States of America) 4-8 times.
4. Add one volume (1 ml) 70% ethanol to the cell homogenate. Vortex thoroughly until no any visible precipitate.
5. Transfer up to 700 µl of the homogenized sample (including any remaining precipitate) to spin cartridge and spin at maximum speed 15 sec. Discard the flow-through, and repeat until the entire sample has been processed into spin cartridge.
6. Wash the spin cartridge once with Wash Buffer I and spin at maximum speed for 15 sec and discard the flow-through.
7. Wash the spin cartridge twice with Wash Buffer II containing ethanol. Spin at maximum speed for 15 sec and discard the flow-through each time.
8. Elute spin cartridge with 30 µl RNase-free water to the center of cartridge, standing for 1 minute and spin at maximum speed for 2 minutes.
9. Measure RNA concentration using Nano-Drop and store the RNA at −80° C.

cDNA Synthesis.
cDNA was synthesized from RNA using the High-Capacity cDNA Reverse Transcription Kit (Applied Biosystems, South San Francisco, Calif., United States of America) according to the manufacturer's instructions as follows.
1. Thaw all components on ice.
2. Prepare 2×RT Master Mix (10 µl for each reaction): Add 2.0 µl of 10×RT Buffer; 0.8 µl of 25×dNTP; 2.0 µl of 10×RT Random Primer; 1.0 µl of Reverse Transcriptase in 4.2 µl Nuclease-free H$_2$O.

3. 200 ng of RNA sample in Nuclease-free H2O to 10 μl final volume.
4. Each 10 μl of 2×RT Master Mix is added into 10 μl of RNA sample.
5. Perform at the following thermal cycling conditions:
   Step 1: 25° C. for 10 minutes;
   Step 2: 37° C. for 120 minutes;
   Step 3: 85° C. for 5 minutes; and
   Step 4: 4° C. holding
6. Store the cDNA at −20° C.

Real-Time PCR.

RT-PCR was performed using the Power SYBR Green PCR Master Mix (Applied Biosystems), the MicroAmp Optical 96-Well Reaction Plate (Applied Biosystems), and the MicroAmp Optical Adhesive Film (Applied Biosystems). The basic protocol is as follows:

Sample Preparation (Pre-Setup Plate Using 96-Well Plate Template):
1. Make a cocktail of SYBR Green Master Mix and forward/reverse primers that is enough for all the reactions. For each reaction:
   7.5 μl of Nuclease-free H₂O;
   1.5 μl of forward primer (5 μM solution);
   1.5 μl reverse primer (5 μM solution) and
   12.5 μl of SYBR Green PCR Master Mix.
2. Add 2 μl cDNA sample to each well and each of samples in triplicates.
3. Add 23 μl of cocktail of SYBR Green Master Mix into each well.
4. Cover reaction plate with adhesive film. Make sure the plate is sealed well.
5. Centrifuge reaction plate briefly to collect all liquid at the bottom of the plate.

Instrument Operation:
1. Turn on ABI StepOnePlus system and load in plate
2. Open StepOnePlus Software v2.1 on desktop
3. Select [New Experiment] and type experiment name
4. Setup [StepOnePlus instrument (96 wells)]>[Quantitation]>[Comparative Ct (ΔΔCt)]>[SYBR Green Reagent]>[Standard~2 hours to complete a run]>[cDNA] and click Next
5. Input how many targets do you want to quantify in the reaction plate (e.g., 7). Type target names and click Next
6. Input how many samples do you want to test in the reaction plate (e.g., 4), how many replicates do you need (type 3) and how many negative control (e.g., 3). When finish, click Next
7. Select which sample do you want to use as the reference sample and select which target do you want to use as the endogenous control. When finish all designing, click Finish Designing Experiment and a window will display your plate layout. You can click [Edit Plate Layout]>Assign Targets and Samples to edit your plate
8. When all Setup are finished, Save As a template for your convenience if you will do the same experiment with different samples
9. When all things done, click Start to perform your program
10. After program is completed, click Export to download your results to your flash drive.

Regular PCR Protocol:

Reagents: REDEXTRACT-N-AMP™ PCR Reaction Mix (Sigma-Aldrich)

| | |
|---|---|
| H₂O | 3.0 μl |
| Forward Primer | 0.5 μl |
| Reverse Primer | 0.5 μl |
| Reaction Mix | 5 μl |
| cDNA | 1 μl |

Perform PCR at:
(1) 50° C. for 2 minutes
(2) 95° C. for 10 minutes
(3) 95° C. for 15 seconds
(4) 62° C. for 30 seconds
(5) 72° C. for 30 seconds
   Repeat (3)-(5) for 35 cycles
(6) 72° C. for 10 minutes
(7) 10° C. hold
Run 2.5% gel to see PCR products
A listing of all oligonucleotide primers utilized for RT-PCR and qPCR is presented in Table 1.

TABLE 1

Specific Primer Sequences Employed for RT-PCR

| Gene Name | Primer Sequences (SEQ ID NO:) | Exemplary GENBANK ® Accession Nos.# |
|---|---|---|
| β₂-M | F: 5'-AATGCGGCATCTTCAAAC-3' (SEQ ID NO: 1)<br>R: 5'-TGACTTTGTCACAGCCCA-3' (SEQ ID NO: 2) | NM_004048.2 |
| OCT-4 | F: 5'-GATGTGGTCCGAGTGTGG-3' (SEQ ID NO: 3)<br>R: 5'-TGTGCATAGTCGCTGCTT-3' (SEQ ID NO: 4) | NM_002701.5<br>NM_203289.5<br>NM_001173531.2<br>NM_001285986.1<br>NM_001285987.1 |
| NANOG | F: 5'-GCAGAAGGCCTCAGCAC-3' (SEQ ID NO: 5)<br>R: 5'-AGGTTCCCAGTCGGGTTC-3' (SEQ TD NO: 6) | NM_024865.2 |
| NKX2.5/CSX | F: 5'-CCCCTGGATTTTGCATTC-3' (SEQ ID NO: 7)<br>R: 5'-CGTGCGCAAGAACAAAC-3' (SEQ ID NO: 8) | NM_004387.3<br>NM_001166175.1<br>NM_001166176.1 |

TABLE 1-continued

Specific Primer Sequences Employed for RT-PCR

| Gene Name | Primer Sequences (SEQ ID NO:) | Exemplary GENBANK® Accession Nos.# |
|---|---|---|
| GATA4 | F1: 5'-AACGACGGCAACAACGATAAT-3' (SEQ ID NO: 9)<br>R1: 5'-GTTTTTTCCCCTTTGATTTTTGATC-3' (SEQ ID NO: 10)<br>F2: 5'-AAGACACCAGCAGCTCCTTC-3' (SEQ ID NO: 11)<br>R2: 5'-TGTGCCCGTAGTGAGATGAC-3' (SEQ ID NO: 12) | NM_002052.3 |
| MEF2C | F: 5'-CTGGCAACAGCAACACCT-3' (SEQ ID NO: 13)<br>R: 5'-GCTAGTGCAAGCTCCCAA-3' (SEQ ID NO: 14) | NM_002397.4<br>NM_001131005.2<br>NM_001193347.1<br>NM_001193348.1<br>NM_001193349.1<br>NM_001193350.1 |
| vWF | F: 5'-CCCTGGGTTACAAGGAAG-3' (SEQ ID NO: 15)<br>R: 5'-AGTGTCATGATCTGTCCTCCT-3' (SEQ ID NO: 16) | NM_000552.3 |
| AMHC/MYH6 | F: 5'-CCAGACGGCACCGAAGAT-3' (SEQ ID NO: 17)<br>R: 5'-ACATACTCGTTGCCCACTTTCA-3' (SEQ ID NO: 18) | NM_002471.3 |
| c-KIT | F1: 5'-CCAACCAAGGCCGACAAA-3' (SEQ ID NO: 19)<br>R1: 5'-GGCGGGAGTCACATCTCTTTC-3' (SEQ ID NO: 20)<br>F2: 5'-GAGCACCAATCATATTTACTCCA-3' (SEQ ID NO: 21)<br>R2: 5'-GAATTGATCCGCACAGAATG-3 (SEQ ID NO: 22)<br>F3: 5'-CCAACCAAGGCCGACAA-3' (SEQ ID NO: 23)<br>R3: 5'-GGCGGGAGTCACATCTCT-3' (SEQ ID NO: 24) | NM_000222.2<br>NM_001093772.1 |
| CTNI/TNNI3 | F: 5'-ACGCCGCTCCTCCAACTAC-3 (SEQ ID NO: 25)<br>R: 5'-CAGCAGAGTCTTCAGCTGCAA-3' (SEQ ID NO: 26) | NM_000363.4 |
| GATA6 | F: 5'-AAAGAGGGAATTCAAACC-3' (SEQ ID NO: 27)<br>R: 5'-GAAGTTGGAGTCATGGGA-3' (SEQ ID NO: 28) | NM_005257.4 |
| KDR | F: 5'-GAGGAGAAGTCCCTCAGT-3' (SEQ ID NO: 29)<br>R: 5'-ACTTGGAAGCTGTAACAG-3' (SEQ ID NO: 30) | NM_002253.2 |
| SM-MHC/MYH11 | F: 5'-TGGGCGAGATGTGGTACAGA-3' (SEQ ID NO: 31)<br>R: 5'-TCACGCGGGTGAGTATCCA-3 (SEQ ID NO: 32) | NM_001040114.1<br>NM_022844.2<br>NM_001040113.1 |
| TERT | F1: 5'-CGTCGAGCTGCTCAGGTCTT-3' (SEQ ID NO: 33)<br>R1: 5'-AGTGCTGTCTGATTCCAATGCTT-3' (SEQ ID NO: 34)<br>F2: 5'-GCCACGTCTCTACCTTGACA-3' (SEQ ID NO: 35)<br>R2: 5'-GAGGAGCTCTGCTCGATGA-3' (SEQ ID NO: 36) | NM_198253.2<br>NM_001193376.1 |
| ISL1 | F1: 5'-GGTTGTACGGGATCAAATGC-3' (SEQ ID NO: 37)<br>R1: 5'-GCCCGTCATCTCTACCAGTT-3' (SEQ ID NO: 38)<br>F2: 5'-GTTACCAGCCACCTTGGAAA-3' (SEQ ID NO: 39) | NM_002202.2 |

TABLE 1-continued

Specific Primer Sequences Employed for RT-PCR

| Gene Name | Primer Sequences (SEQ ID NO:) | Exemplary GENBANK® Accession Nos.[#] |
|---|---|---|
| | R2: 5'-TTCCCACTTTCTCCAACAGG-3' (SEQ ID NO: 40) | |
| TBX5 | F: 5'-TTCTGCACTCACGTCTTTCC-3' (SEQ ID NO: 41) R: 5'-TGGCAAAGGGATTATTCTCA-3' (SEQ ID NO: 42) | NM_000192.3 NM_080717.2 NM_181486.2 |
| TBX18 | F: 5'-CAACAGAATGGGTTTGGAAG-3' (SEQ ID NO: 43) R: 5'-AAGGTGGAGGAACTTGCATT-3' (SEQ ID NO: 44) | NM_001080508.2 |
| TBX20 | F: 5'-AGCTTTGGGACAAATTCCAT-3' (SEQ ID NO: 45) R: 5'-CTTGGCCTCAGGATCCAC-3' (SEQ ID NO: 46) | NM_001077653.2 NM_001166220.1 |
| MLC2A (MYL7) | F: 5'-AGGTGAGTGTCCCAGAGGAG-3 (SEQ ID NO: 47) R: 5'-GGTCTGTCCCATTGAGCTTC-3' (SEQ ID NO: 48) | NM_021223.2 |
| MLC2V (MYL2) | F: 5'-GGCTTCATTGACAAGAACGA-3' (SEQ ID NO: 49) R: 5'-GGAGCCTCCTTGATCATTTC-3' (SEQ ID NO: 50) | NM_000432.3 |
| WT1 | F: 5'-GGCATCTGAGACCAGTGAGA-3' (SEQ ID NO: 51) R: 5'-TTTCTCACCAGTGTGCTTCC-3' (SEQ ID NO: 52) | NM_000378.4 NM_024424.3 NM_024426.4 NM_001198551.1 NM_001198552.1 |
| BRACHYURY (T) | F1: 5'-GTGCTGTCCCAGGTGGCTTACAGATG-3' (SEQ ID NO: 53) R1: 5'-CCTTAACAGCTCAACTCTAACTACTTG-3' (SEQ ID NO: 54) F2: 5'-TGCTGCAATCCCATGACA-3' (SEQ ID NO: 55) R2: 5'-CGTTGCTCACAGACCACA-3' (SEQ ID NO: 56) | NM_003181.3 NM_001270484.1 |
| MIXL1 | F: 5'-GGATCCAGGTATGGTTCCAG-3' (SEQ ID NO: 57) R: 5'-GGAGCACAGTGGTTGAGGAT-3' (SEQ ID NO: 58) | NM_001282402.1 NM_031944.2 |
| SOX2 | F: 5'-TGGGTTCGGTGGTCAAGT-3' (SEQ ID NO: 59) R: 5'-CTCTGGTAGTGCTGGGACA-3' (SEQ ID NO: 60) | NM_003106.3 |
| MESP1 | F: 5'-CGCTATATCGGCCACCTGTC-3' (SEQ ID NO: 61) R: 5'-GGCATCCAGGTCTCCAACAG-3' (SEQ ID NO: 62) | NM_018670.3 |
| GAPDH | F: 5'-AGCCACATCGCTCAGACAC-3' (SEQ ID NO: 63) R: 5'-GCCCAATACGACCAAATCC-3' (SEQ ID NO: 64) | NM_002046.5 NM_001289745.1 NM_001289746.1 |

[#]the listed Accession Nos. are exemplary only, and nucleotide sequences corresponding to orthologous gene products and/or for other transcript variants are also encompassed within the presently disclosed subject matter.

Western Blot Protocol.

Protein Extraction:

All reagents were purchased from Sigma-Aldrich unless otherwise specified. Adherent cells were washed twice in the dish or flask with ice-cold PBS. The PBS was drained off. An appropriate volume of TRYPLE™ Express (GIBCO®) was added to the flask to dissociate the cells and the cells were transferred to a 1.5 ml centrifuge tube. Cells were washed twice with ice-cold PBS and the PBS was drained off. Ice-cold lysis buffer (1% NP40, 150 mM NaCl, 20 mM Tris-HCl, 1% Triton X-100, 4 mM PMSF, 1:100 Proteinase Inhibitor Cocktail) was added to the cells (1 ml per $10^7$ cells/100 mm dish or 150 cm² flask; 0.5 ml per 5×10⁶ cells/60 mm dish or 75 cm² flask). Cells were mixed thoroughly and soniccated at appropriate intervals as needed. Cells were incubated on ice for at least 15 minutes to lyse the cells. The lysate was centrifuged at 14,000×g in a precooled centrifuge for 20 minutes at 4° C. The supernatant was immediately transferred to a fresh centrifuge tube and the pellet discarded. Protein concentration was determined using the Bio-Rad Protein Assay Dye Reagent according to the manufacturer's instructions. Sample were divided into aliquots and stored at −80° C. as needed.

Western Blot Procedure:

10% SDS-PAGE gels were prepared with reagents from Bio-Rad. 15 µg of protein were loaded for each sample and the gel was run in Running Buffer (25 mM Tris-HCl; 250 mM glycine; 0.1% SDS) for approximately 1.5 hours. Proteins were transferred to membranes in Transfer Buffer (24 mM Tris-HCl; 194 mM glycine; 0.01% SDS) at 60V for 2.5 hours. The membranes were stained with 0.2% Ponceau S after transfer to ensure that the proteins transferred efficiently. Membranes were cut at appropriate molecular weights (kDa) as needed. Membranes were blocked with 25 ml of 3% milk in TBST Buffer (10 mM Tris; 150 mM Nacl; 0.1% TWEEN®-20) and incubated at room temperature for 30-60 minutes. Primary antibodies were prepared according to the manufacturers' instructions, added to the membranes in blocking buffer (3% milk in TBST), and incubated overnight at 4° C. with gentle rocking. The next day, membranes were washed three times with TBST, 5 minutes per wash. 6-10 ml of HRP-linked secondary antibodies were added and membranes were incubated at room temperature for 1-1.5 hours with gentle rocking. Membranes were washed with TB ST three times for 5 minutes each and signal was detected with an ECL reagent (HYGLO™ brand, Denville Scientific Inc., Metuchen, N.J. United States of America) according to the manufacturer's instructions.

Reagents:

Lysis Buffer:

(Modified RIPA buffer—RadioImmunoPrecipitationAssay).

Normally used for post-nuclear lysate preps.

| 1x-1 ml | | Final conc | |
|---|---|---|---|
| 50 µl | 1M Tris pH 7.5 | [50 mM] | |
| 30 µl | 5M NaCl | [150 mM] | |
| 10 µl | Nonident P40 Variation: Triton X-100 | [1%] | |
| 2 µl | 500 mM EDTA pH 7.4 | [1 mM] | (Optional) |
| 10 µl | 10% SDS | [0.1%] | |
| 5 µl | 200 mM EGTA | [1 mM] | (Optional) |
| 50 µl | 10% Na-deoxycholate | [0.5%] | |

Subtotal volume = 157 µl
778 µl H₂O

Prepare the above stock and then add the following inhibitors just before using.

| 40 µl | Protease Cocktail | [1:100] |
|---|---|---|
| 10 µl | 100 mM PMSF | [1 mM] |
| see note below | | |
| 10 µl | 1M NaF | [10 mM] |
| 5 µl | 200 mM Na3VO4 | [1 mM] |

See Activation note below
Subtotal volume = 65 µl
Note: Can substitute the following protease inhibitors for the cocktail pill above

| 1 µl | 10 mg/ml aprotinin | [1 µg/ml] |
|---|---|---|
| See Variation below: | | |
| 1 µl | 10 mg/ml leupeptin | [1 µg/ml] |
| 1 µl | 10 mg/ml pepstatin | [1 µg/ml] |

Variation: 2 µg/ml

Variation: Can use a Complete Protease Inhibitor Cocktail (Sigma-Aldrich) in place of the aprotinin, leupeptin and pepstatin.

Na₃VO₄ is added to inhibit removal of phosphate groups. The activity of Na₃VO₄ can be substantially increased by the following activation procedure:
Make 200 mM stock (0.368 g/10 ml H₂O)
Adjust to pH 10 using HCl or NaOH
Boil until colorless (approx 10 minutes)
pH to 10 again
Repeat boiling and pH adjustment until liquid is colorless and pH stabilizes
Aliquot and store at −20° C.
PMSF is extremely unstable (30 minutes) in aqueous form. So stock was made up in isopropanol and stored at −20° C. and then added just before using. To make 10 ml of 100 mM add 0.174 g PMSF to 10 ml isopropanol.
Store samples at −80° C. Boil for 5 minutes before loading onto gels.
1× Ponceau S (0.2%)
0.2 g Ponceau S
3 mL acetic acid
H₂O to 100 mL
1.5 M Tris/0.4% SDS, pH 8.8 (Stock Buffer for Separating Gels):
Dissolve 181.65 g Tris base in around 800 mL of ddH₂O
Adjust the pH to 8.8 with concentrated HCl
Add 4 g SDS
Bring up the volume to 1 L with ddH₂O
Note: Make sure to let the solution cool down to room temperature before making the final pH adjustment.
1.0 M Tris/0.4% SDS, pH 6.8 (Stock Buffer for Stacking Gels):
Dissolve 121.1 g Tris base in around 700 mL of ddH₂O
Adjust the pH to 6.8 with concentrated HCl
Add 4 g SDS
Bring up the volume to 1 L with ddH₂O
Note: Make sure to let the solution cool down to room temperature before making the final pH adjustment.
10× Tris-Glycine Running Buffer (do not Adjust pH):
121.1 g Tris base (30.3 g/L)
576 g glycine (144 g/L)
200 mL 20% SDS (10 g/L)
Bring up the volume to 4 L with ddH₂O
1×Tris-Glycine Running Buffer: 25 mM Tris; 250 mM Glycine; 0.1% SDS
900 mL cold ddH₂O
100 mL 10× Tris-glycine Running buffer
10× Transfer Buffer (do not Adjust pH):
30.3 g Tris base
144 g glycine
1.0 g SDS
Bring up the volume to 1 L with ddH₂O
1× Transfer Buffer: 24 mM Tris; 194 mM Glycine; 0.01% SDS, Store at 4° C.
700 mL cold ddH₂O 100 mL 10× Transfer buffer
200 mL methanol
10×TBS:
12.1 g Tris base
87.7 g NaCl
Bring up the volume to 800 mL with ddH$_2$O
Adjust the pH to 7.6 with concentrated HCl (~40 ml)
Bring up the volume to 1 L with ddH$_2$O
1×TBST: 10 mM Tris; 150 mM Nacl; 0.1% TWEEN®-20:
700 mL cold ddH$_2$O
100 mL 10×TBS
Add 1 mL TWEEN®-20 to 1 L of 1×TBS A listing of all antibodies utilized for flow cytometry, immunocytochemistry, immunohistochemistry, and western blot analyses, and the commercial suppliers therefor, are presented in Table 2.

Table 2

Antibodies Employed and Commercial Suppliers Therefor

Isotype Controls from Vector Labs
  Unconjugated isotype control antibodies for all species listed herein below
Primary Antibodies from eBioscience, Inc.
  Rat IgM anti-human SSEA3: unconjugated and eFluor488-conjugated
  Mouse IgG3a anti-human SSEA4: unconjugated and PE-conjugated
  Mouse IgM anti-human SSEA1: unconjugated and eFluor450-conjugated
  Mouse IgG anti-human CD34: APC- and eFluor450-conjugated
  Mouse IgG anti-human CD45: APC- and eFluor450-conjugated
  Mouse IgG anti-human CD166 (ALCAM): PE-conjugated
  Mouse IgG anti-human CD105 (Endoglin): APC-, PE-, and eFluor450-conjugated
  Mouse IgG anti-human CD90: APC- and PE-conjugated
  Mouse IgG anti-human CD73: PE-conjugated
  Mouse IgG anti-human CD29 (integrin beta 1): APC-conjugated
  Mouse IgG anti-human CD44: eFluor450-conjugated
  Mouse IgG anti-human CD117(c-kit): APC-conjugated
  Mouse IgG anti-human CD31: PE-conjugated
  Mouse IgG anti-human hematopoietic lineage cocktail (CDs 2, 3, 14, 16, 19, 56, and 235a): APC-conjugated
  Mouse IgM anti-human Tra-1-60 (podocalyxin): unconjugated and PE-conjugated
    Mouse IgM anti-human Tra-1-81 (podocalyxin): unconjugated and PE-conjugated
  Rat IgG anti-human Oct3/4: unconjugated
  Rat IgG anti-human/mouse Sox2: unconjugated
Isotype Controls from eBioscience, Inc.
  Anti-mouse IgM: APC-conjugated
  Anti-mouse IgG: eFluor450-, v450-; PE-, APC-, eFluor488-, and FITC-conjugated
  Anti-rat IgM: eFluor488- and PE-conjugated
Primary Antibody from Dako North America, Inc. (Carpinteria, Calif., United States of America)
  Rabbit IgG anti-human c-kit: unconjugated
Primary Antibodies from Santa Cruz Biotechnology (Santa Cruz, Calif., United States of America)
  Rabbit IgG anti-human c-kit (C19 & H300): unconjugated
  Mouse IgG anti-human Oct3/4: unconjugated
  Goat IgG anti-human Troponin T and Troponin I: unconjugated
  Goat IgG anti-human NKX2.5, GATA-4, and GATA-6: unconjugated
Primary Antibodies from BD Pharmingen/Horizon (BD Biosciences, San Jose, Calif., United States of America)
  Mouse IgM anti-human CD15/SSEA1, CD31 (PECAM), and HLA-ABC: v450-conjugated
  Mouse IgG anti-human HLA-DR: PE-conjugated
Primary Antibodies from Sigma-Aldrich
  Rabbit IgG anti-human Connexin 43, WT-1, and VEGFR2/KDR: unconjugated
  Mouse IgG anti-human smooth muscle actin (SMA) and smooth muscle myosin heavy chain: unconjugated
  Mouse IgM anti-human alpha sarcomeric actin: unconjugated
Primary Antibodies from ABCAM® (Cambridge, Mass. United States of America)
  Rabbit IgG anti-human telomerase reverse transcriptase-C terminal, NANOG, CD34, BRACHYURY, MESP1, SOX2, WT-1, and vWF: unconjugated
  Mouse IgG anti-human NKX2.5, alpha tubulin, P16INK4a, desmin, and α-tubulin: unconjugated
Primary Antibody from Novas Biologicals, LLC (Littleton, Colo., United States of America)
  Mouse IgG anti-human myosin heavy chain: unconjugated
Primary Antibody from EMD Millipore (Billerica, Mass., United States of America)
  Mouse IgG anti-human Nuclear Antigen: unconjugated
Primary Antibody from R&D Systems, Inc.
  Mouse IgM Anti-human CD15(SSEA1): v450-conjugated
Secondary Antibodies from Life Technologies
  Mouse anti-rabbit IgG: Alexa647-, Alexa488-, Alexa543-, FITC-, APC-, and PE-conjugated
  Goat anti-rabbit IgG: Alexa647-, Alexa488-, Alexa543-, FITC-, APC-, and PE-conjugated
  Goat anti-rat IgM: Alexa647-, Alexa488-, Alexa543-, FITC-, APC-, and PE-conjugated
  Donkey anti-mouse IgG: Alexa647-, Alexa488-, Alexa543-, FITC-, APC-, and PE-conjugated
  Donkey anti-goat IgG: Alexa647-, Alexa488-, Alexa543-, FITC-, APC-, and PE-conjugated
  Donkey anti-rat IgG: Alexa647-, Alexa488-, Alexa543-, FITC-, APC-, and PE-conjugated
Western Blot Secondary Antibodies from Cell Signaling Technology, Inc. (Danvers, Mass., United States of America)
  Goat IgG anti-Rat IgG: HRP-conjugated
  Goat IgG anti-Rabbit IgG: HRP-conjugated
  Horse IgG anti-Mouse IgG: HRP-conjugated
Western Blot Secondary Antibody from Santa Cruz Biotechnology
  Donkey IgG anti-Goat IgG: HRP-conjugated
Primary Antibody from eBioscience. Inc. For Immunomagnetic Sorting with Miltenyi Biotec OCTOMACS™
  Rat IgM anti-human SSEA3: PE-conjugated
Magnetic Microbead-Conjugated Antibody from Miltenyi Biotec for Immunomagnetic Sorting with Miltenyi Biotec OCTOMACS™
  Mouse IgG anti-PE

Example 1

Isolation and Analysis of Human Right Atrial Appendage (RAA) Samples

Right atrial appendage (RAA) biopsy samples were obtained from patients undergoing coronary artery bypass surgery (CABG) under IRB approval at Jewish Hospital in Louisville, Ky., United States of America. Each RAA sample was harvested at the site of bypass catheter insertion into the right atrium (see FIG. 2). RAA biopsy weights varied from about 20 to about 300 mg.

After resection of epicardial fibrous and adipose tissue, RAA specimens were fixed in 10% formalin for 24 hours followed by 70% ethanol for 48 hours with subsequent paraffin embedding. Sections were cut and placed on slides for immunohistochemical staining. After routine antigen retrieval, the tissue sections were stained with an anti-SSEA3 antibody labeled with fluorescein isothiocyanate (FITC) and c-kit was detected with an anti-c-kit antibody labeled with tetramethylrhodamine (TRITC) for simultaneous characterization of c-kit and SSEA3 expression within native myocardium. Cellular nuclei were stained with 4',6-diamidino-2-phenylindole (DAPI). The results are presented in FIGS. 1A-1F.

Figure 1A:
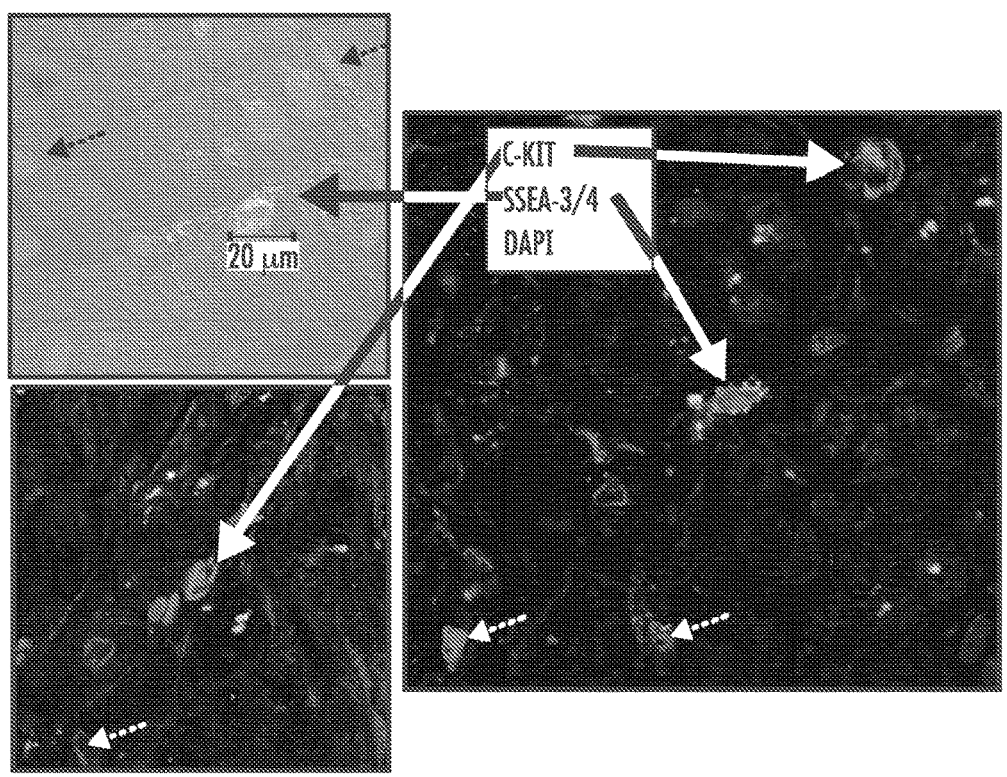

As shown in FIG. 1A, SSEA3-positive cells are shown in the upper left and right panels, each of which shows a single cell with green staining (solid white lines) indicative of SSEA3 expression. C-kit-positive cells are shown in the lower left and right panels, each of which shows a single cell with red staining (dashed white lines) indicative of c-kit expression. SSEA3-positive/c-kit-negative cells were found located in the interstitium between myocytes. C-kit-positive cells were found to be SSEA3-negative (the SSEA3-positive cells did not fluoresce red), and SSEA3-positive cells were found to be c-kit-negative (the c-kit-positive cells did not fluoresce green; see FIG. 1A, right panel). This demonstrated that in the native myocardium, c-kit-positive cells were not SSEA3-positive and SSEA3-positive cells were not c-kit-positive. As such, c-kit-positive and SSEA3-positive cells were two distinct cell phenotypes that coexisted within the native human myocardium. Furthermore, SSEA3-positive cells that were present upon in vitro expansion of cells (discussed herein below) were not culture-derived artifacts but existed within the native human myocardium.

Figure 1B:
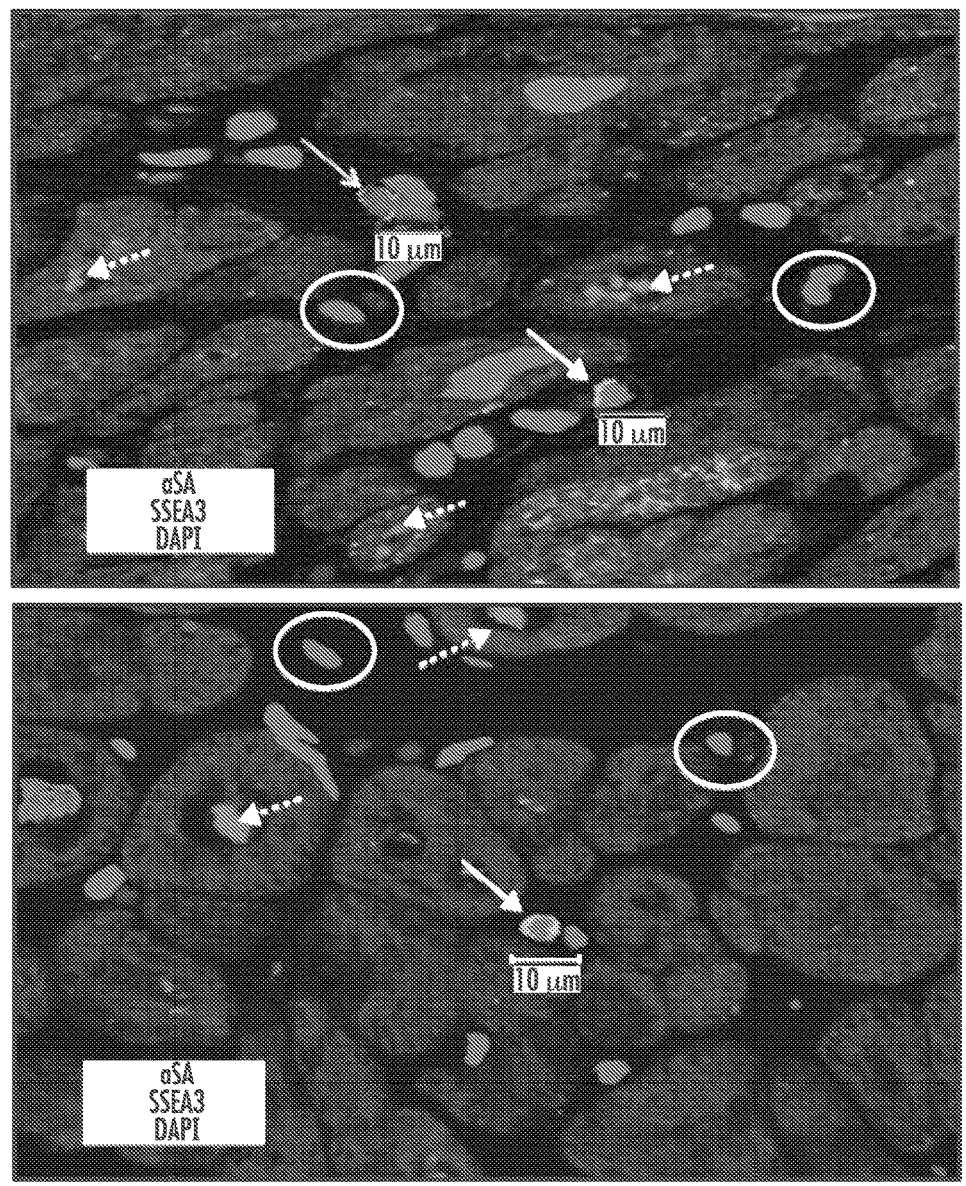

In FIG. 1B, SSEA3-positive (green fluorescence; solid white lines) cells are shown within the interstitium of the human myocardium. In FIG. 1B, myocytes were identified by alpha sarcomeric actin (aSA) staining with an anti-aSA antibody labeled with TRITC (red; dotted white lines). The SSEA3-positive cells were approximately 6-10 urn in diameter within the native myocardium, with very little cytoplasm and a large nucleus to cytoplasm ratio.

Figure 1C:
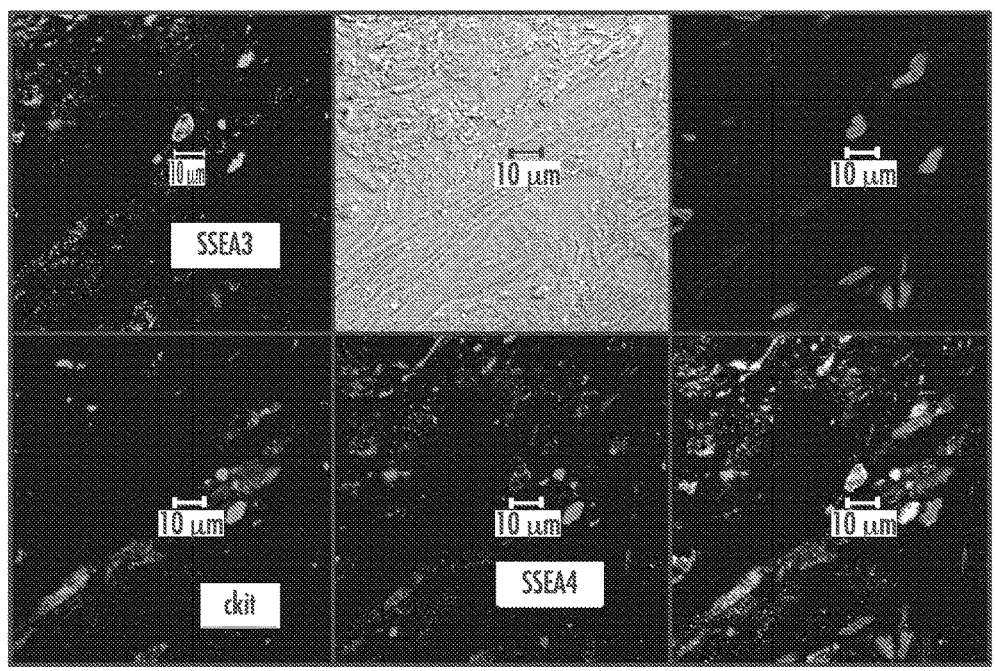

FIG. 1C is a series of confocal and microscopy images of SSEA3-positive (FITC; green or light gray in B&W; top left panel), SSEA4-positive (TRITC; red or gray in B&W; bottom center panel), and c-kit-negative (allophycocyanin (APC); magenta or light gray in B&W; bottom left panel) human myocardium cells. Nuclei were stained with DAPI and appear blue (gray in B&W) in the top right panel. The transmission pane (top center panel) showed the location of the SSEA3-positive/c-kit-negative cells, which were adjacent to the striated myocytes within the cardiac interstitium/adventitia. The bottom right panel is an overlay of the SSEA3, SSEA4, DAPI, and c-kit staining. As seen in FIG. 1C, SSEA3-positive and c-kit-negative cells were present within the native human myocardium, located in the interstitium between myocytes. C-kit-positive cells were SSEA3-negative by staining, with the positive controls being the SSEA3 positively stained cells themselves. This demonstrated that c-kit-positive cells were not SSEA3-positive in the native myocardium, and SSEA3-positive cells are not c-kit-positive in the native myocardium: they were two distinct cell phenotypes co-existing in the native human myocardium. Additionally, SSEA3-positive/SSEA4-positive cells were not culture-derived phenotypes but existed in the native human myocardium.

Figure 1D:
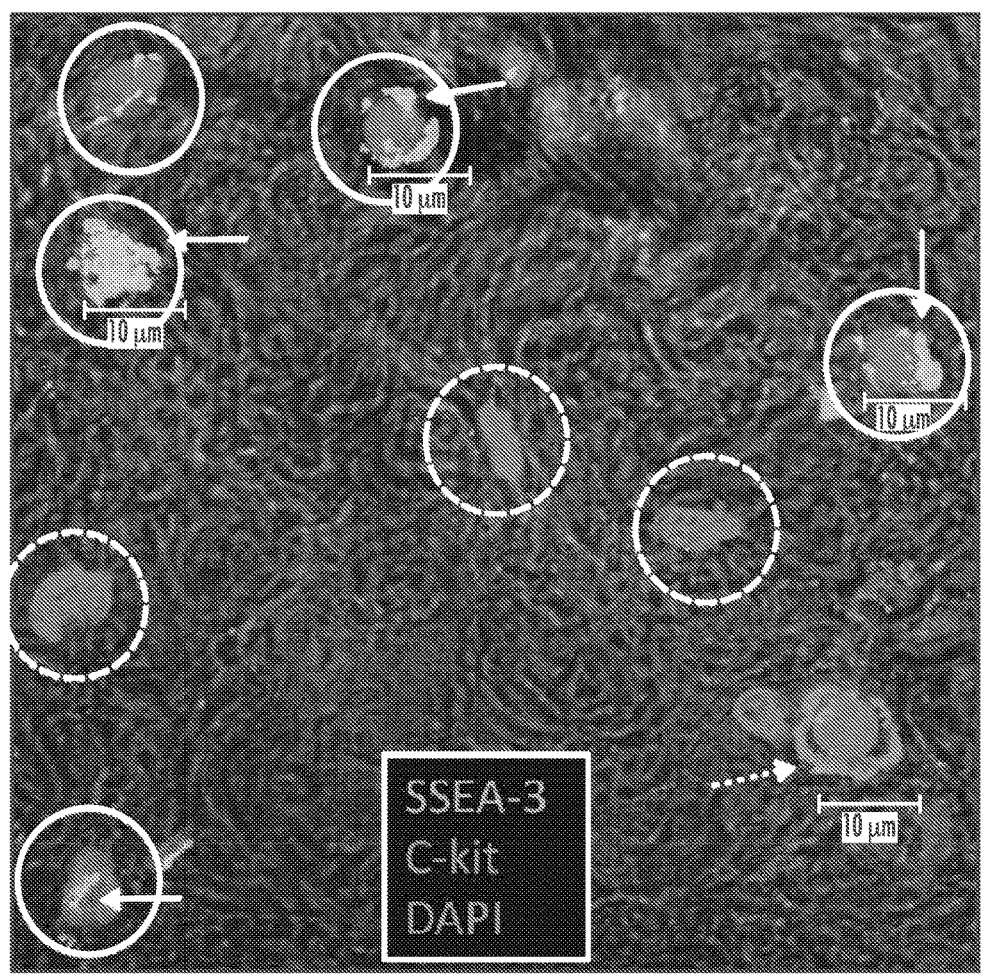

FIG. 1D is a confocal microscopy image showing SSEA3-positive (green or light gray in B&W; examples indicated by solid white arrows) and c-kit-positive (red or gray in B&W; example indicated by dotted white arrow) cells within a human pediatric RAA tissue specimen. SSEA3 was labeled with a rat IgM anti-human SSEA3 primary antibody (eBioscience, Inc.) and detected with an FITC-conjugated mouse anti-rat IgM secondary antibody, which showed SSEA3 positivity in green (light gray in B&W; examples indicated by solid white arrows). SSEA3-positive cells were c-kit-negative (examples shown with solid circles) as evidenced by the presence of a cell within the same field that stained positive with an anti-c-kit antibody labeled with TRITC (red or gray in B&W; example indicated by dotted white arrow). C-kit immunolabeling was done using a rabbit anti-human c-kit primary antibody (IgG; Dako) that was detected with a TRITC-labeled anti-rabbit IgG secondary antibody. Nuclei are shown in blue with DAPI labeling (examples noted in broken circles. SSEA3-positive cells did not express c-kit and thus were native to the myocardium (i.e., SSEA3 positivity in these cells was not a culture-derived artifact).

Figure 1E:
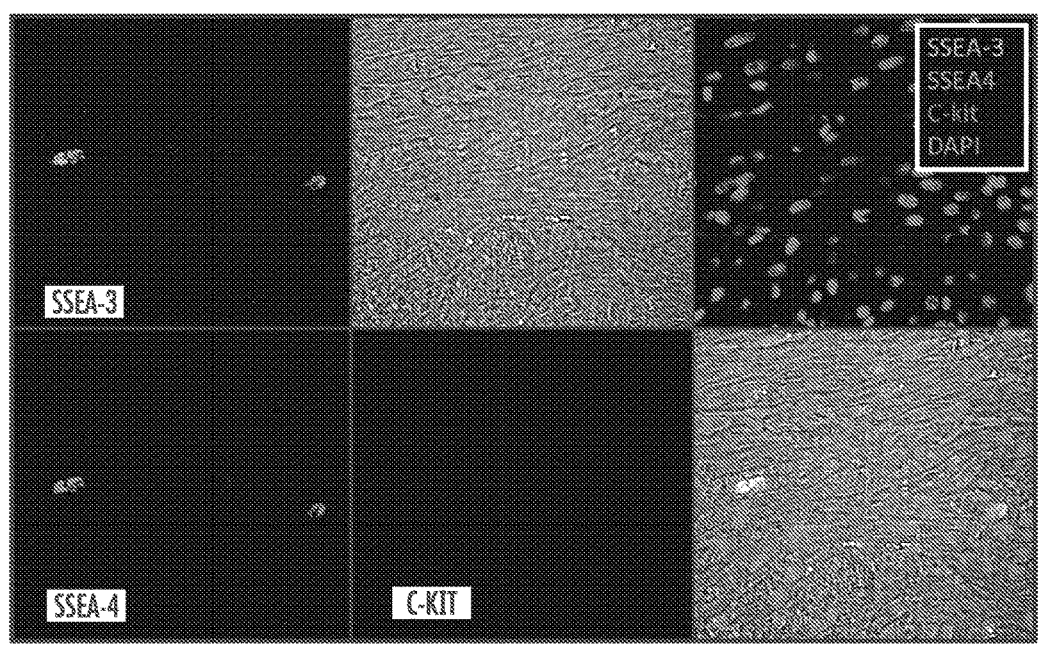

FIG. 1E is a series of confocal images of paraffin-embedded human right atrial tissue similar to those previously shown in FIGS. 1A-1D. Immunolabeling was performed in a similar fashion as presented herein above. SSEA3-positive cells were observed within the cardiac interstitium adjacent to striated myocytes identified by the transmission image (top center and bottom right panels). SSEA3-positive cells were also positive for SSEA4, which indicated true positive labeling of SSEA3 since SSEA3 and SSEA4 epitopes are generally present on the same membrane glycosphingolipid when SSEA3 is expressed by cells. Notably, SSEA4 can exist without SSEA3 as SSEA3 is downregulated more quickly than SSEA4 as cells differentiate. Thus, SSEA3 positivity was associated with a more primitive phenotype than that of SSEA3-negative/SSEA4-positive cells. Data confirming this observation, as was first established to be true in embryonic stem cells (see Liang et al., 2010), are illustrated herein below in FIGS. 19 and 20 with RT-PCR comparisons of SSEA3-positive and SSEA3-negative cells, among the latter of which would be SSEA3-negative/SSEA4-positive cells. Again, these cells did not have detectable c-kit expression.

Figure 1F:
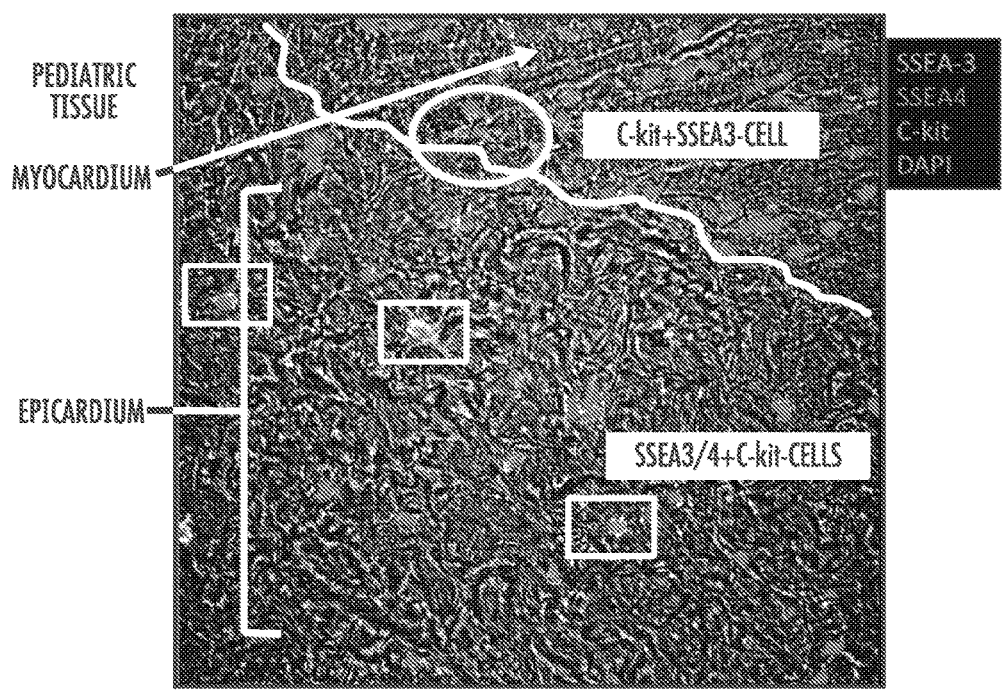
Figure 4:
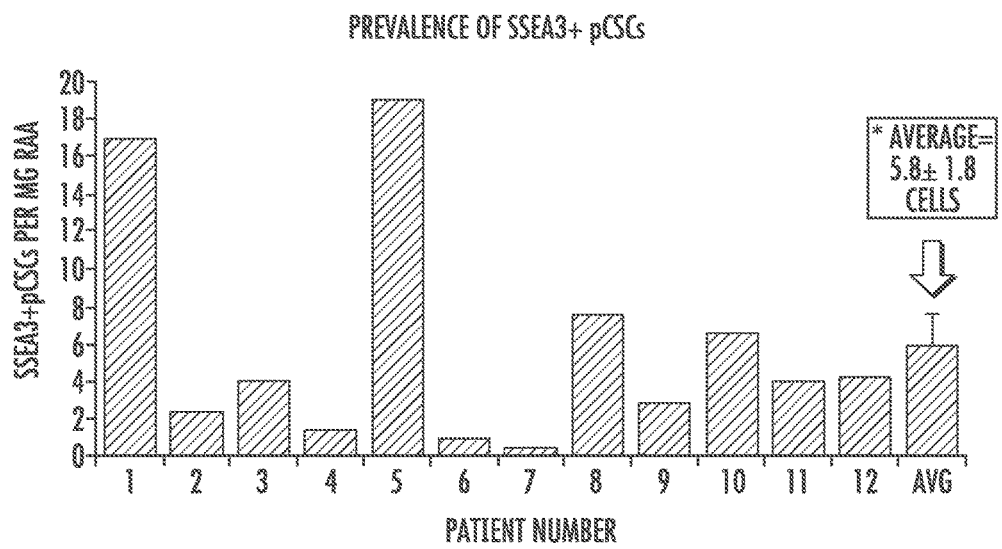

FIG. 1F is a confocal image showing SSEA3-positive/c-kit-negative cells observed within the epicardium in a sample of pediatric right atrial tissue. SSEA3-positive cells (stained green or gray in B&W) cells are also SSEA4-positive (stained purple/magenta or gray in B&W). The double positivity of SSEA3 labeled with FITC (green fluorescence) and SSEA4 labeled with secondary APC (purple/magenta) fluorescence is seen in FIG. 1F to form a pink overlay highlighting these cells (examples are boxed in FIG. 1F). A c-kit-positive/SSEA3/4-negative cell (circled) can be identified on the interface of the epicardial and striated myocardial junctions. Pediatric myocardium was found to have a much higher numbers of SSEA3-positive/c-kit-negative cells than adult myocardium. This differential prevalence between neonatal and adult myocardium is also depicted in FIG. 4 as patients 1 and 5 were both neonates while the remainder of the patients analyzed were adults. Accordingly, this differential prevalence in data accumulated both from direct immunohistochemical staining, as in this FIG. 1F, and in flow cytometry based quantification shown in FIG. 4, was confirmed.

Example 2

Sorting of Human RAA Cells into Subpopulations and Analyses Thereof

Figure 2:
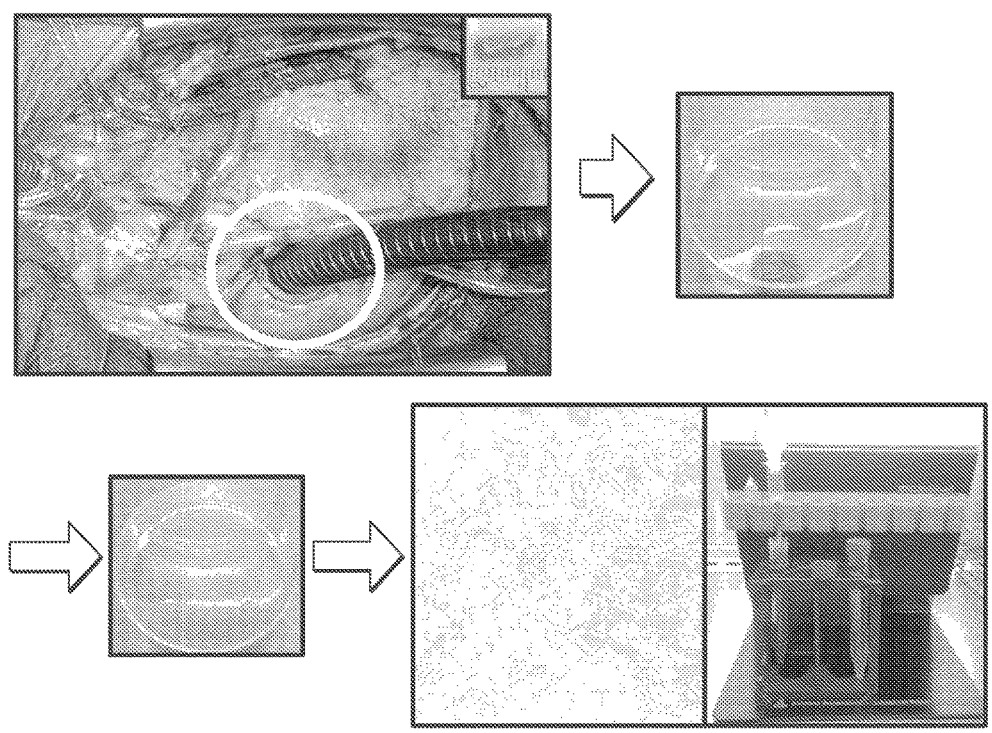

RAA cells were also sorted to identify subpopulations of cells that expressed various markers. FIG. 2 outlines an exemplary methodology for isolated and analyzing right atrial appendage (RAA) samples. The top left image is a typical open heart surgery in which the RAA sample is obtained from the site of bypass catheter insertion. An exemplary RAA (inset upper right corner of top left image) had a weight of 153 mg. The RAA was subjected to mechanical and enzymatic digestion for isolation of gross intracardiac cells and eventual immunomagnetic sorting of SSEA3-positive cells for in vitro expansion. The sorting procedure is outlined herein below in FIG. 15A. Although this RAA was large (153 mg), SSEA3-positive cells can also be isolated from much smaller right atrial tissue samples. SSEA3-positive cells have also been isolated from endomyocardial biopsies from the right ventricular septum. Successful isolations and expansions have been accomplished with samples of just a few milligrams in weight and 1-2 millimeters in diameter. FIG. 2 thus depicts the surgical harvest, mechanical mincing of the tissue with subsequent enzymatic digestion, isolation of unsorted cardiac cells which grow over the course of 10-14 days in vitro, and immunomagnetic sorting for SSEA3-positive cells using an application of validated, commercially available antibodies.

In particular examples, freshly digested RAA tissue and cell suspension were plated in growth medium for 18 hours post digestion, a time insufficient to have substantial expansion of the initially obtained intrinsic myocardial cellular populations. Cells and residual fragments were subjected to 10 minutes of enzymatic dissociation with TRYPLE™ brand dissociation reagent (Life Technologies, a division of Thermo Fisher Scientific Inc.) to get a largely single cell suspension, which was verified with suspension microscopy. Cells were washed twice with cold sterile Dulbecco's phosphate-buffered saline (DPBS) and blocked with 2% bovine serum albumin (BSA) for 20 minutes at 4° C. Cells were then transferred to two fluorescence-activated cell sorting (FACS) tubes and stained with an anti-SSEA3-e488-conjugated antibody (eBioscience, Inc.; a rat IgM-e488-conjugated isotype control was also employed) in sterile DPBS with 1% BSA for 40 minutes on ice in the dark. They were subsequently washed twice with cold sterile DPBS with 1% BSA, fixed in freshly made 1% paraformaldehyde (PFA), and stained with DAPI to identify nucleated cells and exclude residual debris and RBCs that remained. The results of representative analysis are presented in FIGS. 3 and 4.

Freshly isolated total cardiac cells (isolated 24 hours prior to sorting) from a freshly digested right atrial tissue sample were also analyzed by flow cytometry for presence of SSEA3-positive cells. A flow cytometry plot of freshly isolated total cardiac cells from a freshly digested right atrial tissue sample stained with a rat IgM isotype control antibody labeled with FITC and sorted with a resultant gate set for false positivity of 0.1% was prepared. A second flow cytometry plot under similar conditions as this was also prepared, except that the cells were stained with a rat anti-human SSEA3 monoclonal antibody (IgM; eBioscience, Inc.) labeled with FITC. SSEA3-positive cells were present in the innate myocardium, were not culture-derived, and approximated 1.0% of the intrinsic nucleated cardiac cells obtainable after prolonged enzymatic and mechanical disruption in this particular human sample obtained during cardiac surgery. This experiment demonstrated that SSEA3-positive cells, as shown in FIG. 1 and discussed herein above, were present in the innate myocardium and were not a culture-derived cell population. The relative percentage of these cells in the total cells that could be isolated by mechanical and enzymatic digestion varied widely as tissue sizes, component of contaminating blood cells, and duration of tissue digestion varied. The prevalence of SSEA3-positive cells in the human heart was measured by normalizing the total number of SSEA3-positive cells obtained from a piece of tissue to the weight of the myocardial specimen from which they came.

Figure 3A:
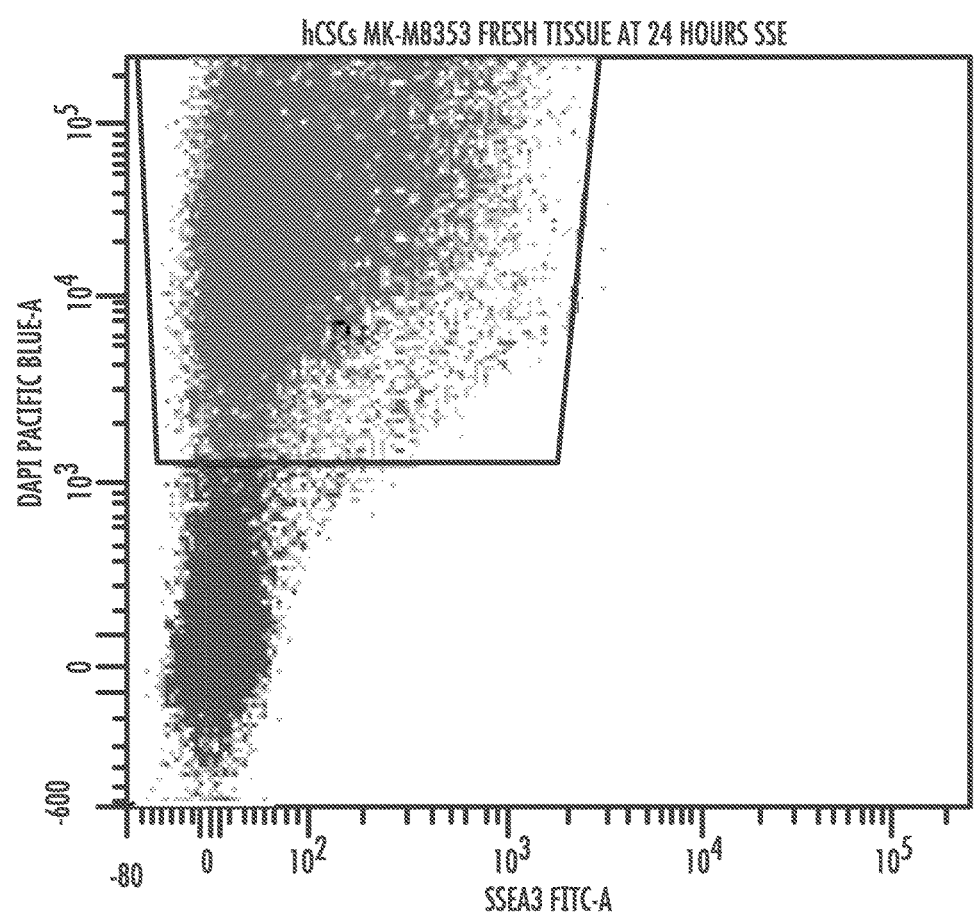
Figure 3B:
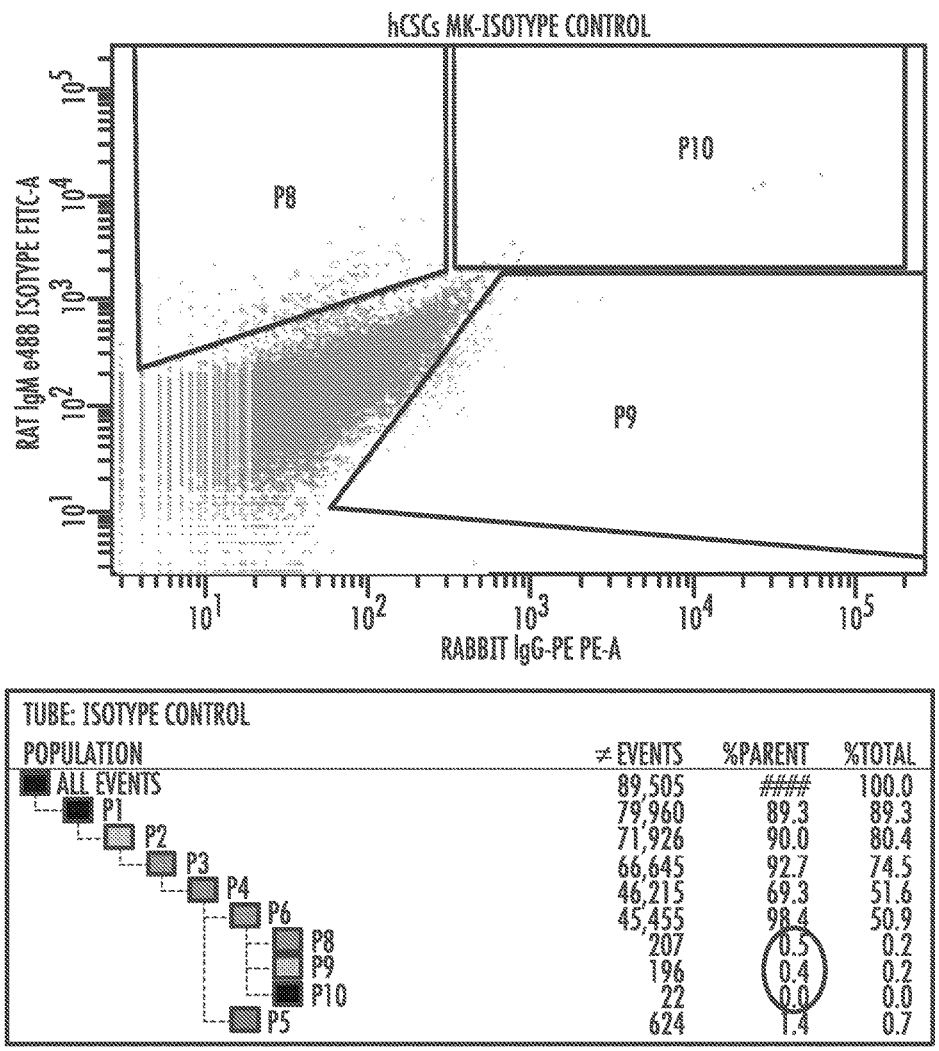
Figure 3C:
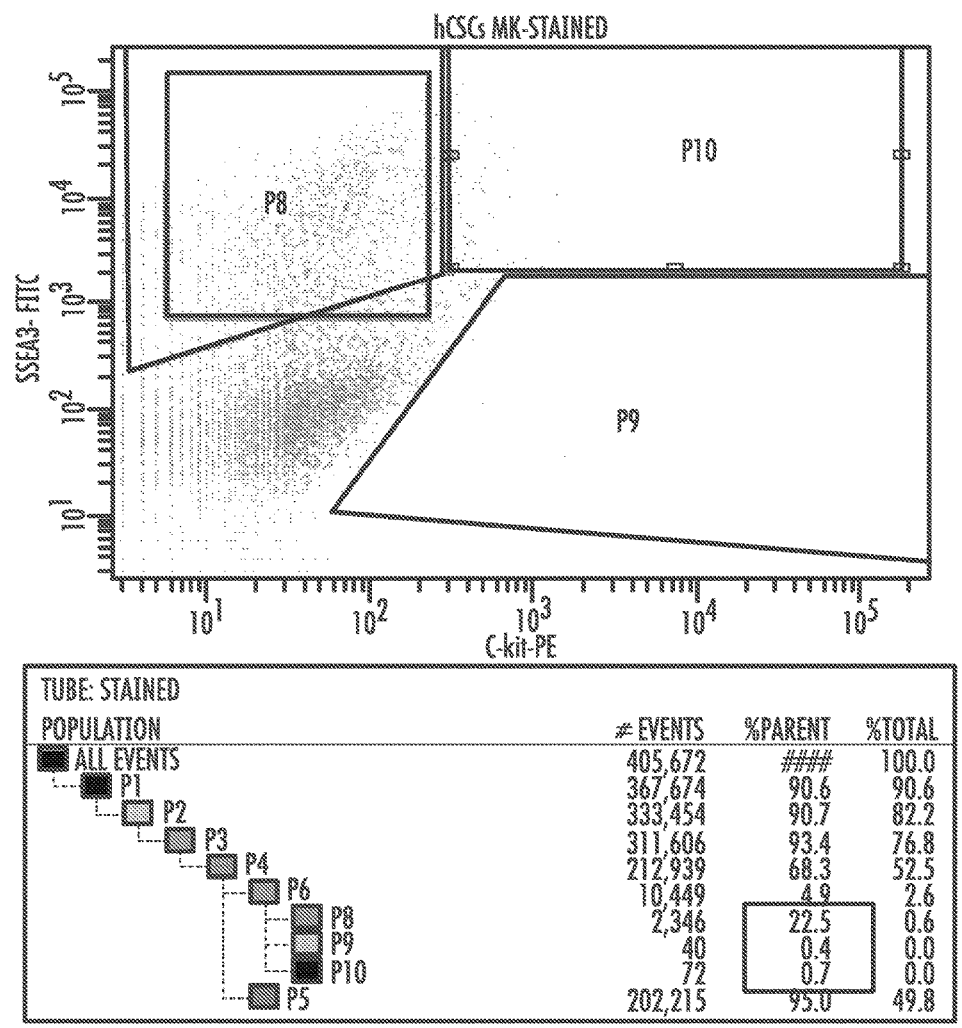

The results of further investigations to determine the number of SSEA3-positive cells per milligram of right atrial myocardium are presented in FIGS. 3A-3C and in FIG. 4. FIGS. 3A-3C are flow cytometry plots of cells obtained from cardiac tissue, which were fixed in 4% paraformaldehyde (PFA) prior to blocking and subsequent immunolabeling. FIG. 3A shows DAPI positive events only (to exclude contaminating red blood cells which did not have nuclei) that were used for analysis in establishing prevalence of SSEA3-positive cells immediately after myocardial processing and digestion shown in FIGS. 3B and 3C as well as in FIG. 4. Cells were divided for FACS staining versus isotype control antibody labeling to establish analysis gates. Positive gates were set according to isotype control staining which is shown in FIG. 3B. Gates were set for isotype control false positives not in excess of 1% of the population which is shown on the lower panel (P8-P10 gates). Only cells negative for CD45 are shown as CD45-positive cells were excluded from the analysis by appropriate gating to rule out hematopoietic origin of the intracardiac SSEA3-positive cells.

FIG. 3C is a flow cytometry plot of cells obtained from freshly digested tissues that were analyzed for presence of SSEA3, c-kit, and CD45 by flow cytometry. CD45-positive hematopoietic cells were also excluded from this analysis as described herein above. Shown is the positive labeling of SSEA3-FITC and c-kit-PE (and negative for CD45-APC). SSEA3-positive cells in the P8 gate (red box) were seen not to possess detectable levels of c-kit expression. The absolute number of SSEA3-positive cells isolated from this particular large right atrial appendage is shown by the P8 gate (i.e., 2,346 cells' see the lower panel).

FIG. 4 shows the results of analyses of twelve (12) human cardiac tissue specimens that were digested as per the method disclosed herein above and analyzed by flow cytometry for the presence of SSEA3-positive/c-kit-negative/CD45-negative cells expressed as the number of such cells per milligram of right atrial myocardium. Cells obtained from enzymatic digestion were separated using a rat anti-SSEA3 primary antibody (IgM; eBioscience, Inc.) labeled with FITC, a rabbit and human c-kit primary antibody labeled with PE (Santa Cruz Biotechnology, Inc. C19), and a mouse anti-human CD45 primary antibody labeled with APC (eBioscience, Inc.) versus isotype control staining, which allowed establishment of positive gating. Cells were fixed with 4% PFA prior to staining and labeled with DAPI nuclear stain to count only nucleated cells. Absolute positive counts from gates such as the P8 gate in FIG. 3A were averaged and normalized to the weight of the initial cardiac specimen from which the cells were isolated. The mean numbers of SSEA3-positive/c-kit-negative/CD45-negative cells per milligram of right atrial tissue from 12 separate patients are shown in FIG. 4. SSEA3-positive/c-kit-negative/CD45-negative cells were estimated to have a prevalence of 5.8±1.8 cells per milligram of human right atrial tissue. Notably, Patients 1 and 5 were pediatric patients, suggesting that there were differences in the prevalence of SSEA3-positive/c-kit-negative/CD45-negative cells between adult and pediatric patients, and further that these cells might decrease with aging. Removing these two samples from the data set results in reduction of the prevalence of SSEA3-positive c-kit-negative cells within adult right atrial tissue to approximately four (4) cells per milligram of adult right atrial myocardium.

Example 3

Expansion of Human RAA Subpopulations and Analyses Thereof

Right atrial appendage specimens were obtained under IRB approval from patients undergoing open heart, on pump, coronary artery bypass surgery at Jewish Hospital in Louisville, Ky., United States of America. Right atrial appendages were harvested from the site of bypass catheter insertion and transported to the cell processing lab under sterile conditions on wet ice. The tissue was washed several time with ice cold PBS to remove gross blood. Adipose tissue was then resected manually from the external surface of the tissue with subsequent repeated washing in cold PBS. The tissue was transferred to a 35 mm culture dish with addition 0.5 mL ice cold Ham's F12 media. The tissue was then manually minced to obtain fragments<1 mm³. Fragments were transferred to a 50 mL conical tube with addition of 20 mL of ice cold Ham's F12 media and allowed to sediment over 10 minutes. The supernatant was removed and discarded. The tissue fragments were then incubated on a shaking incubator at 37° C. in 10 mL Worthington Collagenase type II solution for 1 hour. After an hour, 5 mL additional collagenase solution was added and the tube returned to the incubator for another hour. At the end of the incubation, the solution with released cells and residual tissue fragments were pipetted gently with a large orifice pipette tip to promote suspension of free cells, and the tissue fragments were allowed to settle over 5-10 minutes. The supernatant was pipetted gently over a 100 μm filter to remove cardiomyocytes and large debris. The residual tissue fragments were washed in another 20 mLl of cold Ham's F12 media and again allowed to settle with pipetting of the supernatant containing additionally released cells over the 100 μm filter, combining them with the initial fraction. The filter was inverted over the primary tube with residual tissue fragments with washing of contents back into the tube with the residual fragments. An additional round of enzymatic digestion was performed if there was much residual, undigested tissue. The solution of released cells was centrifuged at 300×g for 10 minutes with discarding of the supernatant. The cells were washed in full growth media consisting of 60% mTESR™ 1-(STEMCELL™ Technologies) with 20% FBS and 40% basal media, which was Ham's F12 (GIBCO®), 10% FBS (Thermo Scientific HYCLONE™), 10 ng/mL Recombinant Human bFGF (PeproTech), 0.2 mM L-glutathione (Sigma-Aldrich), and 5 ng/mL human erythropoietin (Sigma-Aldrich). The supernatant was discarded and the cells were resuspended in 60% mTESR™ 1 and 40% basal media by volume and plated in a 6-well plate for passage 0 initial expansion. Media was changed at 24 hours completely. Additional media changes were performed every 3-4 days or if necessitated by visual examination of the culture. Cells were expanded until 70% confluence at which time they were trypsinized and passaged to T75 Flasks for additional subconfluent expansion. Media was added or changed partially every 3-4 days for the remainder of the culture process. Cells were passaged 1-2 times prior to any analyses in unsorted gross myocardial cells or immunomagnetic sorting for human SSEA3 using a primary antibody rat IgM anti-human SSEA3 conjugated with PE (eBioscience, Inc.) and a secondary antibody mouse IgG conjugated with immunomagnetic beads reactive to the fluorophore PE (Miltenyi Biotec) according to manufacturer's recommendations. Resultant positively selected SSEA3-positive cells (EA-CPCs) were replated at subconfluence and allowed to expand in vitro or were utilized immediately for assays respectively.

Example 4

Sorting of In Vitro Expanded Human RAA Subpopulations

In vitro-expanded unsorted myocardial cells were then analyzed by FACS (BD-LSR flow cytometer with FACS DIVA software; BD Biosciences, San Jose, Calif., United States of America) and/or MOFLOW® System (Beckman Coulter Inc.) sorting. The results are presented in FIGS. 5-11.

Figure 5A:
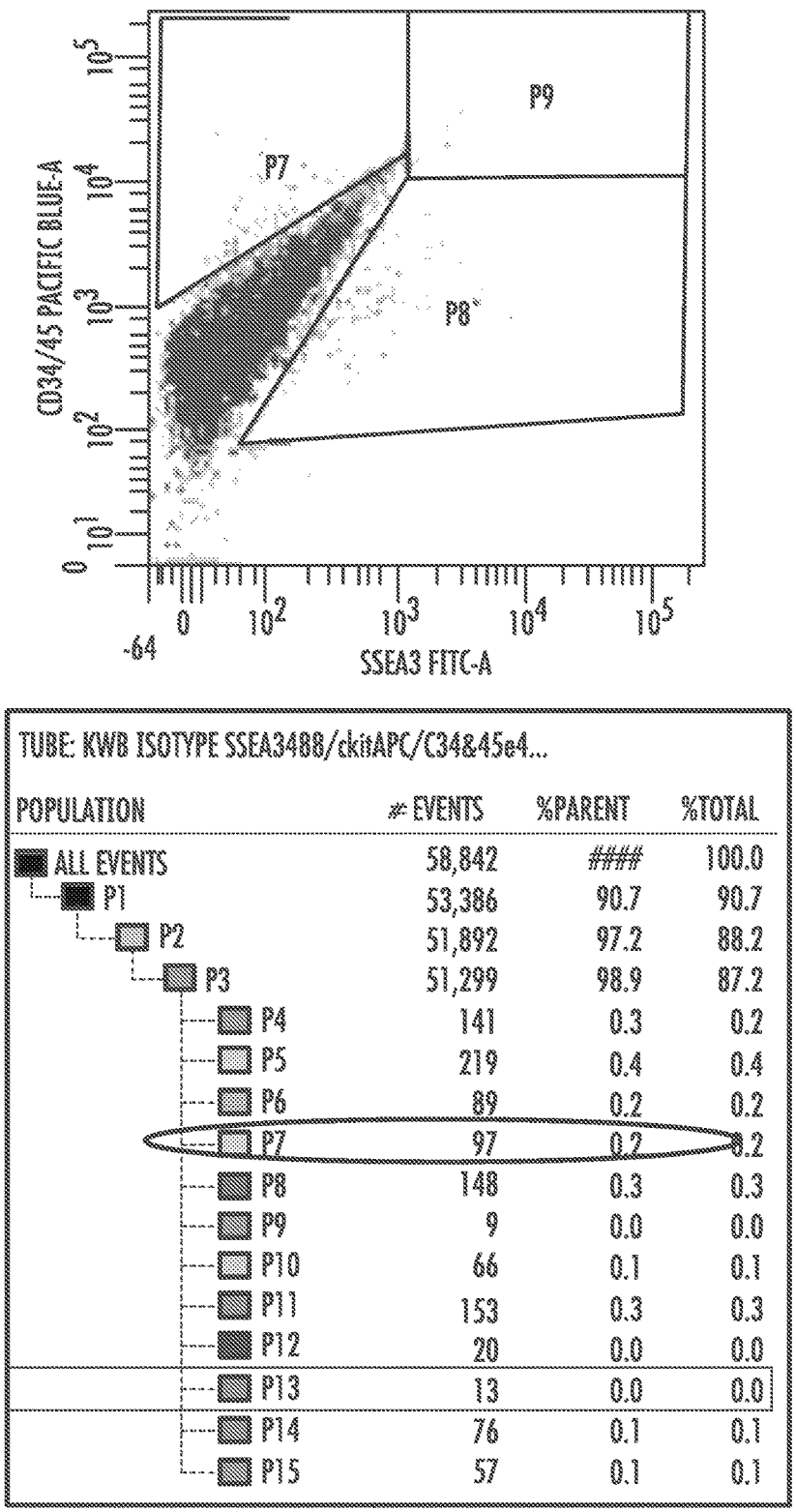

FIG. 5A is a FACS flow cytometry plot of unsorted in vitro expanded myocardial cells showing isotype control mouse monoclonal IgG antibodies (eBioscience, Inc.) labeled with e450 (0.2% false positivity by set gating) and isotype control rat IgM monoclonal antibody (eBioscience, Inc.) labeled with FITC (0.3% false positivity by set gating). In FIG. 5A, the expression of CD34 and CD45 markers on SSEA3-positive cardiac cells was investigated as an indication that these cells were from bone marrow/hematopoietic origin.

Figure 5B:
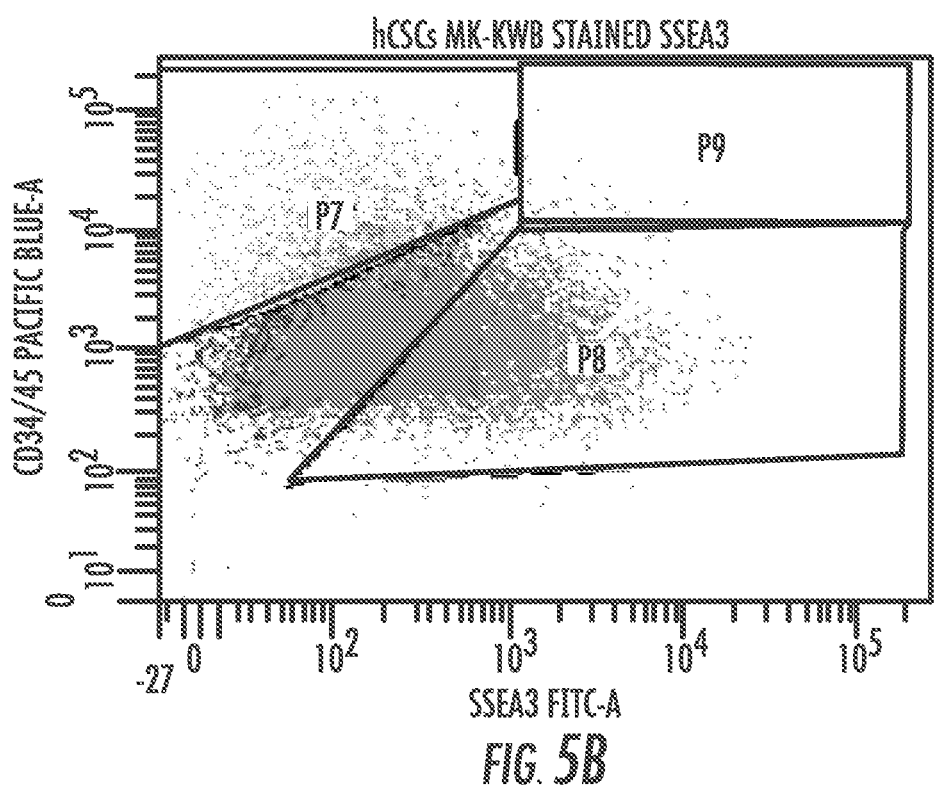

FIG. 5B is a flow cytometry plot of unsorted in vitro expanded myocardial cells, with isotypes as in FIG. 5A, showing that CD34-positive/CD45-positive cells constituted approximately 7% of the unsorted population (see the P15 gate circled in the lower panel) and SSEA3-positive cells approximated 7-27% of the unsorted population (7% by measuring only the brightest cells using conservative gating (magenta staining in the P8 gate), 27% by gating very tightly to include all SSEA3 positivity above that of isotype control even those very dimly positive (total cells in the P8 gate)) 7 days after initial isolation. These SSEA3-positive cells, highlighted by the conservative magenta color gating in P8, showed no detectable fluorescence for the markers CD34 and CD45. Additionally, the P9 gate showed no double positive cells with respect to set isotype controls. CD34-positive/CD45-double positive cells within the culture remained as contaminants from the original tissue digestion. These cells can be removed with serial media changes and passaging over time and/or with SSEA3-positive magnetic immunoselection. As shown in FIGS. 5A and 5B, SSEA3-positive cells were not CD34-positive or CD45-positive, and were thus not of hematopoietic lineage or derived from blood. Rather, they were intrinsic cardiac cells. It is noted that these cells were not initially positive as shown in FIG. 3C and do not become CD34-positive or CD45-positive in vitro.

In vitro-expanded myocardial cells were also analyzed using the MOFLOW® flow cytometry system (Beckman Coulter Inc.). Cells were trypsinized and labeled with an anti-human SSEA3 conjugated with PE (eBioscience, Inc.) in combination with alternate monoclonal antibodies to markers such as c-kit, CD90, SSEA1. Differential flow sorting was performed for isolation of SSEA3-positive fractions which were subjected to qPCR analyses.

Figure 6:
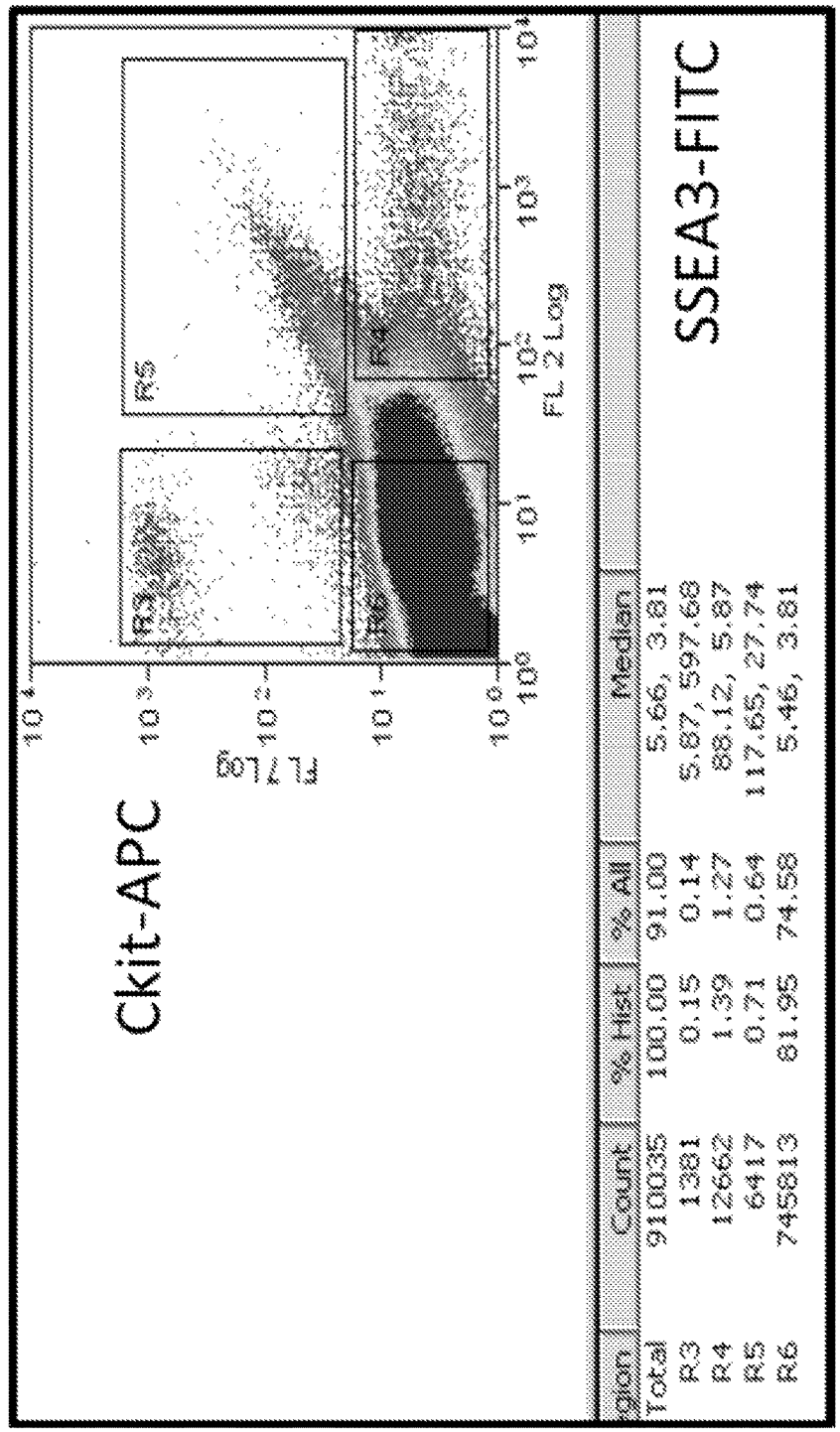

The results are presented in FIG. 6. Cells were labeled with a rat anti-human SSEA3 primary antibody (eBioscience, Inc.) labeled with PE and an anti-human c-kit N-terminal antibody (mouse monoclonal IgG eBioscience, Inc.; clone YB5.B8) labeled with APC. Two populations of c-kit-positive cells were seen, brightly positive (R6 gate) and dimly positive (R3 gate), neither of which were SSEA3-positive. The R5 gate included cells with double positivity for SSEA3 and c-kit that was not above isotype controls in nearly one million events that were analyzed. The P4 gate was FACS sorted with subsequent RNA isolation and RT-PCR analyses for selected target gene expression. SSEA3-positive/c-kit-negative cells were compared to unsorted cells for validation of the hypothesis that SSEA3 positivity should result in selection of cells with a more primitive phenotype and higher expression of stem cell/progenitor associated genes and markers. These data are presented in detail in FIGS. 12, 13, 19, and 20.

Figure 7A:
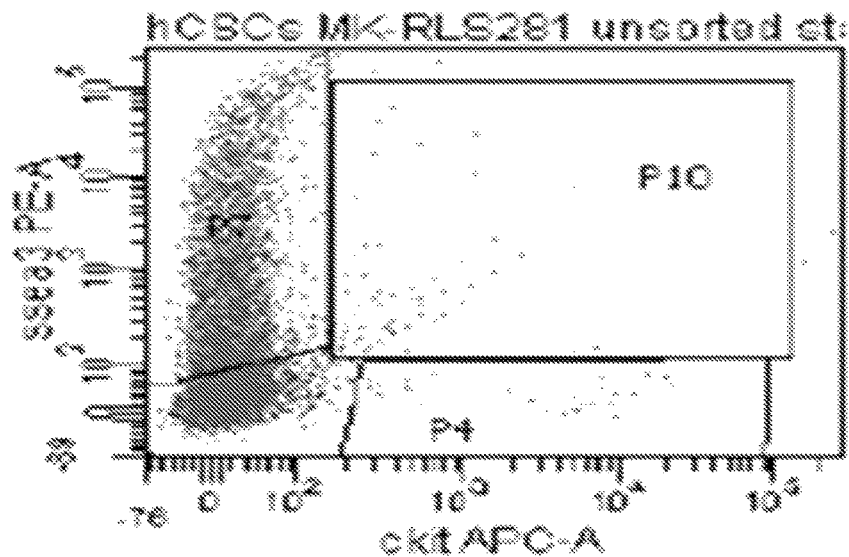
Figure 7B:
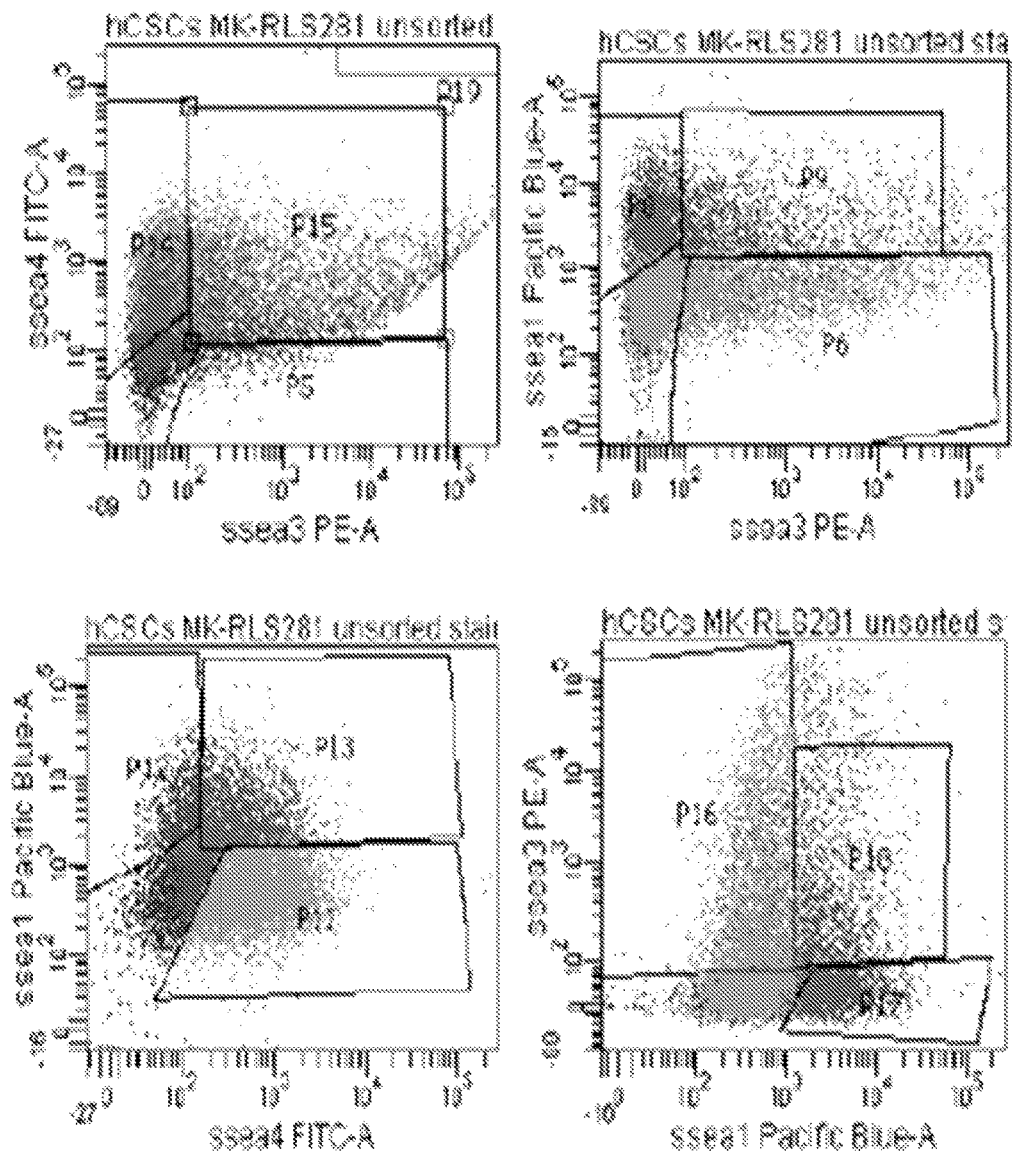

FIGS. 7A and 7B are flow cytometry plots of unsorted 10 day-expanded myocardial cells showing SSEA3-positive cells were negative for c-kit. In FIG. 7A, c-kit-positive cells from the P4 gate of FIG. 6 were further sorted, with SSEA3-positive/c-kit-negative cells appearing in the P7 gate (top left gate; bottom panel). There was no notable SSEA3-positive/c-kit-positive population in the P10 gate above that of the isotype controls (see the lower panel. Again, SSEA3-positive cardiac cells did not detectably express c-kit by flow cytometry. This fraction was what subsequently underwent SSEA3-positive MACS sorting to select the most highly positive cells for SSEA3.

Further analysis of the P7 gate of FIG. 7A is summarized in FIG. 7B. FIG. 7B is a series of flow cytometry plots of unsorted 10 day-expanded myocardial cells stained with an anti-human SSEA3 antibody (eBioscience, Inc. rat monoclonal IgM) labeled with PE vs. a mouse monoclonal IgG anti-human SSEA4 antibody labeled with FITC (see the top left plot). SSEA3-positive cells are shown to largely co-express SSEA4, indicating a largely undifferentiated state. SSEA3 vs. SSEA1 staining is shown in the top right plot, which indicated that of the approximate 27% of the cells that expressed SSEA3, about one-third co-expressed SSEA1, indicating that the sorted cells comprised subpopulations in a continuum of relatively undifferentiated cells and others with more differentiated phenotype indicated by SSEA1 expression. As can be seen by the color gating of SSEA1-positive (in brown), there were SSEA1-positive/SSEA4-positive/SSEA3-negative cells in the P14 gate of the top left plot, with even more differentiated phenotype in the expanding unsorted population. A continuation of this was seen with SSEA1-positive/SSEA3-negative/SSEA4-negative cells seen in the P12 gate of the bottom left plot, implying that the founding undifferentiated progenitor cells expressing SSEA3, originally isolated from the myocardium, had varying levels of spontaneously differentiating subpopulations as they expanded in culture, hence purification of the most undifferentiated progenitors with SSEA3 positivity could be accomplished. Evidence for the more primitive phenotype of cardiac cells expressing SSEA3 is extensively shown below with RT-PCR analyses, immunostaining, and western blot analyses for various stem cell-associated phenotypic markers. This approach established an expression profile of SSEA3-positive cells compared to SSEA3-negative cells isolated from cardiac tissue.

Figure 8A:
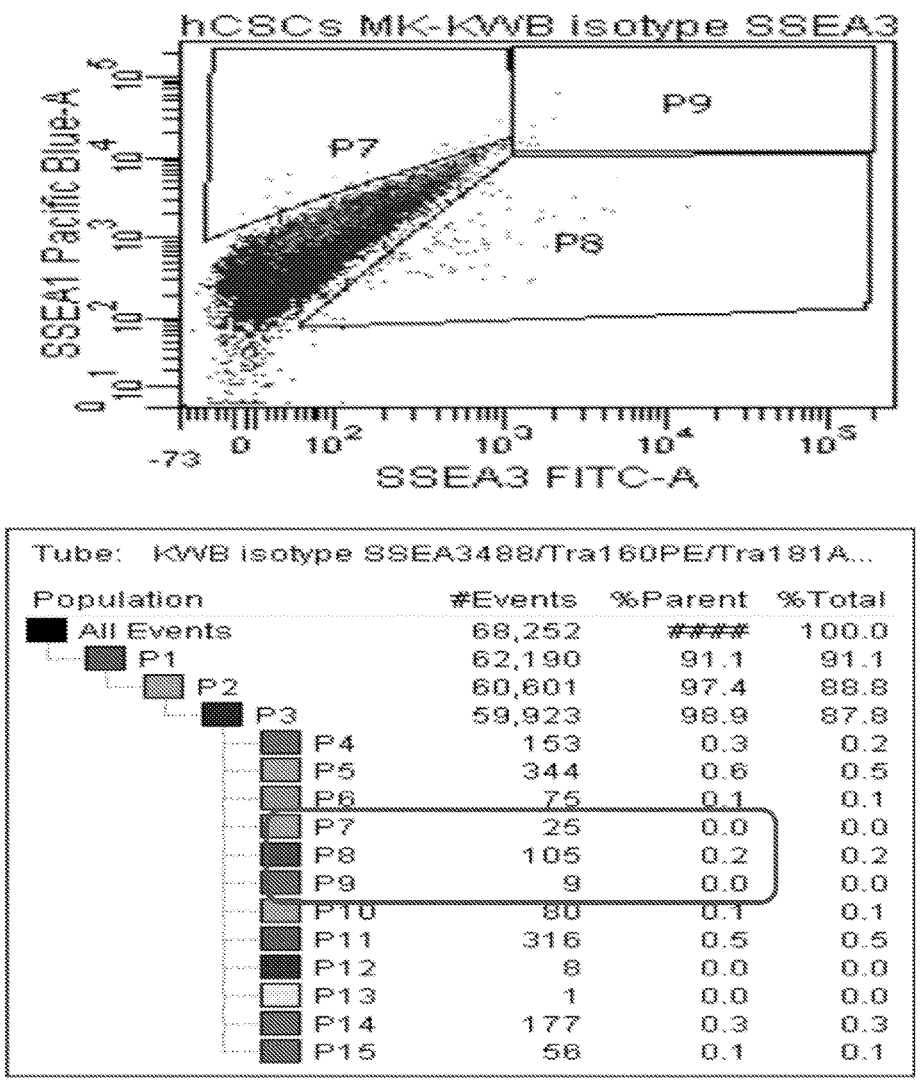
Figure 8B:
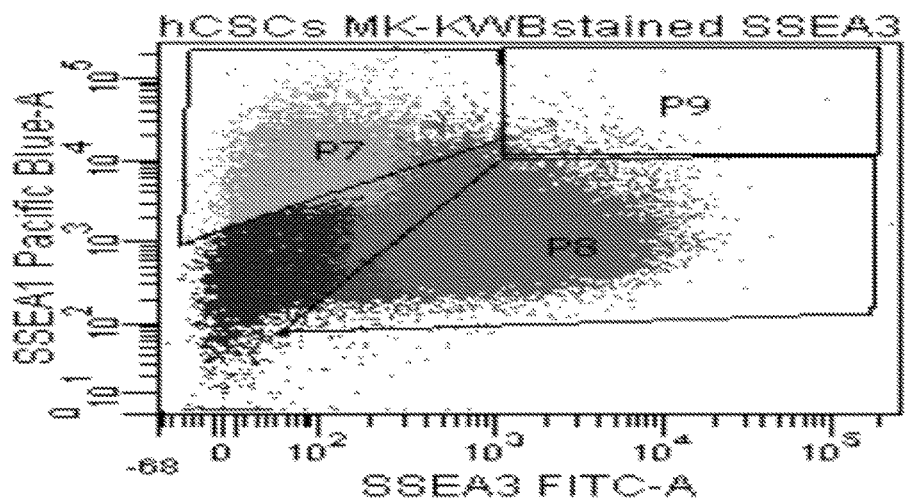

Additional flow cytometry plots are presented in FIGS. 8A and 8B. FIG. 8A shows isotype control mouse monoclonal IgM antibodies (R&D Systems, Inc.) labeled with e450 (0.0% false positivity by set gating) and isotype control rat IgM monoclonal antibody (R&D Systems, Inc.) labeled with FITC (0.2% false positivity by set gating). FIG. 8B is a flow cytometry plot of unsorted myocardial cells with isotypes represented as in FIG. 8A, showing SSEA1-positive cells approximated 6.5% (see the upper panel, P7 gate) and SSEA3-positive cells approximated 8-27% of the unsorted population 7 days after initial isolation. These SSEA3-positive cells, by the gating in P8, showed minimal if any fluorescence for the marker SSEA1, suggesting that the SSEA3-positive cells were present in an undifferentiated state. This patients SSEA3-positive cells did not have evidence of SSEA1 expression, indicating that SSEA3-positive cells could be heterogeneous with respect to SSEA1, and/or could become positive in vitro with spontaneous differentiation and/or loss of a progenitor phenotype.

Thus, EA-CPCs appeared to be heterogeneous for SSEA1 expression. The EA-CPCs in FIG. 8B did not show positivity for SSEA1. This fact led to the flow sorting and PCR comparison of SSEA3-positive/SSEA1-positive and SSEA3-positive/SSEA1-negative cells to see if one subpopulation was superior to the other with respect to OCT4/NANOG/NKX2.5 expression.

Figure 9:
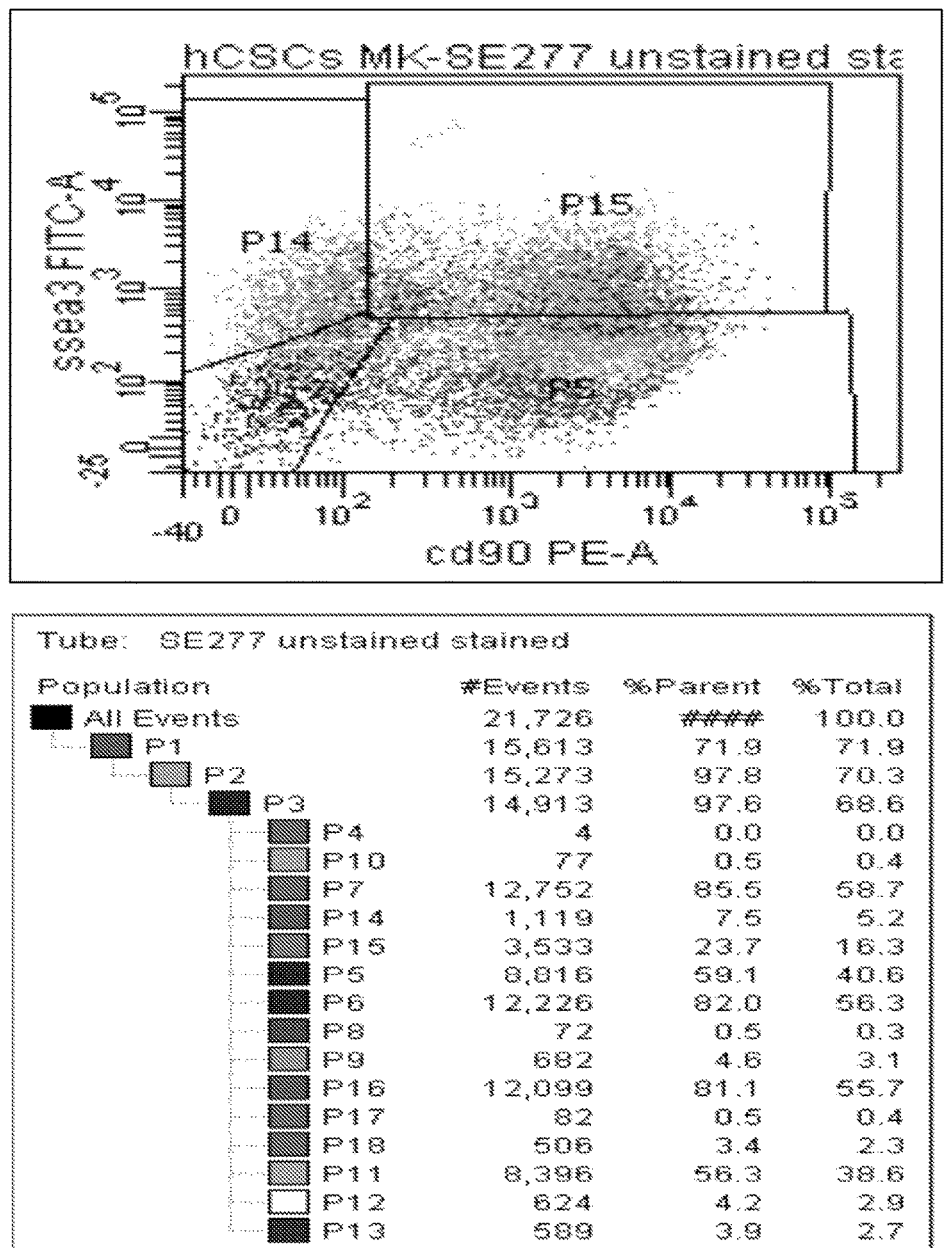
Figure 14:
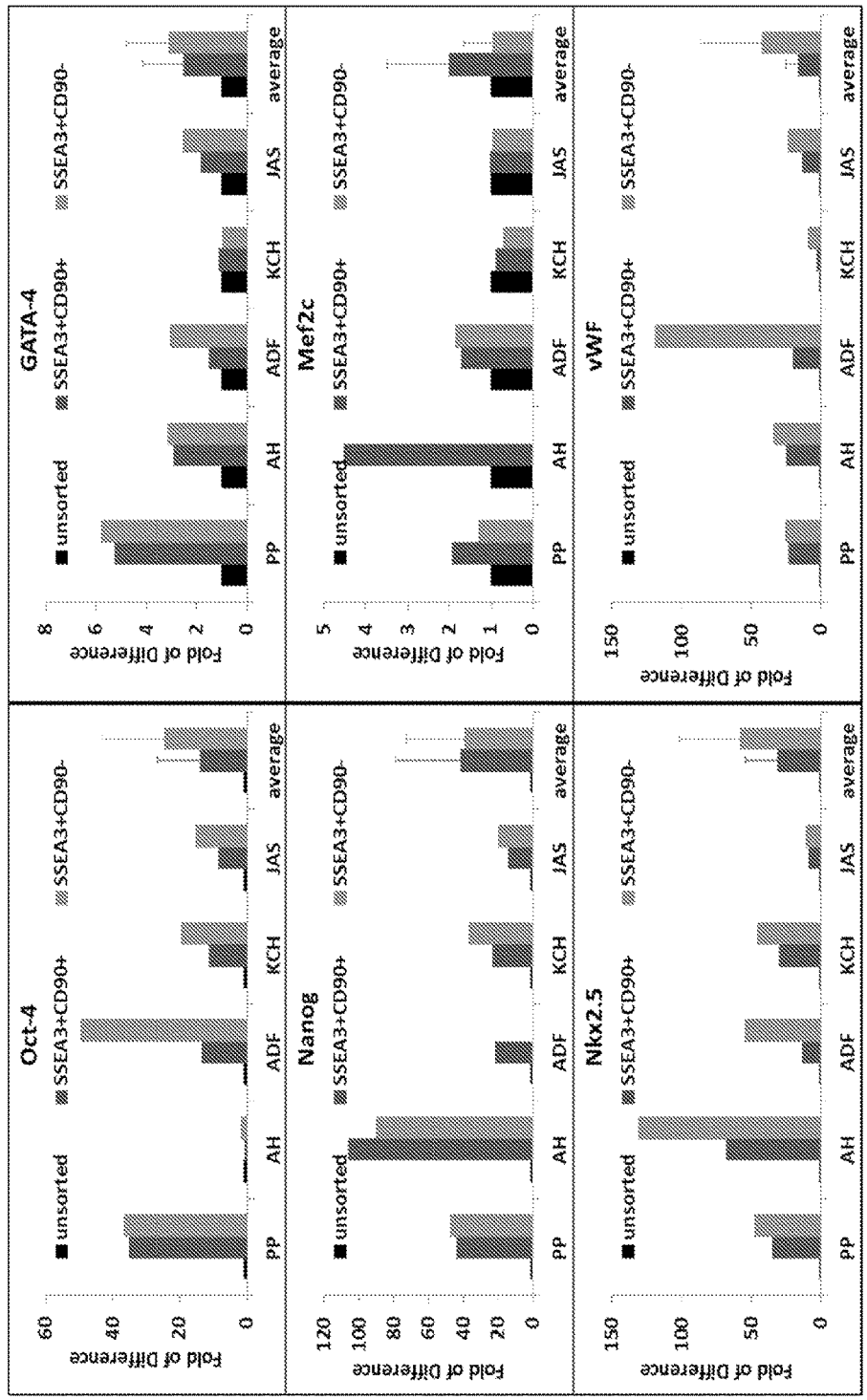

FIG. 9 is a flow cytometry plot of unsorted myocardial cells showing expression of SSEA3 and the mesenchymal marker CD90 (Thy-1). FIG. 9 shows that SSEA3-positive cells illustrated by the P14 and P15 gates were heterogeneous for the marker CD90. Gating was set for less than 1.0% false positivity. The P14 gate identified SSEA3-positive/CD90-negative cells, whereas the P15 gate included a population of SSEA3-positive/CD90-positive cells. RT-PCR comparison was performed between SSEA3-positive/CD90-negative and SSEA3-positive/CD90-positive cells. The results of which are shown in FIG. 14 below.

Figure 10:
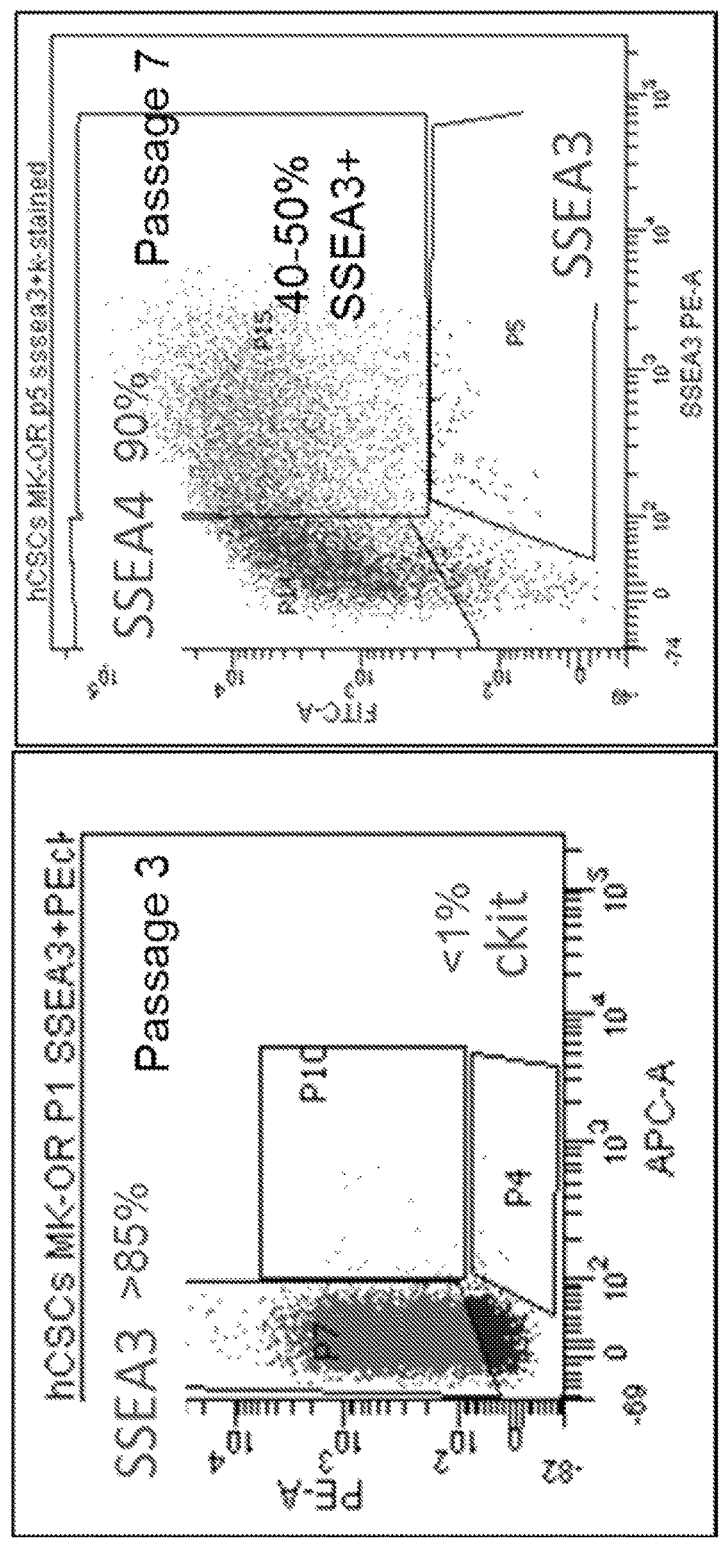

FIG. 10 is a flow cytometry plot of magnetically-immunoselected (MACS) SSEA3-positive cells showing greater than 80% enrichment of SSEA3-positive cells stained with a PE-labeled anti-SSEA3 antibody after the third passage with negative expression of c-kit (less than 1%; detected with an APC-labeled anti-c-kit antibody) as measured by the immunofluorescence FACS protocol disclosed herein (left panel). The cells were expanded to passage 7 and reanalyzed for maintenance of SSEA3 and SSEA4 expression. The P15 gate illustrated that 60% of the population maintained expression of SSEA3 (PE) and SSEA4 (FITC). Approximately 35% of the post-SSEA3-positive sorted population had lost SSEA3 expression and only maintained expression of SSEA4 measured by FACS (right plot). This indicated, as was observed in the immunohistochemistry and early flow cytometric analyses described herein above, that SSEA3-positive cells were also SSEA4-positive. With prolonged culture or in vitro expansion, SSEA3 positivity diminished. SSEA4 positivity persisted longer than did SSEA3 positivity.

Stated another way, SSEA3 expression more quickly than SSEA4 expression, with an accompanying loss of a stein cell/progenitor phenotype. This expression pattern has also been shown to occur in embryonic stem cells with spontaneous or induced differentiation (see Liang et al., 2010). As is shown by subsequent Figures in which SSEA3-positive cells were compared to SSEA3-negative cells both at early and late passage, SSEA3 positivity conferred a more primitive phenotype with higher expression of pluripotency associated factors and early cardiac progenitor markers than SSEA3 negativity.

The SSEA3-negative subset of cells included SSEA3-negative/SSEA4-positive cells. For this reason, SSEA4 was viewed as a co-positive marker indicative of true SSEA3-positive staining, but did not matter in terms of stem cell/progenitor phenotypic selection in the instantly described methodology. SSEA3 expression appeared to be more primitive and provided superior stem cell/progenitor selection than did SSEA4 positivity alone. C-kit remained undetectable at early (right panel, P4 and P10 gates) and late passage (less than 1%) in SSEA3-positive cells as evidenced by flow cytometric analysis.

Figure 11:
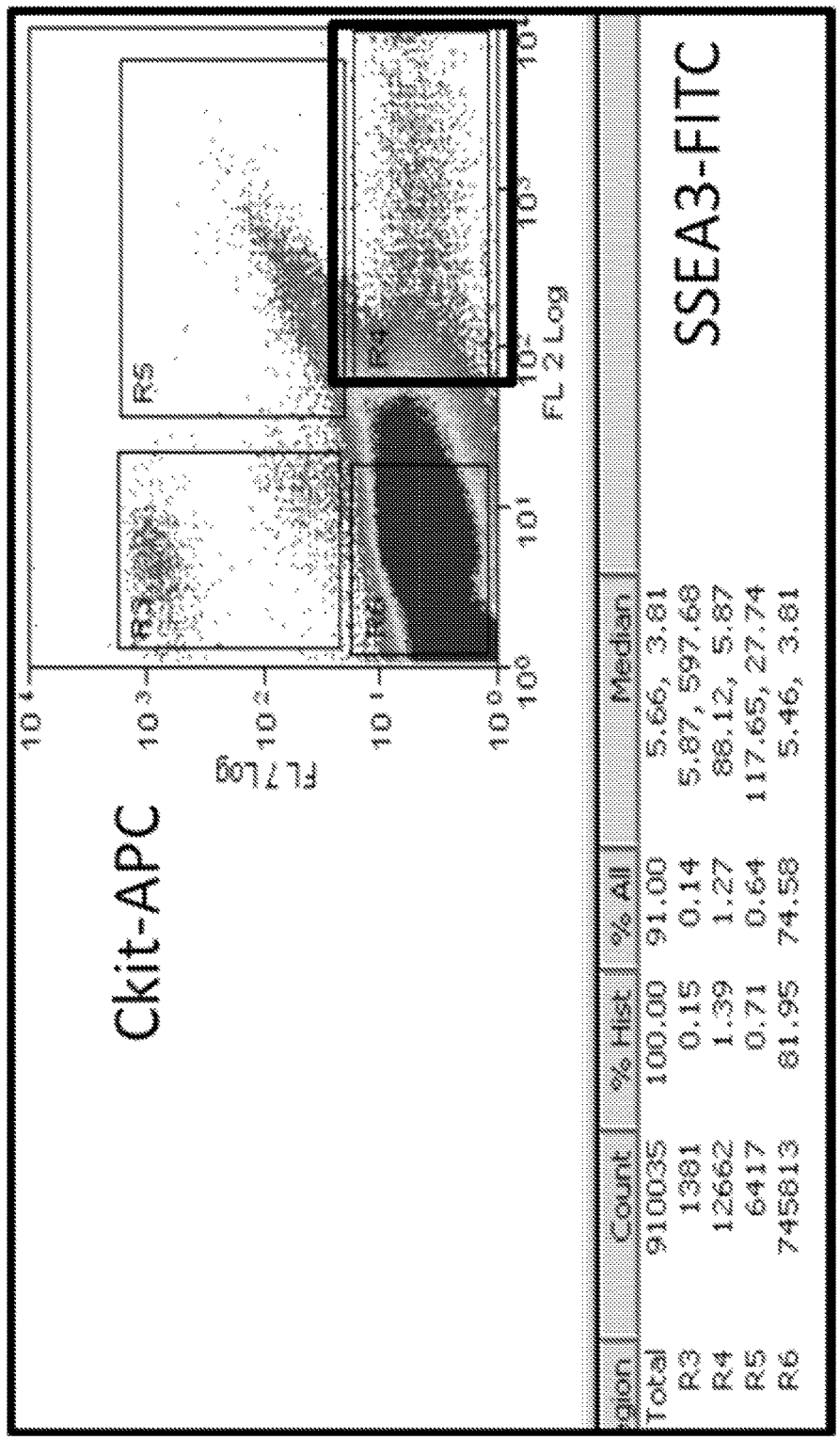

FIG. 11 is a series of flow cytometry plots using the MOFLOW® flow cytometry system (Beckman Coulter Inc.) to perform SSEA3 vs c-kit sorting. Representative MOFLOW® system FACS sorting plots of SSEA3-positive cardiac cells with the horizontal axes corresponding to SSEA3-FITC and the vertical axes corresponding to c-kit-APC. The R6 gate was sorted into sterile DPBS with subsequent centrifugation and total RNA isolation for RT-PCR analysis. Control cells for RT-PCR comparison were the same human patient's unsorted cells. RT-PCR was performed with a goal of determining fold enrichment of target gene expression in SSEA3-positive cardiac cells vs. unsorted cells.

The MOFLOW® flow cytometry system (Beckman Coulter Inc.) was also employed to perform SSEA3-positive-FITC vs c-kit-positive/CD90-positive-APC FACS sorting. The R5 gate of the MOFLOW® flow cytometry system plots corresponded to SSEA3-positive/CD90-positive/c-kit-negative cells, and the R6 gate corresponded to SSEA3-positive/CD90-negative/c-kit-cells. Cells were sorted into FACS tubes with sterile DPBS. Total RNA was isolated for RT-PCR analysis. Control cells for RT-PCR comparison were the same human patient's unsorted cells. RT-PCR was performed with a goal of determining fold enrichment of target gene expression in SSEA-positive subpopulations of SSEA3-positive/CD90-positive/c-kit-negative and SSEA3-positive/CD90-negative/c-kit-negative cells vs. unsorted cells. C-kit negativity was assessed by prior gating performed as illustrated in FIG. 11.

The MOFLOW® flow cytometry system was also employed for SSEA3-positive-FITC vs c-kit/SSEA1-positive-APC FACS sorting. The R5 gate of the MOFLOW® flow cytometry system plots corresponded to SSEA3-positive/SSEA1-positive/c-kit-negative cells and the R6 gate corresponded to SSEA3-positive/SSEA1-negative/c-kit-negative cells sorted into FACS tubes with sterile DPBS. Total RNA was isolated for RT-PCR analysis. Control cells for RT-PCR comparison were the same human patient's unsorted cells. RT-PCR was performed with a goal of determining fold enrichment of target gene expression in SSEA3-positive cardiac cell subpopulations of SSEA3-positive/SSEA1-positive/c-kit-negative and SSEA3-positive/SSEA1-negative/c-kit-negative cells vs. unsorted cells. C-kit negativity was assessed by prior gating performed as illustrated in FIG. 11.

The data developed using the MOFLOW® flow cytometry system demonstrated that SSEA1 positivity did not matter, since SSEA3-positivity provided for enrichment of cells expressing high levels of progenitor/stem markers.

Example 5

RT-PCR Analysis of EA-CPCs

RT-PCR analyses were also performed on SSEA3-positive/c-kit-negative (i.e., EA-CPC) sorted cells using the basic protocol described herein above. The results are presented in FIGS. 12-14.

Figure 12:
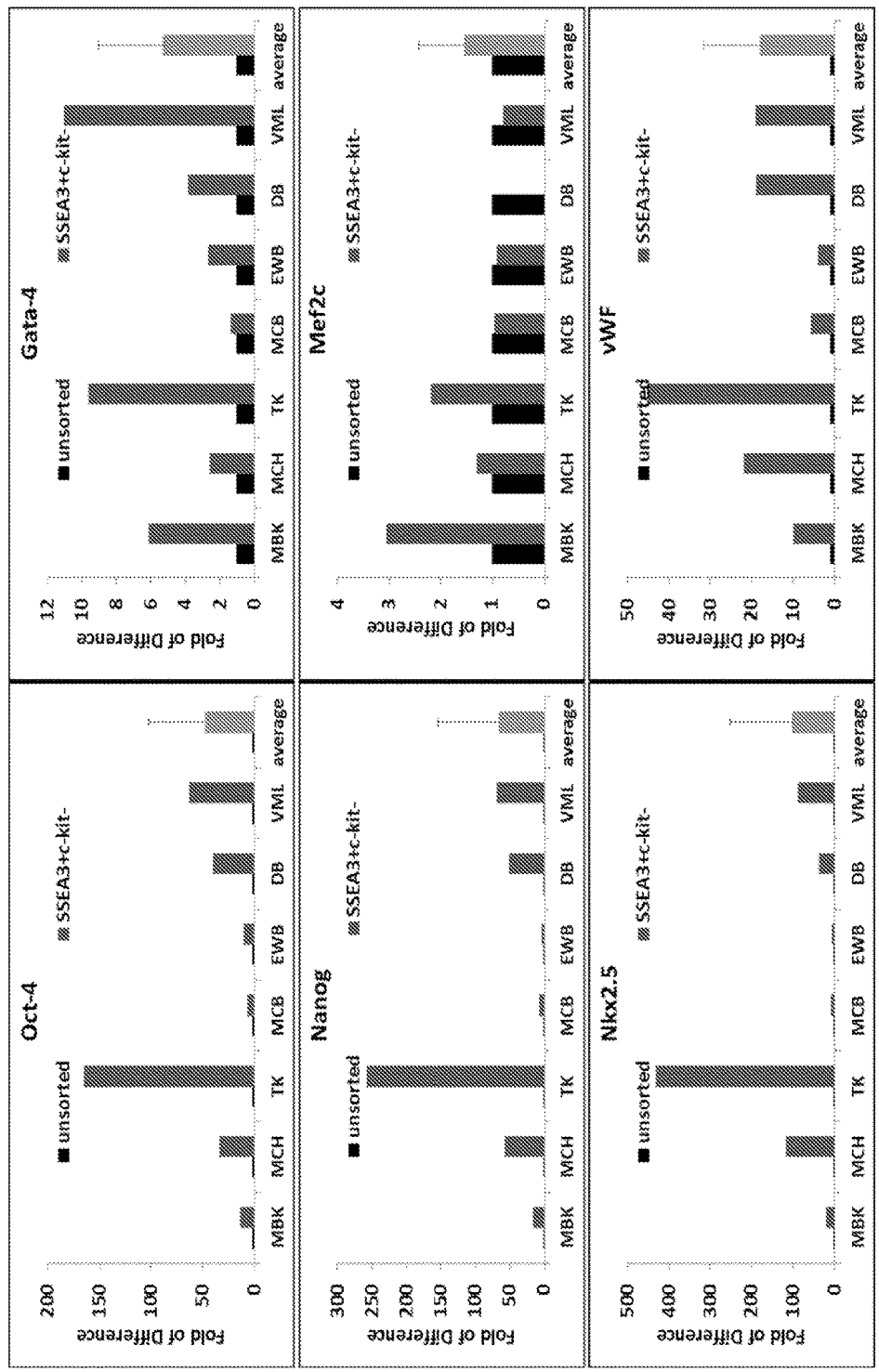

FIG. 12 shows the results of RT-PCR gene expression analyses of SSEA3-positive/c-kit-negative sorted cells from seven human patients compared to the same human patient's unsorted cells used as a control. The bars in each panel represent fold increased expression over the same human patient's unsorted cells. Enrichment of cells expressing the pluripotency-associated factors OCT4/NANOG was observed with SSEA3-positive/c-kit-negative sorting. OCT4 and NANOG showed average increased enrichment over that of unsorted cardiac cells of 46.9 and 65.5 fold respectively. Additionally, increased levels of the early cardiac markers NKX2.5 (average 99.8-fold enrichment) and GATA4 (average 5.4-fold enrichment) were observed, indicating heterogeneity in the population of SSEA3-positive/c-kit-negative cells, with some cells maintaining pluripotency-associated factor expression and others expressing a more committed progenitor phenotype with NKX2.5 and GATA4 expression. Again, the enrichment levels of NKX2.5>GATA4>MEF2C suggested that these markers represented very early cardiac progenitor cells.

Figure 13:
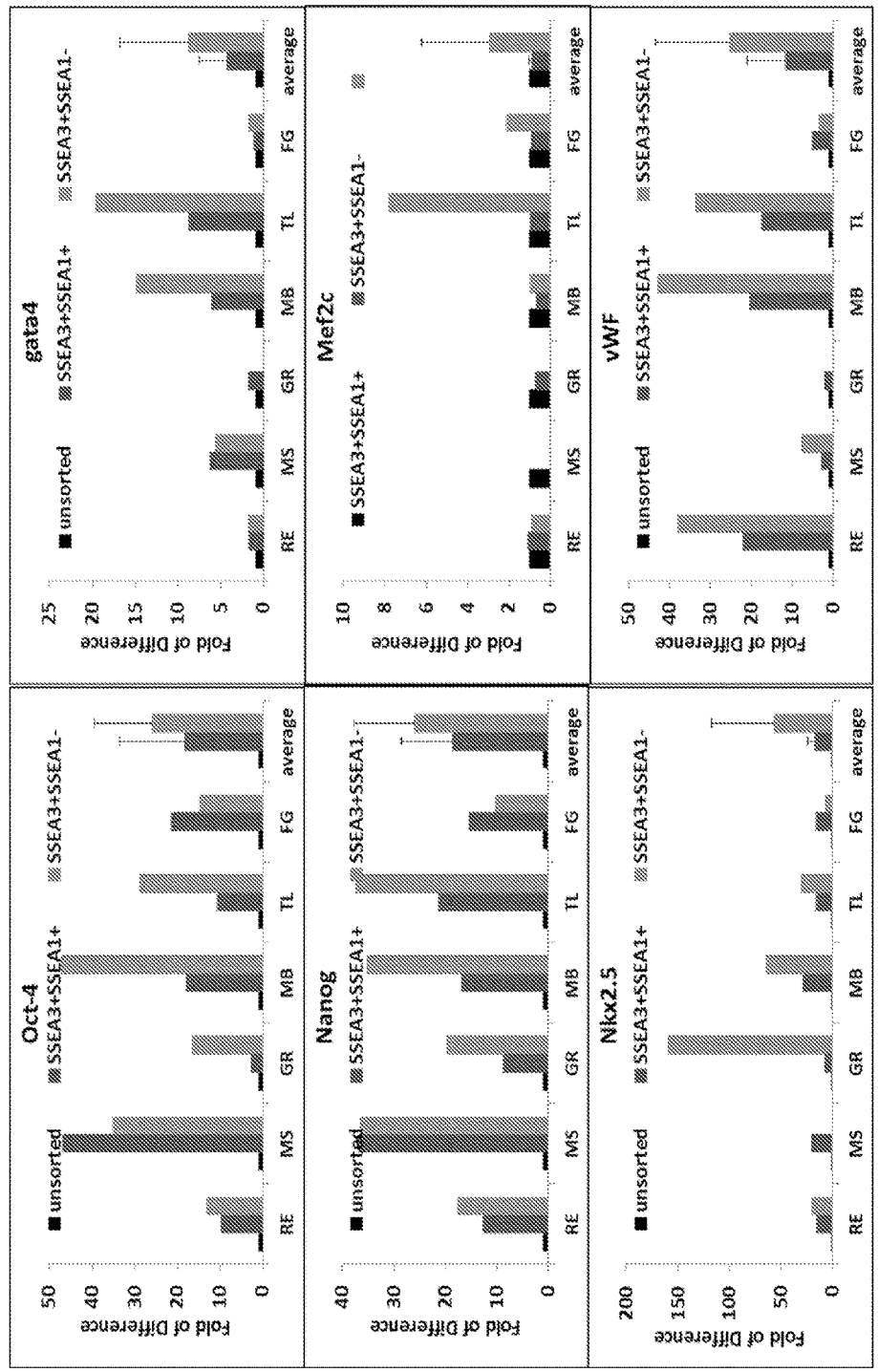

FIG. 13 is a series of bar graphs presenting the results of RT-PCR gene expression analyses of SSEA3-positive/c-kit-negative/SSEA1-negative sorted cells from initial expanded human myocardial cells. Samples isolated from six human patients were employed for the instant RT-PCR analysis. Bars in each panel represent fold increased expression over unsorted human cardiac cells from the same patient. These results did not show a statistically significant difference ($p>0.05$) between SSEA3-positive/c-kit-negative/SSEA1-negative and SSEA3-positive/c-kit-negative/SSEA1-positive populations with respect to OCT4 or NANOG expression. There was a trend for higher expression of these pluripotency-associated markers in the SSEA3-positive/c-kit-negative/SSEA1-negative cells. However, each population was observed to still average 20-fold higher expression over unsorted controls. NKX2.5 and GATA4 expression profiles followed a similar pattern. Importantly, these experiments indicated that SSEA3-positive sorting, independent of SSEA1 positivity, resulted in selection of cardiac cells with a more primitive phenotype and higher expression of OCT4, NANOG, NKX2.5, GATA4, and vWF. As a result, SSEA positivity was sufficient for immunoselection of EA-CPCs.

FIG. 14 is a series of bar graphs presenting the results of RT-PCR gene expression analyses of SSEA3-positive/c-kit-negative/CD90-positive and SSEA3-positive/c-kit-negative/CD90-negative subpopulations. Bars in each panel represent increased fold expression over unsorted cardiac cells from the same patient. Differential sorting for both the CD90-positive and CD90-negative subpopulations showed enrichment for OCT4 and NANOG. Significant differences with $p<0.05$ were seen with respect to OCT4 and NKX2.5 between SSEA3-positive/c-kit-negative/CD90-positive and SSEA3-positive/c-kit-negative/CD90-negative phenotypes. Both phenotypes showed significant enrichment for all factors relative to unsorted controls ($p<0.05$). Here as well, SSEA3-positive sorting resulted in enrichment of cells with a progenitor phenotype independent of CD90 expression.

Summarily, for each marker set, it did not matter whether the cells were positive for CD90 or SSEA1. SSEA3 positivity independently conferred enrichment for all the stem/progenitor markers (OCT4, NANOG, etc.) as both CD90-positive or -negative and SSEA1-positive or -negative SSEA3-positive cells showed higher levels of OCT4/NANOG/etc. than did unsorted cells. With only 5 patients analyzed, there was no significant difference between SSEA3-positive/SSEA3-positive or -negative cells or SSEA3-positive/CD90-positive or -negative cells. As such, there was no advantage gained by double sorting for SSEA3 positivity and either CD90 positivity/negativity or SSEA1 positivity/negativity cells.

Example 6

Magnetic Immunoselection of an SSEA3-Positive Subpopulation of Cardiac Progenitor Cells SSEA3-positive cells were also separated by magnetic immunoselection. The results are presented in FIGS. 15 and 16.

Figure 17:
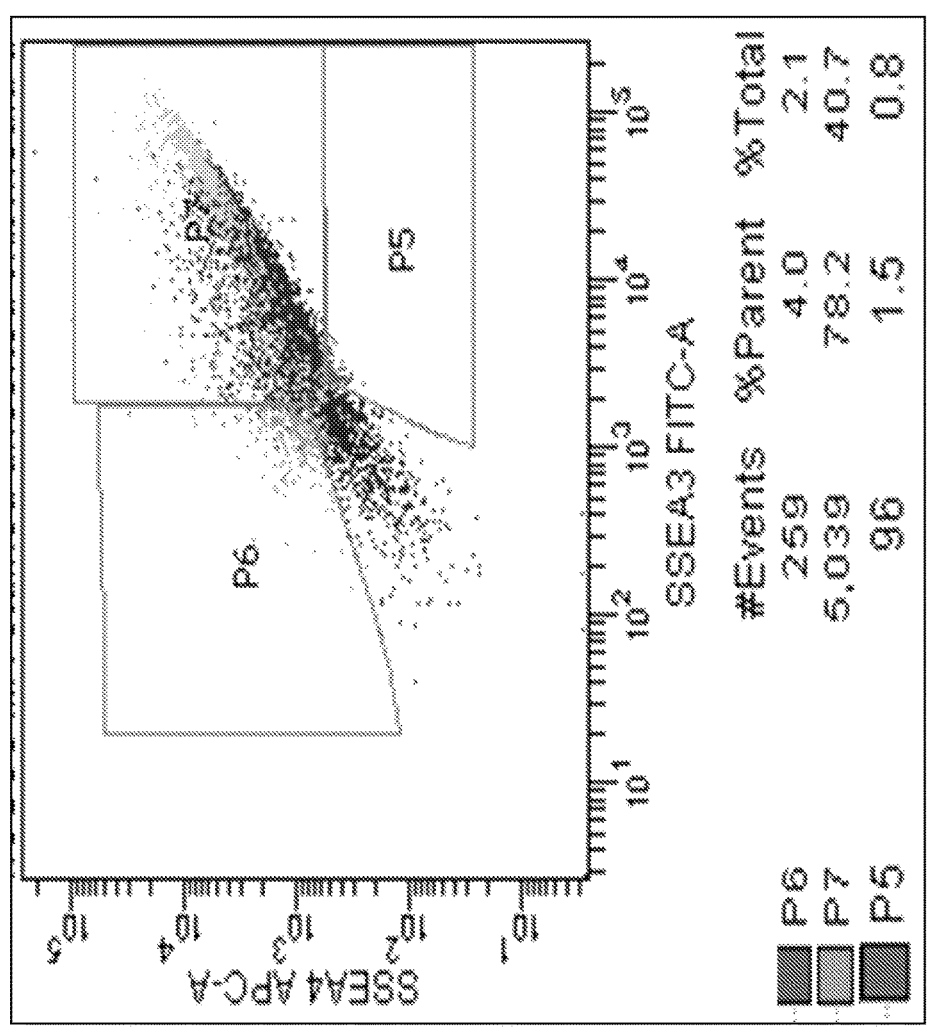
FIG. 17 is a flow cytometric analysis of cells positively selected by MACS for SSEA3 positively evaluated for co-expression of SSEA4.

FIG. 15A depicts an exemplary apparatus for magnet immunoselection utilizing the Miltenyi OCTOMACS™ brand sorting apparatus (Miltenyi Biotec) with MS magnetic sorting columns, pre-separation filters, and the magnetic stand. Cells were trypsinized and washed twice with sterile MACS staining buffer containing 1% bovine serum albumin (BSA), otherwise prepared according to manufacturer's instructions. Cells were then labeled with a rat monoclonal IgM anti-human SSEA3 antibody labeled with PE (1:20 dilution; eBioscience, Inc.) for 20 minutes on ice in the dark in a volume of 300 µL. Cells were washed once to remove unbound antibody and subsequently labeled with a magnetic bead-coupled secondary antibody (Miltenyi Biotec mouse monoclonal IgG anti-PE; 1:5 dilution). Secondary labeling was 15 minutes on ice in the dark in a staining volume of 200 µL. Cells were again washed once to remove unbound antibody. Cells were then resuspended in Miltenyi MACS sorting buffer with 1% BSA and added to the magnetic MS column fixed to the magnetic stand as depicted in FIG. 15A. Positive cells were captured in the column and negative cells flowed through to 15 mL tubes as depicted. Columns were washed 3 times with sterile MACS buffer according to manufacturer's instructions to further elute negative cells. The positively selected cells bound within the magnetic columns were flushed into an alternate 15 mL tube. SSEA3-negative cells in the washes were discarded and SSEA3-positive cells were utilized immediately for assays or replated for additional expansion in vitro. Exemplary SSEA3-positive cells immediately post-selection are depicted in FIG. 11 and in FIG. 17B. Validation of SSEA3 positivity by flow cytometric analysis and immunocytochemistry is shown in FIGS. 15C and 15D, respectively.

Figure 15B:
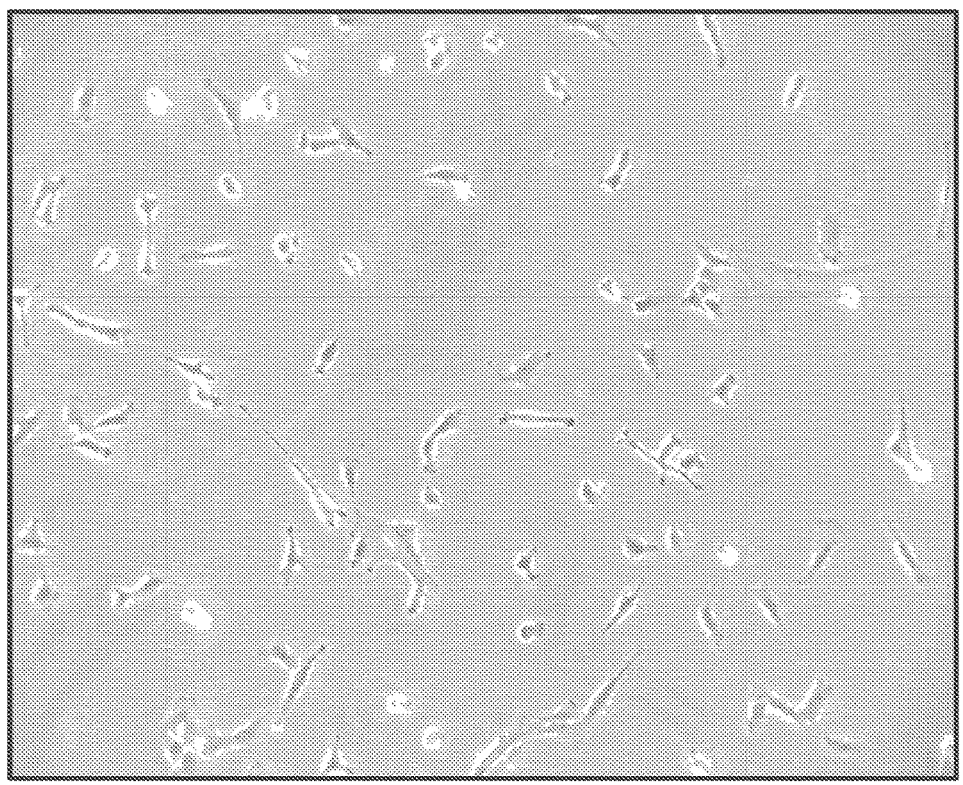

FIG. 15B is a photomicrograph depicting positively selected SSEA3-positive cells 24 hours after MACS enrichment. SSEA3 immunoselection was performed at the end of passage 1 (P1). Accordingly, the cells shown were the founding population of passage 2 (P2). 40% conditioned media from P1 combined with 60% new media was used for expansion of SSEA3-positive P2 cells. SSEA3-positive cells were observed to be small and had a high nucleus to cytoplasm ratio.

Figure 15C:
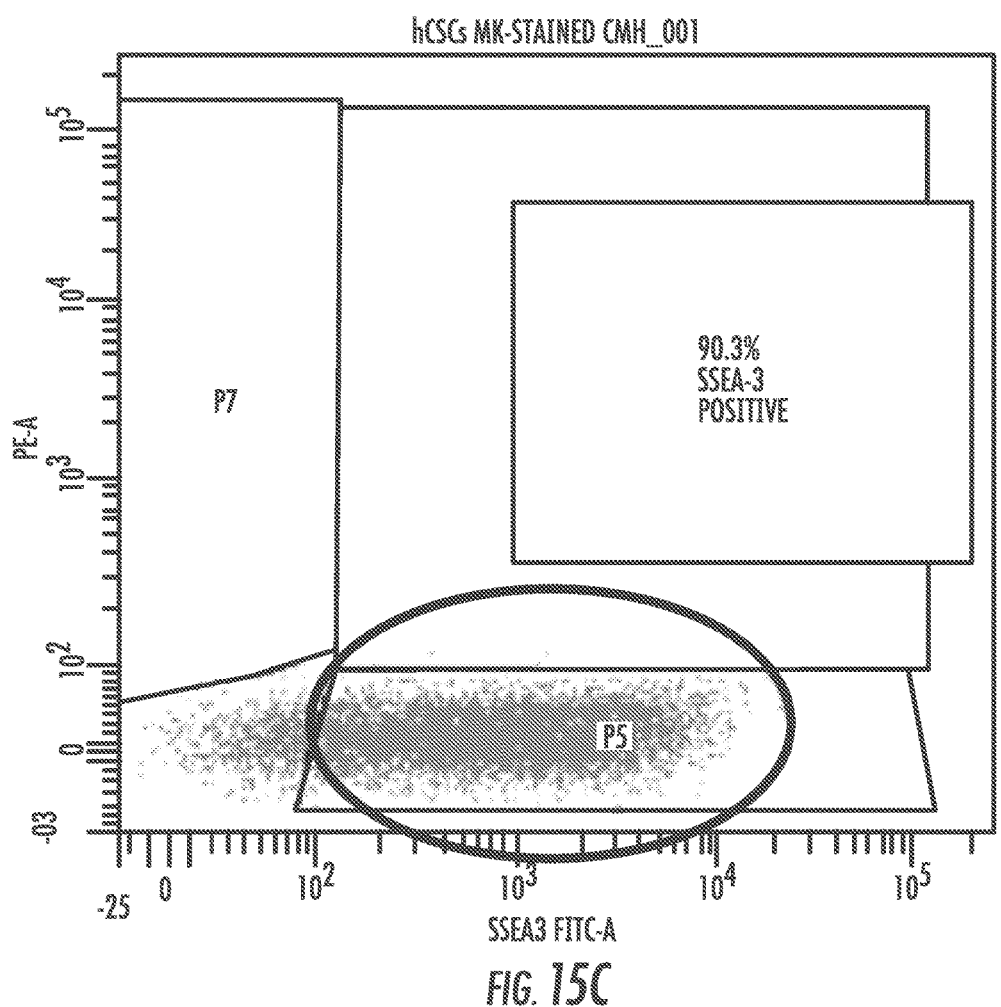

FIG. 15C presents the results of flow cytometric analysis performed following SSEA3 immunomagnetic selection in order to quantify and validate enrichment. SSEA3-positive enrichment was validated and observed to be >90% (shown in the P5 gate; circled) as compared to isotype control (not shown).

Figure 15D:
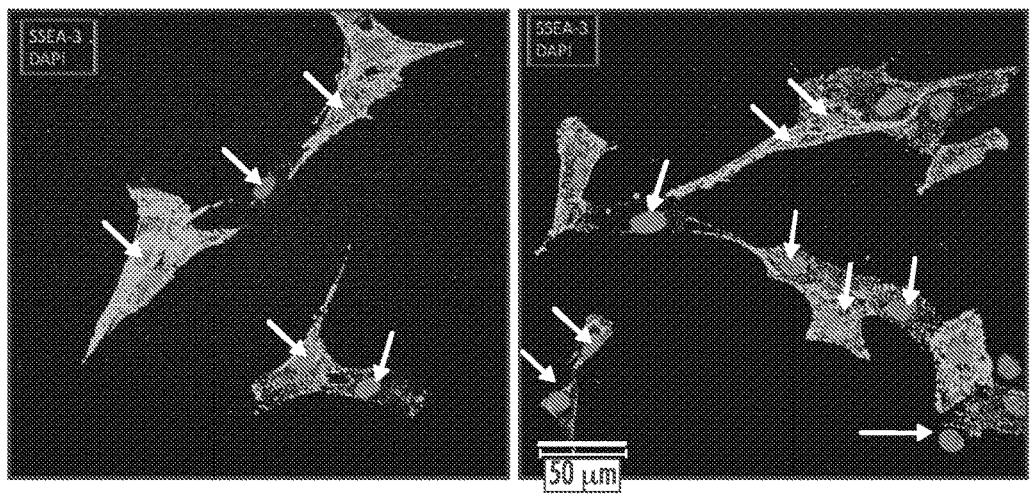

FIG. 15D presents the results of evaluations of the MACS-enriched SSEA3-positive cells shown in FIG. 15C for SSEA3 expression by immunocytochemistry. Cells were labeled with a rat monoclonal IgM anti-SSEA3 antibody and an anti-rat IgM secondary antibody labeled with FITC (eBioscience, Inc.). SSEA3 positivity is shown in green (gray in the B&W) with DAPI nuclear staining shown in blue (arrows). Two separate fields are shown. The white scale bar in the bottom left corner of the right image is 50 EA-CPCs were observed to be small with high nuclear to cytoplasm ratio. FIG. 15D also shows that some cells were negative, some were dimmer, and some were brightly positive for SSEA3, similar to that seen in the flow analyses.

Figure 16:
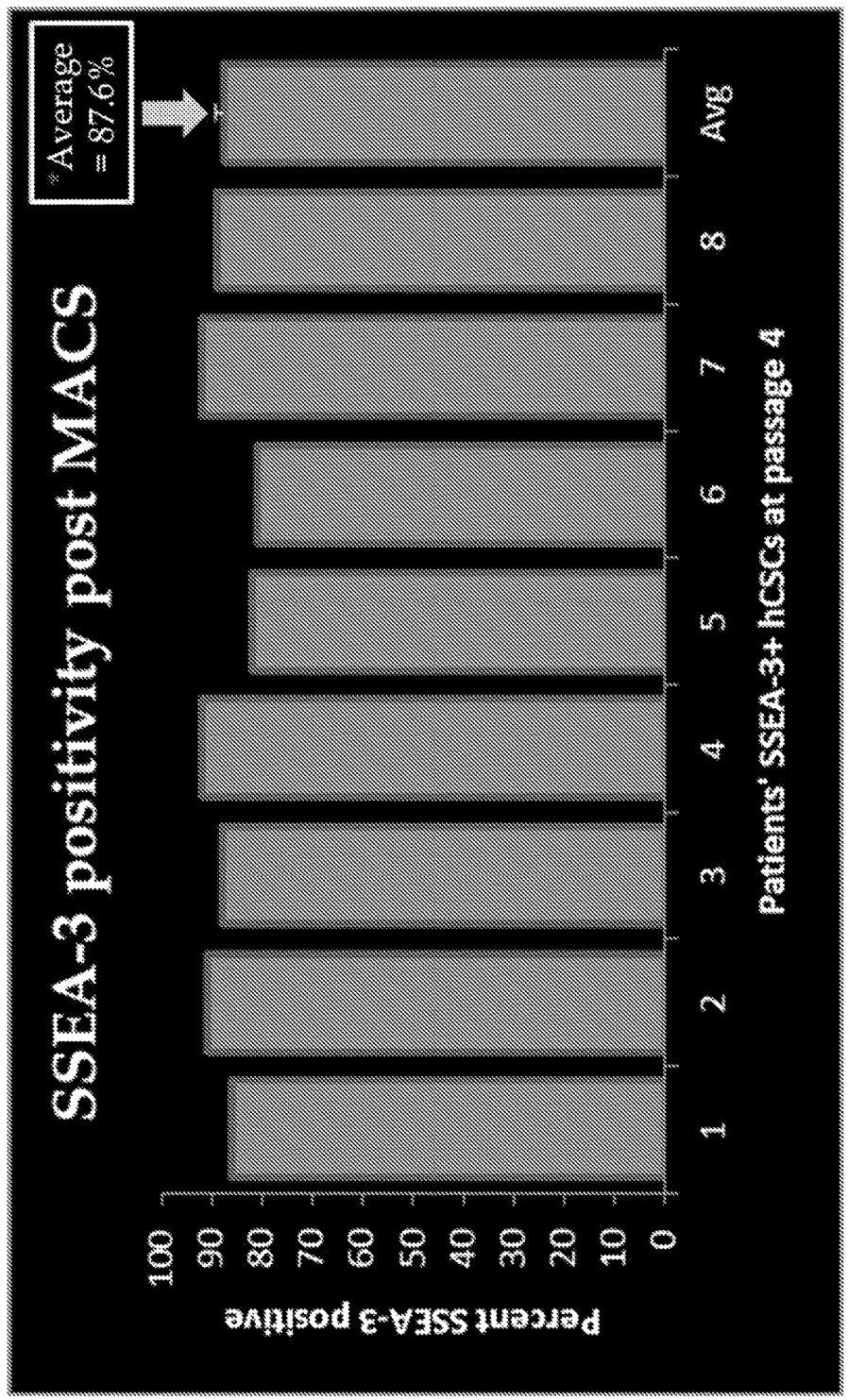
FIG. 16 is a bar graph showing the percentage of SSEA3-positive cells present in right atrial specimens obtained from eight (8) separate patients undergoing open heart surgery. Isolates were processed, cells were expanded in vitro, and MACS-enriched for SSEA3-positive cells.

FIG. 16 is a bar graph showing the percentage of SSEA3-positive cells present in various right atrial specimens obtained from eight (8) separate patients undergoing open heart surgery. Isolates were processed, cells were expanded in vitro, and MACS-enriched for SSEA3-positive cells. Enrichment efficiency and reproducibility were evaluated with flow cytometric analysis of the positive selections from MACS sorting for each patient. SSEA3-positivity after MACS sorting as described herein averaged 87.6±2.0%.

FIG. 16 demonstrates the reproducibility of the presently disclosed methods and the efficiency at which the methods could be applied to cells isolated from different subjects. P4 was reached one passage after sorting. Therefore, the presently disclosed methods enrich unsorted populations from SSEA3-positive cells of maybe 10-30% to over 80% and concurrently enrich for cells expressing higher OCT4/NANOG/NKX2.5/etc. (see the RT-PCR data shown in FIGS. 19 and 20 below).

Example 7

Flow Cytometric Analysis of SSEA3-Positive CPCs for SSEA4 Coexpression

Cells positively selected by MACS for SSEA3 positively were also evaluated for co-expression of SSEA4. The results are presented in FIG. 17.

Cells were labeled with a rat monoclonal IgM anti-SSEA3 primary antibody and then with an anti-rat IgM secondary antibody labeled with FITC (eBioscience, Inc.) and also with a mouse monoclonal IgG anti-SSEA4 with primary antibody and an anti-mouse IgG secondary antibody labeled with APC (eBioscience, Inc.). All SSEA3-expressing cells were found to co-express SSEA4 in the P7 gate (78%). There were no SSEA3-positive/SSEA4-negative cells above isotype control in the P5 gate. There were, however, SSEA4-positive/SSEA3-negative cell shown in the P6 gate (4.0%). This was expected as SSEA3 is more primitive and was lost before SSEA4 with in vitro expansion and spontaneous loss of progenitor phenotype as disclosed herein.

Co-positive staining for SSEA4 thus validated the SSEA3-positive staining disclosed herein as SSEA4 was virtually always co-expressed with SSEA3. The opposite is not always true, however, as SSEA3 disappeared first with differentiation. Therefore, in the context of the presently disclosed methods, SSEA3 expression was integrally more important than SSEA4 expression, and SSEA4 expression was only a marker confirming true SSEA3 expression. Thus, and as disclosed herein, the MACS sorting methods for selection of EA-CPCs is entirely based on expression of SSEA3.

Example 8

RT-PCR Analysis of an SSEA3-Positive Subpopulation of Cardiac Progenitor Cells The SSEA3-positive EA-CPCs were also subjected to a series of RT-PCR analyses, the result of which are presented in FIGS. 18-20.

FIG. 18 is a photograph of the results of RT-PCR analysis of SSEA3-positive P3 cells sorted by MACS with respect to the pluripotency-associated markers OCT4 and NANOG, the early cardiac lineage markers NKX2.5, GATA4, GATA6, VEGFR2 (KDR), and telomerase (TERT). SSEA3-positive cardiac cells showed positive expression for each of these markers indicating heterogeneity of SSEA3-positive cells in relation to stemness and cardiac lineage commitment. Expression of these markers at the mRNA level were indicative of cells with a stem cell like-associated phenotype (OCT4/NANOG/telomerase), but also with the capacity to differentiate and contribute to all three cardiac lineages: myocytes (NKX2.5/GATA4), smooth muscle (GATA6), and endothelium (KDR). Importantly, in vitro expanded SSEA3-positive cells appeared to have an organ-(cardiac) specific and cardiac-predisposed transcriptional profile related to the markers noted above. This differs from hematopoietic stem cells (HSCs), bone marrow-derived mesenchymal stem cells (BM-MSCs), or any other stem cell population that are not isolated specifically from human cardiac tissue such as but not limited to those isolated from adipose, dental, or dermal tissues. These non-cardiac populations do not ultimately provide any direct contribution to any cardiac lineage or to overall cardiac homeostasis with their native in vivo differentiation within their respective organs.

FIGS. 19A-19C depict RT-PCR analyses of SSEA3-positive cells purified by MACS sorting as outlined in FIG. 15A for various markers. FIG. 19A shows the results of RT-PCR analysis of SSEA3-positive EA-CPCs isolated from nine (9) human right atrial tissue samples. EA-CPCs were compared by RT-PCR for relative expression levels of the pluripotency-associated markers OCT4 and NANOG, the early cardiac mesodermal markers BRACHYURY, MESP1, MIXL1, NKX2.5, GATA4, TBX5, TBX18, and TBX20, the smooth muscle marker GATA6, the endothelial marker KDR, and telomerase (TERT). Expression levels of these markers were compared by RT-PCR to the expression of those same markers in the same patient's unsorted cells and the SSEA3-negatively selected subpopulations resulting from the MACS sorting procedure.

This methodology allowed real differences in mRNA expression to be seen within the same patient's cells with respect to SSEA3-positive sorting, and provided important evidence of the validity and superiority in SSEA3-positive immunoselection with respect to selection of cells expressing higher levels of markers known to be expressed in stem and progenitor cell populations. Mean fold enrichments of marker mRNA levels in SSEA3-positive EA-CPCs (S3+; right most bar of each triad of bars per marker) over those in SSEA3-negative (S3−; left most bar of each triad of bars per marker) cells are presented in the graph. Also shown are average fold enrichments for each marker for unsorted RAA cells (middle bar of each triad of bars per marker). Statistically significant enrichment and higher levels of expression were seen in SSEA3-positive cells with respect to MESP1, BRACHYURY, NANOG, MIXL1, NKX2.5, TERT, OCT4, and KDR.

Although not presented in FIG. 19A, the expression levels for vWF showed similar enrichment in SSEA3-positive cells versus SSEA3-negative and unsorted cells from the same patients. Higher expression of vWF at the protein level was confirmed by western blot, and expression of several other selected markers were determined to be higher at the mRNA level, to validate real enrichment of these markers at the protein level (see FIG. 19B below). The observed mRNA enrichment pattern was consistent with SSEA3-positive EA-CPCs possessing a more primitive cardiac phenotype than SSEA3-negative cells, the latter of which included SSEA4-positive/SSEA3-negative cells. As set forth herein, although SSEA3-positive cells co-expressed SSEA4, SSEA4 positivity did not confer the same advantage of higher stem/progenitor marker expression as SSEA3 positivity. As shown herein above in FIG. 10, there were SSEA4-positive/SSEA3-negative cells present within the SSEA3-negative population in the RT-PCR analysis above. It was clearly demonstrated that SSEA3 positivity alone was associated with this selection advantage, and for isolation of cells expressing higher levels of the aforementioned markers.

FIG. 19B depicts a series of western blot analyses of unsorted cardiac cells, MACS-sorted SSEA3-positive cells (SSEA+), and MACS-sorted SSEA3-negative (SSEA−) cells from three (3) individual patients for the listed markers to validate protein expression differences corresponding to the RT-PCR analyses shown in FIG. 19A. The western blots show higher expression of the markers vWF, WT-1, KDR, NKX2.5, and BRACHYURY in SSEA3-positive EA-CPCs, reflective of the higher levels of mRNA expression of these same cells identified by RT-PCR, thereby validating the expression differences observed in the mRNA.

FIG. 19C is an immunocytochemistry image of SSEA3-positive cells labeled with a rat anti-SSEA3 primary antibody (eBioscience, Inc.). The cells were fixed and permeabilized with methanol by a standard methodology. Cell were then labeled with a rabbit anti-human NANOG antibody (ABCAM®) that was detected with a mouse anti-rabbit IgG secondary antibody labeled with TRITC (red or gray stippling in nuclei, the latter indicated by dotted white lines) and also a rat anti-human SSEA-3 antibody that was detected with a mouse anti-rat IgM secondary antibody labeled with FITC (solid white lines in left panel). Additionally, SSEA3-positive MACS sorted EA-CPCs were fixed and permeabilized with methanol and labeled with a goat anti-human NKX2.5 primary antibody detected with a fluorochrome-conjugated mouse anti-goat IgG secondary antibody labeled with FITC (nuclei of NKX2.5-positive cells indicated with solid circles in the right panel). Nuclei were labeled in both panels with DAPI staining (indicated with dotted arrows in the left panel and broken circles in the right panel).

It is noted that WT-1 is a marker of early progenitors fetal cardiac development, and its expression in the EA-CPCs supported the primitive phenotype of SSEA3-positive cells. SSEA3-positive EA-CPCs displayed not only a stem/progenitor phenotype with respect to OCT4/NANOG/TERT expression but also, importantly, a cardiac-specific profile. This pattern is not observed in adult stem cells populations that are not isolated from the human heart and that normally do not contribute to cardiac homeostasis or repair by directly or indirectly contributing to mature cardiac lineages in vivo.

Similarly, vWF is expressed in some early endothelial lineages. This in combination with NKX2.5, vWF, GATA6, MEF2C, TBX5, NANOG, and OCT4 being present at both the protein and mRNA levels supports the notion that SSEA3-positive cells were heterogenous, with a continuum of stem/progenitors that are more immature (NANOG and OCT4) as well as contain more committed progenitors to all three cardiac lineages (myocyte: NKX2.5; smooth muscle: GATA6; endothelial cells: vWF) and had the capacity to be multipotent. This was further supported directly by western blot data in differentiation conditions as disclosed herein.

SSEA3-positive cells, as seen by RT-PCR and Western blot analyses, showed expression of NANOG and NKX2.5 by immunocytochemistry, located appropriately within the nucleus. As expected, heterogeneity was observed in terms of NKX2.5 and NANOG expression and was consistent with a continuum of progenitor states, with some SSEA3-positive EA-CPCs showing expression of the pluripotency-associated marker NANOG and others showing a more committed cardiac lineage phenotype as demonstrated by NKX2.5 expression. The above referenced RT-PCR data was also validated with positive protein expression of these markers.

FIGS. 20A and 20B depict the results of further analyses of SSEA3-positive cells isolated by MACS sorting as described in FIG. 15A. FIG. 20A is a bar graph showing percent SSEA3 positivity of cells isolated from right atrial tissue samples from eight (8) patients at passage 9 (P9). Cells were analyzed at passage 3 (P3) for SSEA3 positivity (average 87.6% positivity) and expanded in vitro to P9 allowing exponential expansion. The cells were reanalyzed for SSEA3 positivity by FACS as disclosed herein. SSEA3 positivity fell from an average of 87.6% at P3 to an average of 47.2% at P9, which indicated that SSEA3 expression was lost from EA-CPCs over time in culture and was a reflection of a loss of stem/progenitor phenotype (similar to the pattern observed in human ES cells).

Therefore, cells retaining SSEA3-positive expression over time in culture might retain a more primitive stem/progenitor phenotype. To evaluate this, MACS sorting was again performed on each SSEA3-positive cell line to re-enrich the SSEA3-positive population. The results are represented in FIG. 20B, which is a series of bar graphs showing a comparison of eight (8) patients' SSEA3 positively immunoselected cells (red bars; right bar of each pair) compared to the SSEA3-negative cells (blue bars; left bar of each pair) after 9 passages by RT-PCR. In similar fashion to the analysis performed and shown in FIG. 19A, the P9 SSEA3-positively selected EA-CPCs were compared by RT-PCR to the P9 SSEA3-negatively selected cells that flowed through the magnetic column during MACS selection. The markers selected for real time PCR comparison were the pluripotency-associated markers OCT4 and NANOG and the early cardiac progenitor lineage markers NKX2.5, GATA4, GATA6, and vWF.

Thus, and as with the profiles shown in FIG. 19A at early passage number, SSEA3 positivity at late passage number was also correlated with a higher expression of the pluripotency-associated factors OCT4 and NANOG as well as the cardiac progenitor markers NKX2.5 and vWF as compared to that of SSEA3-negative cells from the same patient. This also illustrated the reproducibility of the instantly disclosed methods of isolation and further confirmed the rational for SSEA3-positive immunoselection disclosed herein. Cumulatively, the evidence presented herein validated the ability to obtain cells with a more primitive cardiac phenotype by the instantly disclosed methods comprising specific SSEA3 immunoselection and in vitro expansion.

With respect to FIGS. 19 and 20, RT-PCR analyses of P3 EA-CPCs demonstrated increased mRNA expression of MESP1, BRACHYURY, NANOG, MIXL1, NKX2.5, TERT, OCT4, and KDR (vWF was also increased). The increased expressions of BRACHYURY, NKX2.5, KDR, WT-1, vWF, and TERT were validated by western blot analysis, which was indicative of true enrichment of cells expressing higher levels of these progenitor-associated markers.

Quantitative PCR (qPCR) analyses of MACS-sorted P9 EA-CPCs demonstrated that significant increases in expression of NANOG, NKX2.5, OCT4, and vWF were noted in the P9 EA-CPCs as compared to SSEA3-negative cells, while expression of GATA4 and GATA6 was not significantly increased.

Accordingly, MACS resorting at late passage for cells that retained an SSEA3-positive phenotype was found to remain directly correlative with cells expressing higher levels of pluripotency and progenitor-associated phenotypic markers. This methodology and evidence supported the rationale behind the use of SSEA3 positivity as a marker to immunoselect cardiac progenitor cells. No other cell type isolated from the human heart has been characterized in this way or as stringently to date.

Example 9

In Vitro Differentiation of an SSEA3-Positive Subpopulation of Cardiac Progenitor Cells SSEA3-positive MACS-sorted EA-CPCs from 3 patients at passages 3-5 were seeded at 90% confluence into 6 well plates as described in the protocol outlined in FIG. 21A. Normal culture media was changed to differentiation media which consisted of DMEM, 5% FBS, $10^{-8}$ M dexamethasone, 0.05% 20 mM ascorbic acid, 0.75% DMSO, 0.2 mM L-glutathione, 0.01% insulin/selenium/transferrin (ITS), and 100 U/ml penicillin/streptomycin. Total RNA and protein were isolated at baseline prior to starting differentiation conditions and again 7-21 days after initiation of differentiation. Western blot analysis (see FIG. 21B; left panel, illustrating blots performed at day 0 and at day 14) showed evidence of cardiomyocyte differentiation by upregulation of alpha sarcomeric actin ($\alpha$-SA) and alpha myosin heavy chain ($\alpha$-MHC) over 14 days. Evidence of smooth muscle differentiation was also seen with upregulation of smooth muscle actin (SMA) and smooth muscle myosin heavy chain (SM-MHC) over 14 days. Connexin 43 (CX43) was expressed at baseline and throughout differentiation conditions.

Quantitative changes of respective markers from baseline levels are presented below in the right panel of FIG. 21B. Troponin T (TNNT2) was also seen to be increased in differentiation conditions as measured by RT-PCR. Increases in mRNA for troponin T were seen as early as day 7 after initiation of differentiation conditions varying thereafter at the subsequent time points. Time points in the TNNT2 RT-PCR analysis from left to right are day 0 (prior to differentiation), and days 3, 7, 10, and 17, respectively. Although fluctuations in mRNA levels at these time points were observed, levels of TNNT2 mRNA were consistently increased over that of the baseline day zero. These data implied that SSEA3-positive EA-CPCs were multipotent and able to give rise not only to endothelial lineages (evidenced by prior heterogenous expression of vWF and KDR), but also could differentiate into mature cardiac lineages including myocytes ($\alpha$-MHC/$\alpha$-SA/TNNT2) and smooth muscle cells (SMA/SM-MHC)

Protein expression analyses by western blot are shown in FIG. 21C quantified in fold-change from baseline day 0 levels. Shown is the mean±SEM value for respective markers of differentiation in fold-change from baseline. Significant increases (p<0.05) were observed for SM-MHC, SMA, α-MHC, and α-SA. Protein expression of Connexin 43 was not significantly different (p>0.05) from baseline.

FIG. 21D depicts an exemplary confocal microscopy image of human SSEA3-positive EA-CPCs after differentiation expressing the cardiomyocyte and smooth muscle gap junctional protein Connexin 43 (red stippling; examples indicated by white arrows) at the sites of cell to cell contact and at the site of intracellular synthesis within the perinuclear located rough endoplasmic reticulum. Alpha tubulin is shown in green (gray or white in B&W) and nuclei are labeled with DAPI staining in blue (examples indicated with dotted arrows). Connexin 43 expression was consistent with the ability of SSEA3-positive cardiac cells to electrochemically couple with surrounding cells and functionally integrate into human myocardium.

NANOG expression was also examined by RT-PCR during the time course of SSEA3-positive EA-CPC differentiation of the three (3) patients outlined above. As shown in FIG. 21E, NANOG expression decreased over time as the cells displayed lineage commitment toward more mature cardiac phenotypes, thus showing loss of the baseline progenitor phenotype that had high levels of NANOG expression. The vertical Y-axis is represented as fold-change relative to baseline (day 0) expression and the horizontal X-axis is the time points 0, 3, 7, 10, and 17 days after initiation of differentiation conditions as described in FIG. 21A.

Example 10

In Vivo Assessment of Repair of Ischemic Injury by EA-CPCs 12 week old severe combined immune deficiency (SCID) female mice were subjected to myocardial ischemia/reperfusion injury via 45 minute left anterior descending coronary artery occlusion followed by 45 minutes of normal reperfusion. Accordingly, ischemic injury occurred almost exclusively in the left ventricular wall and anterior septum. Following reperfusion, a dose of 200,000 human SSEA3-positive EA-CPCs (titrated for a retained intramyocardial dose of 100,000 cells after withdrawal of the delivery needle) was injected in the border zone of the infarcted area at 4 locations using 10 μL per injection. Identical volumes of intramyocardially injected sterile saline served as a vehicle control in a parallel treated cohort of SCID female mice. Both cohorts of mice, SSEA3-positive EA-CPC-treated and vehicle control, were subjected to functional analyses via serial echocardiography at baseline, 5 days, and 35 days after ischemia/reperfusion injury. After 35 days, the mice were sacrificed with functional assessments by standard Millar pressure-volume methodology. Ultimately, hearts underwent formalin fixation and paraffin embedding with subsequent sectioning and Trichrome staining to calculate respective myocardial scar sizes relative to the amount of myocardium at risk to ischemic injury.

FIG. 22A is a Trichrome stained cross section of myocardium isolated from control (left) and EA-CPC-treated (right) mice. There was significantly increased viable tissue relative to area of myocardium at risk with p<0.05 as shown in FIG. 22B (left panel). The area or amount of myocardium at risk was equal between groups (see FIG. 22B, right panel) indicating that increases in viable tissue solely resulted from the EA-CPC therapy. Ischemically damaged hearts that were treated with human EA-CPCs underwent less decompensatory dilatation as shown by the LV expansion index (see FIG. 22C, right panel). Additionally, there was significantly larger anterior wall thickness (see FIG. 22C, left panel). The decreases in LV diameter and increases in myocardial wall thickness observed in the treatment group can give information on myocardial wall stress according to the Law of LaPlace (see e.g. Moriarty, 1980). As wall stress is directly proportional to the LV diameter (seen to be smaller) and inversely proportional to the wall thickness (seen to be larger), human EA-CPC therapy essentially resulted in the abrogation of decompensatory LV remodeling and prevented increases in wall stress known to occur after ischemic injury.

Additional parameters related to cardiac injury and repair in EA-CPC-treated vs. untreated mice were also tested. For these investigations, echocardiography (echo) was performed for left ventricular functional assessment in an immunocompromised murine model (SCID mice) of ischemia/reperfusion (I/R) injury and subsequent human EA-CPC intramyocardial administration. Echo was performed at baseline prior to injury as well as 5 days and 35 days post I/R with subsequent cell therapy. Ischemic injury consisted of 45 minutes of left anterior descending (LAD) artery occlusion with 45 minutes of normal reperfusion followed by intramyocardial injection of 200,000 human EA-CPCs or normal saline control in the border zones of the infarction area. SCID mice we followed for 35 days and assessed for functional parameters.

Significant improvements in cardiac function were seen over 35 days in the EA-CPC treatment group (EA-CPC) vs that of the control group (CTRL). First, ejection fraction (as measured in B Mode echocardiography) tests of untreated control (vehicle only; n=11) vs. EA-CPC-treated (n=15) were conducted. The results are shown in FIG. 23A. At baseline, the control group had an average ejection fraction (EF) of 62.9±1.7%, while the human EA-CPC-treated group had an average EF of 64.6±1.2% (p>0.05). Five (5) days after treatment, the control group had an average EF of 31.2±2.2%, while the human EA-CPC-treated group had an average EF of 37.5±1.9% (p>0.05). At 35 days post-treatment, the control group had an average EF of 29.8±2.8%, while the human EA-CPC-treated group had an average EF of 44.4±2.8%. At 35 days, the difference between the control group and the EA-CPC-treated group was statistically significant (p<0.05) with nearly 15% absolute ejection fraction unit (EFUs) improvement compared to controls.

Similarly, ejection fractions assessed by Simpson's method echocardiography showed a similar pattern of improvement in the EA-CPC treatment group (see FIG. 23B). The control group (vehicle only; n=11) had an average EF of 67.69±1.7%, while the human EA-CPC-treated group (n=15) had an average EF of 66.5±1.5% (p>0.05). Five (5) days after treatment, the control group had an average EF of 37.7±1.3%, while the human EA-CPC-treated group had an average EF of 40.4±0.7% (p>0.05). At 35 days post-treatment, the control group had an average EF of 31.3±1.8%, while the human EA-CPC-treated group had an average EF of 44.8±2.5%. At 35 days, the difference between the control group and the EA-CPC-treated group was statistically significant (p<0.05), essentially an improvement in absolute EF units of 13% over controls. Thus, there were no significant differences between groups at baseline or at 5 days by either measurement methodology indicating no difference in starting populations/cohorts of SCID mice and no difference in the extent of induced myocardial injury. Improvements observed at 35 days were apparently solely due to the treatment with EA-CPCs.

Left ventricular end diastolic and end systolic volumes was also assessed by Simpson's method echocardiography comparing EA-CPC treatment (n=15) and vehicle control (n=11) groups at baseline (prior to I/R injury), 5 days, and 35 days after I/R injury. At baseline, Simpson end diastolic volumes were 51.0±3.8 µL for the untreated control and 54.2±2.2 µL for the EA-CPC-treated group (p>0.05). At five (5) days post-I/R injury, Simpson end diastolic volumes were 57.0±3.9 µL for the untreated control and 52.2±4.2 µL for the EA-CPC-treated group (p>0.05). At 35 days, the average left ventricular end diastolic volume was significantly smaller in the EA-CPC treatment group (67.0±4.7 µL) vs. that of the control (79.9±5.3 µL) at 35 days, indicating less adverse LV remodeling and less decompensatory LV dilatation occurred in the EA-CPC treatment group.

Similarly, Simpson end systolic volumes were determined at baseline, at five (5) days post-I/R injury, and at 35 days post-I/R injury. At baseline, Simpson end systolic volumes were 16.8±1.7 µL for the untreated control and 18.3±1.3 µL for the EA-CPC-treated group (p>0.05). At 5 days, Simpson end systolic volumes were 35.8±2.9 µL for the untreated control and 31.3±2.7 µL for the EA-CPC-treated group (p>0.05). At 35 days, Simpson end systolic volumes were significantly smaller (p<0.05) in the EA-CPC treatment group (38.3±4.1 µL) than control group (55.4±4.6 µL). Human EA-CPCs thus abrogated LV dilatation and adverse remodeling after ischemia/reperfusion injury that is known to lead to heart failure as well as promote restoration of systolic function after ischemic injury.

Stroke work and cardiac output were also tested in vehicle controls (n=11) and EA-CPC-treated (n=13) groups at 35 days measured by standard Millar methodology. The vehicle control group had an average stroke work of 497.3±48.4 mm Hg·µL, whereas the EA-CPC treatment group had a statistically significantly higher average stroke work of 666.8.±44.5 mm Hg·µL (p<0.05). Regarding cardiac output, the vehicle control group had an average cardiac output of 4128±326 mL/minute, whereas the EA-CPC treatment group had a statistically significantly higher average cardiac output of 4757±250 mL/minute (p<0.05). Thus, these functional parameters were observed to be significantly increased or improved as a result of EA-CPC treatment as compared to vehicle control in SCID mice that had undergone ischemic injury as outlined herein above.

Average body weight and heart rate measurements were also taken in untreated (n=11) vs. EA-CPC-treated (n=13) mice during echocardiographic study. Body weight (untreated: 23.3±0.6 grams vs. EA-CPC-treated: 23.9±0.3 grams; p>0.05) and heart rate (untreated: 469.1±14.9 beats per minute (bpm) vs. EA-CPC-treated: 443.3±13.1 bpm; p>0.05) were not significantly different at 35 days in in untreated vs. EA-CPC-treated mice.

Discussion of the Examples

In summary, provided herein is direct evidence for the existence of multipotent SSEA3-positive CPCs, referred to herein as EA-CPCs. SSEA3-positive EA-CPCs were not culture-derived artifacts, but existed in the native human neonatal and adult myocardium. Also described herein is that these SSEA3-positive EA-CPCs could be isolated and expanded in vitro, which could lead to using them in inducing repair of damaged and/or poorly functioning myocardium.

To confirm that these cells truly had a phenotype expected of progenitor cells, an extensive characterization of EA-CPCs is presented herein. Not only the expression of markers such as pluripotent stem cell-associated markers OCT4 and NANOG was validated, but also the expression of telomerase, which allowed these cells to preserve their progenitor phenotype and avoid excessive shortening of their telomeres with repetitive cell proliferation in vitro. Thusly, these cells retained a large proliferative reserve.

Also described herein is evidence that these cells possess a cardiac predisposition as they were characterized by heterogeneous baseline expression of transcription factors showing early commitment to several cardiac lineages, including endothelial cells, smooth muscle cells, and cardiomyocytes. Furthermore, SSEA3-positive EA-CPCs upregulated mature sarcomeric proteins characteristic of smooth muscle cells and myocytes upon in vitro differentiation.

In other words, SSEA3-positive EAS-CPCs had cardiac multilineage potential. This pattern of gene expression and organ specific predisposition is believed to be unique to progenitor cells isolated from the human heart, in contrast to any stated ability of other non-embryonic or neonatal non-cardiac stem cell populations that have not been shown to contribute directly to lineages of the heart or to its homeostasis.

As disclosed herein, of the instantly disclosed methods of isolation and expansion are highly reproducible, and further disclosed is that SSEA3-positive EA-CPC populations from different patients were characterized by preservation of very similar progenitor gene expression patterns.

Accordingly, disclosed herein are clinically relevant methodologies that showed exactly the characteristics and capabilities of SSEA3-positive EA-CPCs that would be used in a clinically relevant therapeutic application. With these methodologies, the present disclosure verified within a model of ischemically damaged myocardium that administration of human SSEA3-positive EA-CPCs could induce cardiac repair and abrogate adverse myocardial remodeling that leads to functional decompensation. Again, a comprehensive report of the discovery, characterization, and therapeutic utility of the kind disclosed herein related to adult progenitor cells has never been put forth, and furthermore, the clinically applicable methodology disclosed herein is believed to facilitate rapid bench to bedside applications without any major alterations and/or complications that can significantly change any of the data. As such, the present disclosure provides a compositions comprising therapeutically useful cells and cell populations, and methods of using the same to treat and/or ameliorate diseases and disorders of the heart.

REFERENCES

All references listed in the instant disclosure, including but not limited to all patents, patent applications and publications thereof, scientific journal articles, and database entries (including but not limited to GENBANK® biosequence database entries and all annotations available therein) are incorporated herein by reference in their entireties to the extent that they supplement, explain, provide a background for, or teach methodology, techniques, and/or compositions employed herein.

Anversa et al. (1998) Ventricular myocytes are not terminally differentiated in the adult mammalian heart. *Circ Res* 82:1231-1233.

Bearzi et al. (2007) Human cardiac stem cells. 104 *Proc Natl Acad Sci USA* 14068-14073.

Beltrami et al. (2001) Evidence that human cardiac myocytes divide after myocardial infarction. *N Engl J Med* 344:1750-1757.

Beltrami et al. (2003) Adult cardiac stem cells are multipotent and support myocardial regeneration. 114 *Cell* 763-776.

Goumans et al. (2007) TGF-beta1 induces efficient differentiation of human cardiomyocyte progenitor cells into functional cardiomyocytes in vitro. *Stem Cell Res* 1:138-149.

Hierlihy et al. (2002) The post-natal heart contains a myocardial stem cell population. *FEBS Lett* 530:239-243.

Kajstura et al. (1998) Myocyte proliferation in end-stage cardiac failure in humans. *Proc Natl Acad Sci USA* 95:8801-8805.

Laugwitz et al. (2005) Postnatal isl1-positive cardioblasts enter fully differentiated cardiomyocyte lineages. *Nature* 433:647-653. *Erratum in Nature* 446:934.

Leor et al. (2000) Bioengineered Cardiac Grafts. A New Approach to Repair the Infarcted Myocardium? *Circulation* 102[suppl III]:III-56-III-61.

Liang et al. (2010) Switching of core structures of glycosphingolipids from globo- and lacto- to ganglio-series on human embryonic stem cell differentiation. *Proc Natl Acad Sci USA*. 107:22564-22569.

Messina et al. (2004) Isolation and expansion of adult cardiac stem cells from human and murine heart. *Circ Res* 95:911-912.

Mewhort et al. (2013) Epicardial infarct repair with basic fibroblast growth factor-enhanced CorMatrix-ECM biomaterial attenuates postischemic cardiac remodeling. *J Thorac Cardiovasc Surg* [Epub ahead of print]; now Mewhort et al. (2014) Epicardial infarct repair with basic fibroblast growth factor-enhanced CorMatrix-ECM biomaterial attenuates postischemic cardiac remodeling. *J Thorac Cardiovasc Surg* 147:1650-1659).

Moriarty (1980) The law of Laplace. Its limitations as a relation for diastolic pressure, volume, or wall stress. *Circ Res* 46:321-331.

Smith et al. (2007) Regenerative potential of cardiosphere-derived cells expanded from percutaneous endomyocardial biopsy specimens. *Circulation* 115:896-908.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A pharmaceutical composition comprising a pharmaceutically acceptable carrier and isolated SSEA3-positive/c-kit-negative cardiac progenitor cells (CPCs), in vitro expanded SSEA3-positive/c-kit-negative progeny cells thereof, or a combination thereof, wherein the isolated SSEA3-positive/c-kit-negative CPCs are isolated from post-natal myocardium.

2. The pharmaceutical composition of claim 1, wherein the CPCs are isolated from human post-natal myocardium.

3. The pharmaceutical composition of claim 1, wherein the concentration of CPCs is about $1 \times 10^5$ cells/ml to about $1 \times 10^9$ cells/ml in the pharmaceutical composition.

4. The pharmaceutical composition of claim 1, wherein the pharmaceutical composition further comprises one or more cell types selected from the group consisting of non-cardiac-derived SSEA3-positive cells, SSEA4-positive cells, c-kit-positive cardiac stem cells, hematopoietic stem cells (HSCs), mesenchymal stem cells (MSCs), endothelial progenitor cells (EPCs), bone marrow cells (BMCs), aldehyde dehydrogenase positive (ALDH-positive) cells, very small embryonic like cells (VSELs), cardiosphere-derived cells (CDCs), or a combination thereof.

5. The pharmaceutical composition of claim 1, wherein the pharmaceutically acceptable carrier is acceptable for use in a human.

6. The pharmaceutical composition of claim 1, wherein the pharmaceutical composition further comprises one or more growth factors, cytokines, or a combination thereof.

7. The pharmaceutical composition of claim 6, wherein the one or more growth factors and the one or more cytokines are selected from the group consisting of insulin-like growth factor I (IGF-I), fibroblast growth factor (FGF), hepatocyte growth factor (HGF), stromal-derived growth factor-1 (SDF-1), vascular endothelial growth factor (VEGF), a bone morphogeneic protein (BMP), platelet derived growth factor (PDGF), granulocyte-colony stimulating factor (G-CSF), granulocyte-macrophage-colony stimulating factor (GM-CSF), transforming growth factor-β (TGF-β), and stem cell factor (SCF).

8. The pharmaceutical composition of claim 1, wherein the pharmaceutical composition is formulated as an injectable.

9. The pharmaceutical composition of claim 8, wherein the CPCs, the in vitro expanded progeny cells thereof, or both are also CD34-negative, CD45-negative, or both CD34-negative and CD45-negative.

10. A cell culture comprising a population of post-natal SSEA3-positive/c-kit-negative cardiac progenitor cells (CPCs) and/or progeny cells thereof growing on a surface, wherein at least about 50% of the population of post-natal CPCs and/or the progeny cells thereof present in the cell culture are SSEA3-positive/c-kit-negative.

11. The cell culture of claim 10, wherein the SSEA3-positive/c-kit-negative post-natal CPCs and/or the progeny cells thereof are maintained as subconfluent in the cell culture.

12. The cell culture of claim 10, wherein the surface upon which the SSEA3-positive/c-kit-negative CPCs and/or the progeny cells thereof are growing comprises a growth-promoting medium or substrate selected from the group consisting of poly-lysine, gelatin, MATRIGEL®, fibronectin, vitronectin, an extracellular matrix component, and a scaffold, or any combination thereof.

13. The cell culture of claim 10, wherein the SSEA3-positive/c-kit-negative CPCs and/or the progeny cells thereof express at least one cardiac-specific marker selected from the group consisting of Nkx2.5, Gata4, Mef2c, Isl1, and Gata6; one or more pluripotency-associated markers selected from the group consisting of Oct3, Oct4, Nanog, and Sox2; one or more other markers selected from the group consisting of SSEA1, CD105, CD73, CD90, CD29, CD44, CD166, SSEA5, ALDH, and alkaline phosphatase; or any combination thereof.

14. The cell culture of claim 10, wherein the post-natal SSEA3-positive/c-kit-negative cardiac progenitor cells (CPCs) and/or the progeny cells thereof are also CD34-negative, CD45-negative, or both CD34-negative and CD45-negative.

15. A method for preparing an isolated cell population enriched in post-natal SSEA3-positive/c-kit-negative cardiac progenitor cells (CPCs), the method comprising:
   (a) disrupting a cardiac tissue sample obtained from a post-natal subject to obtain tissue fragments and/or single cells;
   (b) culturing the tissue fragments and/or single cells in a culture medium for a time and under conditions sufficient to generate $10^4$-$10^9$ cells;
   (c) harvesting all or at least a portion of the adhered tissue fragments and/or single cells from the culture;
   (d) purifying one or more subpopulations selected from the group consisting of a subpopulation of SSEA3-positive/c-kit-negative cells, a subpopulation of SSEA3-positive/c-kit-negative/CD34-negative cells, a subpopulation of SSEA3-positive/c-kit-negative/CD45-negative cells, and a subpopulation of SSEA3-positive/c-kit-negative/CD34-negative/CD45-negative cells from the single cell suspension; and
   (e) expanding the one or more subpopulations in culture for a time and under conditions sufficient to generate at least about $10^4$ SSEA3-positive/c-kit-negative cells that are also optionally CD34-negative and/or CD45-negative,
   wherein an isolated cell population enriched in post-natal SSEA3-positive/c-kit-negative cardiac progenitor cells (CPCs) that are also optionally CD34-negative and/or CD45-negative is prepared.

16. The method of claim 15, wherein the cardiac tissue sample comprises tissue and/or cells isolated from and/or expanded from cardiac right atrial appendage tissue, left atrial appendage tissue, cardiac ventricular tissue, cardiac valvular tissue, cardiac vascular tissue, and/or endomyocardial biopsy tissue.

17. The method of claim 15, wherein cells of the one or more subpopulations express one or more markers selected from the group consisting of ISL1, GATA4, NKX2.5, MEF2C, GATA6, BRACHYURY, MESP1, OCT3, OCT4, NANOG, and SOX2.

18. The method of claim 15, wherein the tissue fragments and/or single cells are cultured in the absence of exogenously added feeder cells.

19. The method of claim 15, wherein the culturing is on a support that comprises a growth-promoting medium selected from the group consisting of poly-lysine, gelatin, MATRIGEL®, fibronectin, laminin, collagen, vitronectin, an extracellular matrix component, and a natural and/or synthetic scaffold.

20. The method of claim 15, wherein the culturing is in a medium that comprises at least one growth promoting factor selected from the group consisting of IGF-1, FGF, a BMP, EGF, SCF, PDGF, and VEGF.

21. The method of claim 15, further comprising disrupting the harvested cells to produce a single cell suspension prior to the purifying step.

* * * * *

SEQUENCE LISTING

```
<160> NUMBER OF SEQ ID NOS: 64

<210> SEQ ID NO 1
<211> LENGTH: 18
<212> TYPE: DNA
<213> ORGANISM: Homo Sapiens

<400> SEQUENCE: 1
aatgcggcat cttcaaac                                                 18

<210> SEQ ID NO 2
<211> LENGTH: 18
<212> TYPE: DNA
<213> ORGANISM: Homo Sapiens

<400> SEQUENCE: 2
tgactttgtc acagccca                                                 18

<210> SEQ ID NO 3
<211> LENGTH: 18
<212> TYPE: DNA
<213> ORGANISM: Homo Sapiens

<400> SEQUENCE: 3
gatgtggtcc gagtgtgg                                                 18

<210> SEQ ID NO 4
<211> LENGTH: 18
<212> TYPE: DNA
<213> ORGANISM: Homo Sapiens

<400> SEQUENCE: 4
tgtgcatagt cgctgctt                                                 18

<210> SEQ ID NO 5
<211> LENGTH: 17
<212> TYPE: DNA
<213> ORGANISM: Homo Sapiens
```

```
<400> SEQUENCE: 5
gcagaaggcc tcagcac                                                  17

<210> SEQ ID NO 6
<211> LENGTH: 18
<212> TYPE: DNA
<213> ORGANISM: Homo Sapiens

<400> SEQUENCE: 6
aggttcccag tcgggttc                                                 18

<210> SEQ ID NO 7
<211> LENGTH: 18
<212> TYPE: DNA
<213> ORGANISM: Homo Sapiens

<400> SEQUENCE: 7
cccctggatt ttgcattc                                                 18

<210> SEQ ID NO 8
<211> LENGTH: 17
<212> TYPE: DNA
<213> ORGANISM: Homo Sapiens

<400> SEQUENCE: 8
cgtgcgcaag aacaaac                                                  17

<210> SEQ ID NO 9
<211> LENGTH: 21
<212> TYPE: DNA
<213> ORGANISM: Homo Sapiens

<400> SEQUENCE: 9
aacgacggca acaacgataa t                                             21

<210> SEQ ID NO 10
<211> LENGTH: 25
<212> TYPE: DNA
<213> ORGANISM: Homo Sapiens

<400> SEQUENCE: 10 gtttttccc ctttgatttt tgatc                                          25

<210> SEQ ID NO 11
<211> LENGTH: 20
<212> TYPE: DNA
<213> ORGANISM: Homo Sapiens

<400> SEQUENCE: 11
aagacaccag cagctccttc                                               20

<210> SEQ ID NO 12
<211> LENGTH: 20
<212> TYPE: DNA
<213> ORGANISM: Homo Sapiens

<400> SEQUENCE: 12
tgtgcccgta gtgagatgac                                               20

<210> SEQ ID NO 13
<211> LENGTH: 18
<212> TYPE: DNA
```

<213> ORGANISM: Homo Sapiens

<400> SEQUENCE: 13
ctggcaacag caacacct                                                   18

<210> SEQ ID NO 14
<211> LENGTH: 18
<212> TYPE: DNA
<213> ORGANISM: Homo Sapiens

<400> SEQUENCE: 14
gctagtgcaa gctcccaa                                                   18

<210> SEQ ID NO 15
<211> LENGTH: 18
<212> TYPE: DNA
<213> ORGANISM: Homo Sapiens

<400> SEQUENCE: 15
ccctgggtta caaggaag                                                   18

<210> SEQ ID NO 16
<211> LENGTH: 21
<212> TYPE: DNA
<213> ORGANISM: Homo Sapiens

<400> SEQUENCE: 16
agtgtcatga tctgtcctcc t                                               21

<210> SEQ ID NO 17
<211> LENGTH: 18
<212> TYPE: DNA
<213> ORGANISM: Homo Sapiens

<400> SEQUENCE: 17
ccagacggca ccgaagat                                                   18

<210> SEQ ID NO 18
<211> LENGTH: 22
<212> TYPE: DNA
<213> ORGANISM: Homo Sapiens

<400> SEQUENCE: 18
acatactcgt tgcccacttt ca                                              22

<210> SEQ ID NO 19
<211> LENGTH: 18
<212> TYPE: DNA
<213> ORGANISM: Homo Sapiens

<400> SEQUENCE: 19
ccaaccaagg ccgacaaa                                                   18

<210> SEQ ID NO 20
<211> LENGTH: 21
<212> TYPE: DNA
<213> ORGANISM: Homo Sapiens

<400> SEQUENCE: 20
ggcgggagtc acatctcttt c                                               21

<210> SEQ ID NO 21
<211> LENGTH: 23

<212> TYPE: DNA
<213> ORGANISM: Homo Sapiens

<400> SEQUENCE: 21
gagcaccaat catatttact cca                                        23

<210> SEQ ID NO 22
<211> LENGTH: 20
<212> TYPE: DNA
<213> ORGANISM: Homo Sapiens

<400> SEQUENCE: 22
gaattgatcc gcacagaatg                                            20

<210> SEQ ID NO 23
<211> LENGTH: 17
<212> TYPE: DNA
<213> ORGANISM: Homo Sapiens

<400> SEQUENCE: 23
ccaaccaagg ccgacaa                                               17

<210> SEQ ID NO 24
<211> LENGTH: 18
<212> TYPE: DNA
<213> ORGANISM: Homo Sapiens

<400> SEQUENCE: 24
ggcgggagtc acatctct                                              18

<210> SEQ ID NO 25
<211> LENGTH: 19
<212> TYPE: DNA
<213> ORGANISM: Homo Sapiens

<400> SEQUENCE: 25
acgccgctcc tccaactac                                             19

<210> SEQ ID NO 26
<211> LENGTH: 21
<212> TYPE: DNA
<213> ORGANISM: Homo Sapiens

<400> SEQUENCE: 26
cagcagagtc ttcagctgca a                                          21

<210> SEQ ID NO 27
<211> LENGTH: 18
<212> TYPE: DNA
<213> ORGANISM: Homo Sapiens

<400> SEQUENCE: 27
aaagagggaa ttcaaacc                                              18

<210> SEQ ID NO 28
<211> LENGTH: 18
<212> TYPE: DNA
<213> ORGANISM: Homo Sapiens

<400> SEQUENCE: 28
gaagttggag tcatggga                                              18

<210> SEQ ID NO 29

-continued

```
<211> LENGTH: 18
<212> TYPE: DNA
<213> ORGANISM: Homo Sapiens

<400> SEQUENCE: 29
gaggagaagt ccctcagt                                                 18

<210> SEQ ID NO 30
<211> LENGTH: 18
<212> TYPE: DNA
<213> ORGANISM: Homo Sapiens

<400> SEQUENCE: 30
acttggaagc tgtaacag                                                 18

<210> SEQ ID NO 31
<211> LENGTH: 20
<212> TYPE: DNA
<213> ORGANISM: Homo Sapiens

<400> SEQUENCE: 31
tgggcgagat gtggtacaga                                               20

<210> SEQ ID NO 32
<211> LENGTH: 19
<212> TYPE: DNA
<213> ORGANISM: Homo Sapiens

<400> SEQUENCE: 32
tcacgcgggt gagtatcca                                                19

<210> SEQ ID NO 33
<211> LENGTH: 20
<212> TYPE: DNA
<213> ORGANISM: Homo Sapiens

<400> SEQUENCE: 33
cgtcgagctg ctcaggtctt                                               20

<210> SEQ ID NO 34
<211> LENGTH: 23
<212> TYPE: DNA
<213> ORGANISM: Homo Sapiens

<400> SEQUENCE: 34
agtgctgtct gattccaatg ctt                                           23

<210> SEQ ID NO 35
<211> LENGTH: 20
<212> TYPE: DNA
<213> ORGANISM: Homo Sapiens

<400> SEQUENCE: 35
gccacgtctc taccttgaca                                               20

<210> SEQ ID NO 36
<211> LENGTH: 19
<212> TYPE: DNA
<213> ORGANISM: Homo Sapiens

<400> SEQUENCE: 36
gaggagctct gctcgatga                                                19
```

```
<210> SEQ ID NO 37
<211> LENGTH: 20
<212> TYPE: DNA
<213> ORGANISM: Homo Sapiens

<400> SEQUENCE: 37
ggttgtacgg gatcaaatgc                                               20

<210> SEQ ID NO 38
<211> LENGTH: 20
<212> TYPE: DNA
<213> ORGANISM: Homo Sapiens

<400> SEQUENCE: 38
gcccgtcatc tctaccagtt                                               20

<210> SEQ ID NO 39
<211> LENGTH: 20
<212> TYPE: DNA
<213> ORGANISM: Homo Sapiens

<400> SEQUENCE: 39
gttaccagcc accttggaaa                                               20

<210> SEQ ID NO 40
<211> LENGTH: 20
<212> TYPE: DNA
<213> ORGANISM: Homo Sapiens

<400> SEQUENCE: 40
ttcccacttt ctccaacagg                                               20

<210> SEQ ID NO 41
<211> LENGTH: 20
<212> TYPE: DNA
<213> ORGANISM: Homo Sapiens

<400> SEQUENCE: 41
ttctgcactc acgtctttcc                                               20

<210> SEQ ID NO 42
<211> LENGTH: 20
<212> TYPE: DNA
<213> ORGANISM: Homo Sapiens

<400> SEQUENCE: 42
tggcaaaggg attattctca                                               20

<210> SEQ ID NO 43
<211> LENGTH: 20
<212> TYPE: DNA
<213> ORGANISM: Homo Sapiens

<400> SEQUENCE: 43
caacagaatg ggtttggaag                                               20

<210> SEQ ID NO 44
<211> LENGTH: 20
<212> TYPE: DNA
<213> ORGANISM: Homo Sapiens

<400> SEQUENCE: 44
aaggtggagg aacttgcatt                                               20
```

```
<210> SEQ ID NO 45
<211> LENGTH: 20
<212> TYPE: DNA
<213> ORGANISM: Homo Sapiens

<400> SEQUENCE: 45
agctttggga caaattccat                                              20

<210> SEQ ID NO 46
<211> LENGTH: 18
<212> TYPE: DNA
<213> ORGANISM: Homo Sapiens

<400> SEQUENCE: 46
cttggcctca ggatccac                                                18

<210> SEQ ID NO 47
<211> LENGTH: 20
<212> TYPE: DNA
<213> ORGANISM: Homo Sapiens

<400> SEQUENCE: 47
aggtgagtgt cccagaggag                                              20

<210> SEQ ID NO 48
<211> LENGTH: 20
<212> TYPE: DNA
<213> ORGANISM: Homo Sapiens

<400> SEQUENCE: 48
ggtctgtccc attgagcttc                                              20

<210> SEQ ID NO 49
<211> LENGTH: 20
<212> TYPE: DNA
<213> ORGANISM: Homo Sapiens

<400> SEQUENCE: 49
ggcttcattg acaagaacga                                              20

<210> SEQ ID NO 50
<211> LENGTH: 20
<212> TYPE: DNA
<213> ORGANISM: Homo Sapiens

<400> SEQUENCE: 50
ggagcctcct tgatcatttc                                              20

<210> SEQ ID NO 51
<211> LENGTH: 20
<212> TYPE: DNA
<213> ORGANISM: Homo Sapiens

<400> SEQUENCE: 51
ggcatctgag accagtgaga                                              20

<210> SEQ ID NO 52
<211> LENGTH: 20
<212> TYPE: DNA
<213> ORGANISM: Homo Sapiens

<400> SEQUENCE: 52
tttctcacca gtgtgcttcc                                              20
```

<210> SEQ ID NO 53
<211> LENGTH: 26
<212> TYPE: DNA
<213> ORGANISM: Homo Sapiens

<400> SEQUENCE: 53
gtgctgtccc aggtggctta cagatg                                        26

<210> SEQ ID NO 54
<211> LENGTH: 27
<212> TYPE: DNA
<213> ORGANISM: Homo Sapiens

<400> SEQUENCE: 54
ccttaacagc tcaactctaa ctacttg                                       27

<210> SEQ ID NO 55
<211> LENGTH: 18
<212> TYPE: DNA
<213> ORGANISM: Homo Sapiens

<400> SEQUENCE: 55
tgctgcaatc ccatgaca                                                 18

<210> SEQ ID NO 56
<211> LENGTH: 18
<212> TYPE: DNA
<213> ORGANISM: Homo Sapiens

<400> SEQUENCE: 56
cgttgctcac agaccaca                                                 18

<210> SEQ ID NO 57
<211> LENGTH: 20
<212> TYPE: DNA
<213> ORGANISM: Homo Sapiens

<400> SEQUENCE: 57
ggatccaggt atggttccag                                               20

<210> SEQ ID NO 58
<211> LENGTH: 20
<212> TYPE: DNA
<213> ORGANISM: Homo Sapiens

<400> SEQUENCE: 58
ggagcacagt ggttgaggat                                               20

<210> SEQ ID NO 59
<211> LENGTH: 18
<212> TYPE: DNA
<213> ORGANISM: Homo Sapiens

<400> SEQUENCE: 59
tgggttcggt ggtcaagt                                                 18

<210> SEQ ID NO 60
<211> LENGTH: 19
<212> TYPE: DNA
<213> ORGANISM: Homo Sapiens

<400> SEQUENCE: 60

```
ctctggtagt gctgggaca                                                 19

<210> SEQ ID NO 61
<211> LENGTH: 20
<212> TYPE: DNA
<213> ORGANISM: Homo Sapiens

<400> SEQUENCE: 61
cgctatatcg gccacctgtc                                                20

<210> SEQ ID NO 62
<211> LENGTH: 20
<212> TYPE: DNA
<213> ORGANISM: Homo Sapiens

<400> SEQUENCE: 62
ggcatccagg tctccaacag                                                20

<210> SEQ ID NO 63
<211> LENGTH: 19
<212> TYPE: DNA
<213> ORGANISM: Homo Sapiens

<400> SEQUENCE: 63
agccacatcg ctcagacac                                                 19

<210> SEQ ID NO 64
<211> LENGTH: 19
<212> TYPE: DNA
<213> ORGANISM: Homo Sapiens

<400> SEQUENCE: 64
gcccaatacg accaaatcc                                                 19
```